United States Patent
Danopoulos

(10) Patent No.: US 12,138,607 B2
(45) Date of Patent: Nov. 12, 2024

(54) METHODS AND SYSTEMS FOR COMPOSITION COMPOUNDING

(71) Applicant: MEDISCA PHARMACEUTIQUE INC., St-Laurent (CA)

(72) Inventor: Panagiota Danopoulos, Montreal (CA)

(73) Assignee: MEDISCA PHARMACEUTIQUE INC., St-Laurent (CA)

( * ) Notice: Subject to any disclaimer, the term of this patent is extended or adjusted under 35 U.S.C. 154(b) by 823 days.

(21) Appl. No.: 17/134,062

(22) Filed: Dec. 24, 2020

(65) Prior Publication Data

US 2022/0008878 A1    Jan. 13, 2022

Related U.S. Application Data

(60) Provisional application No. 63/051,281, filed on Jul. 13, 2020.

(51) Int. Cl.
  *B01F 33/00* (2022.01)
  *B01F 27/95* (2022.01)
  (Continued)

(52) U.S. Cl.
  CPC .......... *B01F 33/8442* (2022.01); *B01F 27/95* (2022.01); *B01F 33/848* (2022.01);
  (Continued)

(58) Field of Classification Search
  CPC ............. B01F 35/2206; B01F 35/2207; G06K 7/10366; G06K 7/1413; G06K 7/1417
  See application file for complete search history.

(56) References Cited

U.S. PATENT DOCUMENTS 3,472,787 A    10/1969 Kucirka
5,207,642 A    5/1993 Orkin et al.
(Continued)

FOREIGN PATENT DOCUMENTS

CA    3104321    2/2022

OTHER PUBLICATIONS

Orlova et al., "Variation in Mechanical Properties Due to the Effect of Electric Potential," IOP Conference Series: Materials Science and Engineering, Aug. 1, 2017, 225(1):012218, 10 pages.
(Continued)

*Primary Examiner* — Anshu Bhatia
(74) *Attorney, Agent, or Firm* — Finnegan, Henderson, Farabow, Garrett & Dunner LLP

(57) ABSTRACT

Systems and methods that implement a GUI functional block that allows a user to specify a compounding formula for a composition, an ingredient validation functional block configured for receiving a code on a container holding a first ingredient, consulting a database to derive a formulation ingredient to be used in preparing the composition, determining if the first ingredient matches the formulation ingredient, a planetary mixer control functional block configured for consulting the database arrangement at least partly on a basis of the specified compounding formula to determine mixing parameters for a planetary mixer that are associated with the specified compounding formula, causing a motor assembly of the planetary mixer to apply superimposed rotation and revolution movements to a container in accordance with the mixing parameters determined from the consulting, preventing operation of the motor assembly if the determining step fails to match the first ingredient to the formulation ingredient.

30 Claims, 63 Drawing Sheets

(51) Int. Cl.
  *B01F 33/84* (2022.01)
  *B01F 35/22* (2022.01)
  *G06F 3/0482* (2013.01)
  *G06K 7/10* (2006.01)
  *G06K 7/14* (2006.01)
  *G16H 20/13* (2018.01)
  *B01F 101/00* (2022.01)
  *B01F 101/22* (2022.01)

(52) U.S. Cl.
  CPC ...... *B01F 35/2206* (2022.01); *B01F 35/2207* (2022.01); *G06F 3/0482* (2013.01); *G06K 7/10366* (2013.01); *G06K 7/1413* (2013.01); *G06K 7/1417* (2013.01); *G16H 20/13* (2018.01); *B01F 2101/22* (2022.01); *B01F 2101/2202* (2022.01)

(56) References Cited

U.S. PATENT DOCUMENTS

| | | | |
|---|---|---|---|
| 7,317,967 B2 | 1/2008 | DiGianfilippo et al. | |
| 7,794,827 B2 | 9/2010 | Palmer et al. | |
| 10,512,885 B2* | 12/2019 | Janders | F16K 11/22 |
| 2005/0086008 A1* | 4/2005 | DiGianfilippo | G07F 13/06 702/19 |
| 2019/0209984 A1 | 7/2019 | Lubow et al. | |
| 2021/0069910 A1 | 3/2021 | Oleynik | |
| 2022/0008877 A1 | 1/2022 | Danopoulos et al. | |

OTHER PUBLICATIONS

Corrected Notice of Allowability in U.S. Appl. No. 17/201,885, dated Jan. 28, 2022, 2 pages.

Examiner's Report in Canadian Appln. No. 3,104,321, dated Mar. 4, 2021, 3 pages.

Notice of Allowance in Canadian Appln. No. 3,104,321, dated Aug. 23, 2021, 1 page.

Notice of Allowance in U.S. Appl. No. 17/201,885, dated Jan. 21, 2022, 8 pages.

Office Action in U.S. Appl. No. 17/201,885, dated May 27, 2021, 18 pages.

* cited by examiner

1210

| Formula | Total Weight | Operating Parameters |
|---|---|---|
| ABC | 1-100g | 45 seconds @ 2000 rpm |
| | 101-500g | 1 minute @ 2500 rpm |
| XYZ | 1-500g | 1 minute @ 2000 rpm |
| | 501-1000g | 2 minutes @ 1800 rpm |
| ... | ... | ... |

FIG. 3A

Mixer Functionality: Mixing Cream/Gel Topicals

Formulation Property: HRT Cream Containing 10% or Less of Active Ingredients

Process Steps:

1) Weigh active powders directly in mixer
2) Add wetting agent on top of powders (optional)
3) Record gross weight of mixing container and preparation
4) Set counter-balance
5) Mix at X rpm for Y minutes
6) Add base on top of levigated powder
7) Record gross weight of mixing container and preparation
8) Set counter-balance
9) Mix and Z rpm for Y seconds

FIG. 3C

Mixer Functionality: Reduce Particle Size of Powders

Formulation Property: Crystalized and Large Particle Powders

Steps:

1) Weigh active powders directly in stainless steel mixing container
2) incorporate milling media
3) record gross weight of mixing container and preparation
4) Set counter-balance
5) Mix at X rpm for Y seconds
6) Take mixer container out and shake vigorously to prevent clumping
7) Mix again at Z rpm for W seconds
8) Remove beads by pouring micronized powder and beads over a large mm sieve or strainer
9) Add wetting agent
10) Mix at X rpm for Y seconds
11) Add base to levigated powder
12) Record gross weight of mixing container and preparation
13) Set counter balance
14) Mix at X rpm for W seconds

FIG. 3D

Compounding Record

3800

Record #:  Date:

Patient Name:  Composition name: ABC  Type: Cream  Dosage: 10%

Reference Master Formulation Record: 123  SOP# consulted: 1260  Mixer # used: 2

List of ingredients used: View

Amount of ingredients used  View  Source of ingredients used: View

Beyond Use Date: November 19, 2021

Use label: printed – affixed  Storage: printed – affixed  Beyond-use date (BUD): printed – affixed Inconsistencies: N/A  Prepared by: John Doe  Approved by: Allen Smith

METHODS AND SYSTEMS FOR COMPOSITION COMPOUNDING

CROSS-REFERENCE TO RELATED APPLICATIONS

This application claims the benefit of U.S. Provisional Patent Application Ser. No. 63/051,281 filed on Jul. 13, 2020. The contents of the aforementioned application are incorporated by reference herein.

TECHNICAL FIELD

The present disclosure relates to composition compounding using planetary mixers.

BACKGROUND

Planetary mixers are specialized machines used in homogenizing and degassing liquids such as paints, dyes and adhesives. They are also used for mixing and micronizing powders. Planetary mixers use a combination of rotation and revolution of a container to achieve a high degree of performance (homogenizing, degassing, micronizing, etc.) in a short amount of operating time.

Small-batch compounding with planetary mixers can waste a significant amount of time and product in search of operating parameters that yield satisfactory results for specific applications. Also, problems can arise due to human error being introduced into the mixing process. Current operation of planetary mixers is also largely reliant upon a user, which increases the probability that human error is introduced either during the mixing or record-making processes. This creates a liability in terms of complying with existing regulatory requirements and/or recommendations. Also, the lack of integration between planetary mixers and pharmacy inventories further complicates inventory management.

SUMMARY

This Summary is provided to introduce a selection of concepts in a simplified form that are further described below in the Detailed Description. This Summary is not intended to identify key aspects or essential aspects of the claimed subject matter.

This description relates to the use of "smart" mixing systems in the creation of liquids or gels for customized compounding compositions (e.g., pharmaceutical compounding). Such smart mixing systems use planetary mixers in communication with ingredient databases, formula databases, and other tools. These tools allow users to formulate compounding compositions with greater quality assurance by providing standard operating procedures (SOPs) and instructions to the user (e.g., ingredient lists and amounts, order of addition of reagents) and to the mixer (e.g., mixing speeds, mixing times). These tools can prevent ingredient error, for example by validating each ingredient added to the mixer by the user for correct identification, expiration date, weight, concentration, etc. Management of ingredient inventory can be automatically updated and maintained, as can records of the compounding compositions created. Such capabilities are particularly advantageous in compounding settings where mixing processes are small-batch and customized.

In some embodiments, a non-transitory medium storing computer-readable instructions which when read and executed by at least one processor of a computing device, implement a Graphical User Interface (GUI) functional block configured for implementing a computerized GUI that provides a user of the computing device with an opportunity to specify a compounding formula for a pharmaceutical or a skin-care composition, an ingredient validation functional block configured for: receiving a code generated by a code-reader when reading machine-readable data applied on a container holding a first ingredient, wherein the code conveys one or more characteristics of the first ingredient, consulting a database arrangement at least in part on the basis of the compounding formula to derive a formulation ingredient to be used in preparing the composition, determining at least in part on the basis of the code if the first ingredient matches the formulation ingredient, a planetary mixer control functional block configured for: consulting the database arrangement at least partly on a basis of the specified compounding formula to determine mixing parameters for a planetary mixer, the mixing parameters being associated with the specified compounding formula, causing a motor assembly of the planetary mixer to apply superimposed rotation and revolution movements to a container in accordance with the mixing parameters determined from the consulting, preventing operation of the motor assembly if the determining step fails to match the first ingredient to the formulation ingredient.

Embodiments include one or more of the following features: the ingredient validation functional block is configured for: receiving a plurality of codes sequentially input by the code reader as the code reader sequentially reads machine-readable data on a plurality of containers holding respective ingredients, wherein each code conveys one or more characteristics of the respective ingredient, consulting the database arrangement at least in part on the basis of the compounding formula to derive a plurality of formulation ingredients to be used in preparing the composition, determining at least in part on the basis of the codes if the ingredients held in the plurality of containers match the formulation ingredients. The planetary mixer control functional block is configured to prevent operation of the motor assembly when the determining step fails to match all the codes to the formulation ingredients. The GUI functional block is responsive to the ingredient validation functional block to display an error message on the GUI when the determining fails to match the code to the formulation ingredient. The error message indicates that the ingredient held in the container is incorrect for the specified compounding formula. The code is a first code and the container is a first container holding the first ingredient, the ingredient validation functional block is configured to receive a second code input by the code reader reading machine-readable data from a second container holding a second ingredient, determine at least in part on the basis of the second code if the second ingredient matches the formulation ingredient, and the planetary mixer control functional block being further configured to enable operation of the motor assembly when the determining determines that the second ingredient matches the formulation ingredient. The GUI functional block is responsive to input by the user to place the ingredient validation functional block in an operational state to: receive a second code from the code reader reading machine-readable data from a second container holding a second ingredient, determine at least in part from the second code if the second ingredient matches the formulation ingredient. The machine-readable data is optically read data. The optically read data is a bar-code or a QR code. The machine-readable data is an RFID data.

In some embodiments, a non-transitory medium storing computer-readable instructions which when read and executed by at least one processor of a computing device, implements: a GUI functional block configured for implementing a computerized GUI that provides a user of the computing device with an opportunity to specify a compounding formula for a pharmaceutical or a skin-care composition, an ingredient validation functional block configured for: receiving a code input by a code reader reading machine-readable data on a container holding a first ingredient, wherein the code is associated with the first ingredient, processing the code to determine if the first ingredient is a valid ingredient for the specified compounding formula, a planetary mixer control functional block configured for: consulting a database arrangement at least partly on a basis of the specified compounding formula in order to determine mixing parameters for a planetary mixer, the mixing parameters being associated with the specified compounding formula, causing a motor assembly of the planetary mixer to apply superimposed rotation and revolution movements to a container in accordance with the mixing parameters determined from the consulting, the planetary mixer control functional block being further configured to prevent operation of the motor assembly when the ingredient validation functional block determines that the first ingredient is not valid for the specified compounding formula.

Embodiments can include one or more of the following features: the ingredient validation functional block determines that the first ingredient is not valid when the first ingredient is a wrong ingredient for the specified compounding formula. The ingredient validation functional block determines that the first ingredient is not valid when the first ingredient has a use-by date that has passed. The ingredient validation functional block is configured to consult the database arrangement to derive at least in part from the code the use-by date of the first ingredient. The ingredient validation functional block is configured to consult the database arrangement to derive at least in part from the code the concentration of an active agent in the first ingredient. The ingredient validation functional block determines that the first ingredient is not valid when the first ingredient has a wrong concentration of an active agent. The machine-readable data is an optically read data. The optically read data is a bar-code or a QR code. The machine-readable data is an RFID data. The ingredient validation functional block is configured for receiving a plurality of codes sequentially input by the code reader as the code reader sequentially reads machine-readable data on a plurality of containers holding respective ingredients, wherein the plurality of codes are associated with respective ones of the ingredients, consulting the database arrangement at least in part on the basis of the specified compounding formula to derive a plurality of formulation ingredients to be used in preparing the composition, determining at least in part on the basis of the plurality of codes if the respective ingredients match the plurality of formulation ingredients. The GUI functional block is responsive to the ingredient validation functional block to display an error message on the GUI when step b (ii) determines that the first ingredient is not a valid ingredient.

In some embodiments, a non-transitory medium storing computer-readable instructions, which when read and executed by at least one processor of a computing device, implement a method, including: implementing a computerized GUI that provides a user of the computing device with an opportunity to specify a compounding formula for a pharmaceutical or a skin-care composition to be prepared by subjecting a plurality of ingredients to a mixing cycle in a planetary mixer, wherein the mixing cycle includes a plurality of mixing steps, where each mixing step includes applying superimposed rotation and revolution movements to a container including two or more of the ingredients therein, consulting a database arrangement at least partly on a basis of the specified compounding formula to derive mixing parameters for each step of the mixing cycle associated with the specified compounding formula, receiving a first code generated by a code-reader reading machine-readable data on a first container holding a first ingredient, wherein the first code is associated with the first ingredient, processing the first code for determining if the first ingredient is a valid ingredient for a first mixing step of the specified compounding formula. If step (d) determines that the first ingredient is a valid ingredient enabling the planetary mixer to perform the first mixing step of the plurality of mixing steps according to the determined mixing parameters for the first mixing step, receiving a second code input by the code reader in response to reading machine-readable data on a second container holding a second ingredient, wherein the second code is associated with the second ingredient, processing the second code to determine if the second ingredient is a valid ingredient for a second mixing step of the specified compounding formula, if step (g) determines that the second ingredient is a valid ingredient enabling the planetary mixer to perform a second mixing step of the plurality of mixing steps, including subjecting the first ingredient, the second ingredient and possibly additional ingredients to superimposed revolution and rotation movements according to the mixing parameters determined for the second mixing step.

Embodiments can include one or more of the following features: determining that either one of the first ingredient and the second ingredient is not valid when the first ingredient or the second ingredient is a wrong ingredient for the respective mixing step of the specified compounding formula. Determining that either one of the first ingredient and the second ingredient is not valid when either one of the first ingredient and the second ingredient has a use by date that has passed. Determining that either one of the first ingredient and the second ingredient is not valid when either one of the first ingredient and the second ingredient has a wrong concentration of active agent. The machine-readable data is an optically read data. The optically read data is a bar-code or a QR code.

In some embodiments, a computer-implemented method for compounding using a planetary mixer, comprising: specifying on a computerized GUI a compounded product to be prepared by mixing a plurality of ingredients in a planetary mixer, generating a first prompt on the GUI directing a user to scan a first container holding a first ingredient with a code-reader to read machine-readable data on the first container, to generate a first code associated with the first ingredient, consulting a database at least in part on a basis of the first code and the specified compounded product to determine if the first ingredient is a valid ingredient for the specified compounded product, obtaining machine instructions for the planetary mixer for performing a first mixing step of a plurality of mixing steps for preparing the compounded product and applying the machine instructions to the planetary mixer to cause the planetary mixer to perform the first mixing step which includes subjecting a container in which is placed the first ingredient and an additional ingredient to a superimposed rotation and revolution movements, generating a second prompt on the GUI directing the user to scan a second container holding a second ingredient with the code-reader to read machine-readable data on the second container, to generate a second code associated with the second ingredient, consulting the database to determine if the second ingredient is a valid ingredient for the specified compounded product, obtaining machine instructions for the planetary mixer for performing a second mixing step of the plurality of mixing steps for preparing the compounded product and applying the machine instructions to the planetary mixer to cause the planetary mixer to perform the second mixing step which includes subjecting the container in which are placed the first ingredient, the second ingredient and the additional ingredient to a superimposed rotation and revolution movements, disabling performance of the first mixing step or the second mixing step if the method determines that the first or second ingredients, respectively, is not valid.

Embodiments can include one or more of the following features: monitoring a lid sensor of the planetary mixer to determine whether the lid of the planetary mixer is open or closed. Disabling execution of the second mixing step until the lid sensor indicates that the lid has been operated after completion of the first mixing step.

Advantages of the mixers and systems described herein accrue due to the at least partial automation of compounding procedures. These advantages can be front-end and back-end advantages. Front-end advantages include reducing user error by providing step-by-step instructions to the user compounding a formula, validation of the ingredients introduced into the mixer, and automatic control of mixer parameters. The back-end advantages include simplifying administrative tasks for the user, for example by automatically updating inventories or fulfilling regulatory requirements.

All features of exemplary embodiments which are described in this disclosure and are not mutually exclusive can be combined with one another. Elements of one embodiment can be utilized in the other embodiments without further mention. Other aspects and features of the present invention will become apparent to those ordinarily skilled in the art upon review of the following description of specific embodiments in conjunction with the accompanying Figures.

BRIEF DESCRIPTION OF THE DRAWINGS

A detailed description of specific exemplary embodiments is provided herein below with reference to the accompanying drawings in which:

FIG. 3A illustrates a table for storing formula information.

FIGS. 3C and 3D are examples of operating procedures.

FIG. 30 illustrates a GUI on the user device that can appear during execution of the flowchart in FIG. 28.

Figure 1:
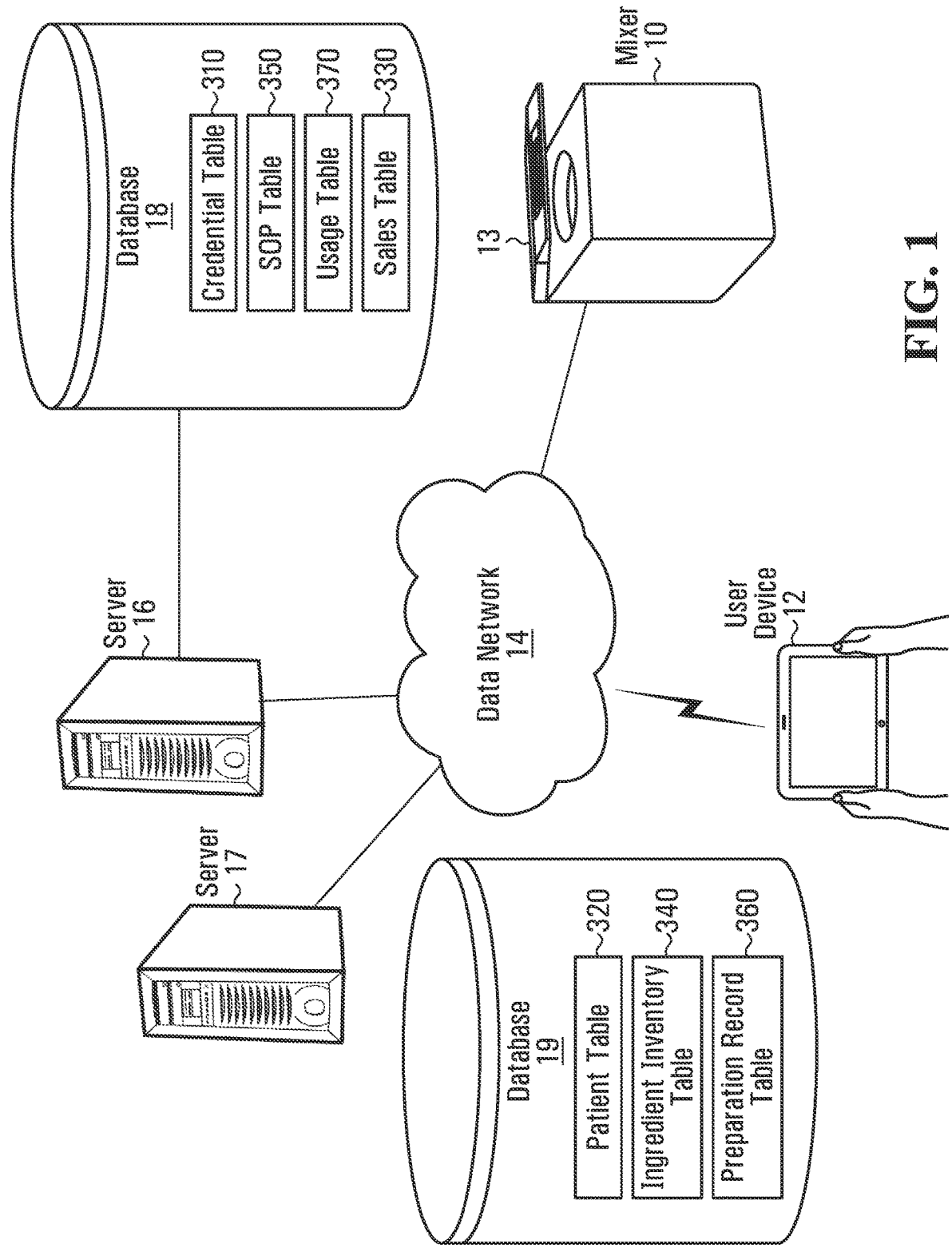
FIG. 1 shows a mixer system that communicates with a user device and a server over a data network.

In the drawings, exemplary embodiments are illustrated by way of example. It is to be expressly understood that the description and drawings are only for the purpose of illustrating certain embodiments and are an aid for understanding. They are not intended to be a definition of the limits of the invention.

DETAILED DESCRIPTION

System Overview

This description relates to the use of "smart" mixing systems in the creation of compounding compositions for customized compounding compositions (e.g., pharmaceutical compounding). These compounding compositions can be a cream, ointment, lotion, emulsion, gel, suspension, powder, liquid solution, colloidal dispersion, troche or syrup. Such smart mixing systems use planetary mixers in communication with ingredient databases, formula databases, and other tools. These tools allow users to formulate compounding compositions with greater quality assurance by providing standard operating procedures (SOPs) and instructions to the human or robotic operator (e.g., ingredient lists and amounts, order of addition of reagents) or to an automated operator such as a robotic arm, and to the mixer (e.g., mixing speeds, mixing times). These tools can prevent ingredient error, for example by validating each ingredient added to the mixer for correct identification, expiration date, weight, concentration, etc. Management of ingredient inventory can be automatically updated and maintained, as can records of the compounding compositions created. Such capabilities are particularly advantageous in compounding settings such as compounding labs found in pharmacies where mixing processes are small-batch and customized and performed by pharmacists and compounding technicians.

FIG. 1 shows a mixing system that includes a mixer 10 (e.g., a planetary mixer) with a lid 13, a user device 12, a data network 14, a first server 16, a second server 17, a first database 18, and a second database 19. The planetary mixer can have a variety of functions, such as mixing and de-aerating simultaneously by concurrently revolving and rotating a mixing container. Other functions of the planetary mixer can include milling and melting.

The user device 12 is configured to communicate with the first server 16 over the data network 14. The user device 12 can be a mobile phone, a tablet, a desktop PC or a console, etc. The user device 12 includes a memory, a processor, a screen, and a network interface, among other standard components. The memory of the user device 12 can store computer-readable instructions that are executed by the processor.

The mixer 10 and user device 12, along with associated software, upon connecting to first server 16 and second server 17 as well as accessing the first database 18 and the second database 19, can function as a hub that handles a plurality of front-end operations prior to and during compounding as well as back-end operations post-compounding. Such operations can include directing compounding processes, ingredient inventory management, controlling auxiliary devices (e.g., barcode readers or scales), accessing external databases (such as electronic health records), and records management.

The data network 14 can be a public data network (such as the Internet) or a local area network (a LAN). The first server 16 can be a World Wide Web server. The first database 18 can be part of a memory internal to the first server 16 or can be external to the first server 16 and connected thereto directly by a bus or over a data network (such as the internet). Similarly, the second database 19 can be part of a memory internal to the second server 17 or can be external to the second server 17 and connected directly thereto by a bus or over a data network (such as the internet).

Figure 2A:
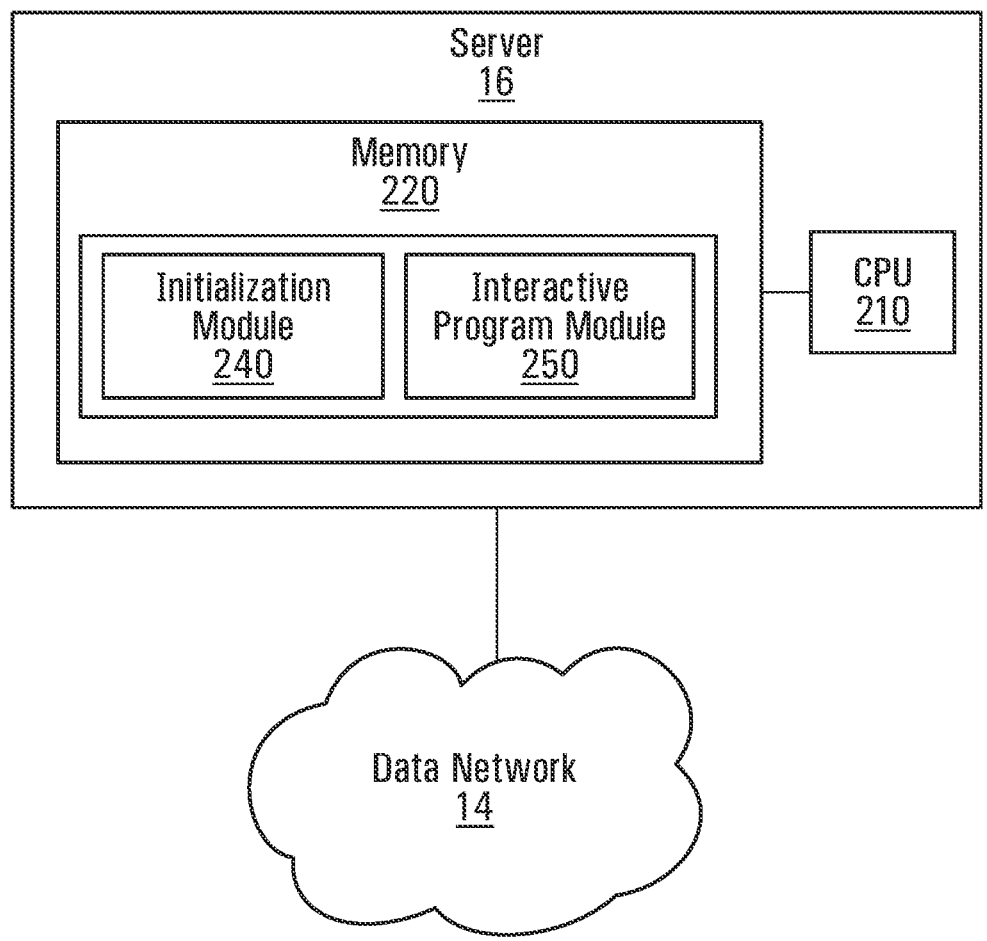
FIG. 2A is a block diagram showing components internal to the server.

Referring as well to FIG. 2A, the first server 16 includes a processor (CPU) 210 and a memory 220 that stores computer-readable instructions executable by the processor 210. Execution of the computer-readable instructions by the processor 210 causes the first server 16 to implement an initialization module 240 and an interactive program module 250 (also referred to as a "bot" or "wizard"). In some instances, the first server 16 can be managed by or be the property of a manufacturer or distributor of composition compounding equipment and/or materials. The second server 17 can have the same general architecture as the first server 16 but can be managed by or be the property of a pharmacy (that uses the mixer 10) or a service provider of pharmacy management or inventory services for the pharmacy.

Figure 2B:
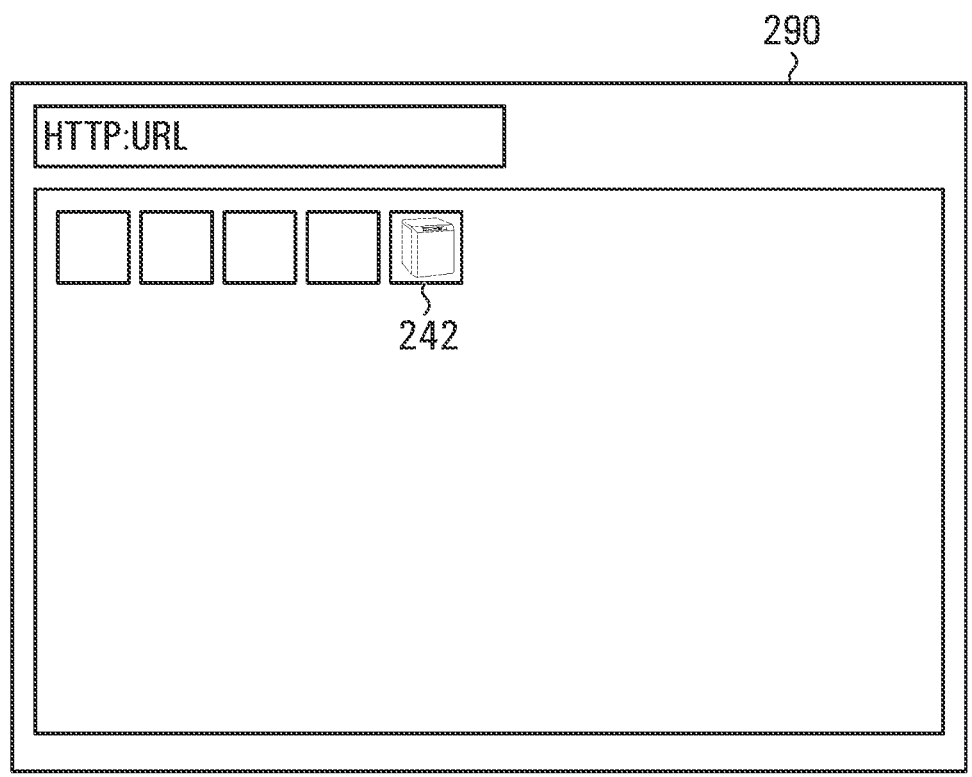
FIG. 2B shows a page for display on the user device during connection to the server.

A user can communicate with the server 16 by specifying an URL corresponding to the first server 16, or by activating a software application (an app) associated with the first server 16. Referring as well to FIG. 2B, in response to being contacted at the URL (or via the app), the first server 16 executes an initialization 240. The initialization module 240 can present an activatable link or icon 242 corresponding to the interactive program module 250 on the screen of the user device 12. The initialization module 240 is configured to detect activation (e.g., clicking or selecting through the user device 12) of the link or icon 242 and launch the interactive program module 250 in response.

The interactive program module 250 can act as a GUI functional block, such that launching the interactive program module 250 causes execution of computer-readable instructions which, when executed by the processor 210, cause the first server 16 to present a GUI 290 to the user device 12 over the data network 14.

The connection between the first server 16 and the user device 12 can be made via the mixer 10. The mixer 10 includes a computer platform that communicates with the first server 16 and with the user device 12. The communication can be wireless or wireline. Alternatively, the user device 12 can be physically integrated into the mixer 10 such as a display screen through which the user interacts directly with the mixer 10 and with the first server 16. The mixer 10 can automatically supply the first server 16 with identification information such as the model number, software versions, enabled functions, and let the first server 16 know the capabilities of the mixer 10 and the mixer 10 identity. The user credentials can be input via the user device 12 by any type of implementation separate from the mixer 10 or integrated therewith.

The mixer 10 can be communication-enabled or network-enabled. For example, the mixer 10 can be a stand-alone device in which a user or a robotic arm places the products to be mixed into the mixing container, weighs the container loaded with the product, sets the counter-balance to the corresponding value when using a single-container type mixer with a manual counter-balance mechanism (alternatively, the mixer can include an automatic counter-balance mechanism whereby the mixer detects the weight of the container loaded into the mixer and automatically adjusts the counter-balance mechanism), loads the container into the mixer 10, closes the lid 13, chooses settings, and pushes start. An example of a non-network-enabled mixer of this type can be any of the Maz™ mixer models KK-300SS, KK-400W and KK-1000W, sold by Medisca Pharmaceutique Inc. of St-Laurent, Canada.

Front End Uses

General Use of Networked Information (SOPs) with Mixers

The user may wish to create a specified composition compounding formula, e.g., to achieve a specific functionality for a specific formulation using a specific make and model of planetary mixer 10. The user may be interested in knowing the operating parameters for the user's mixer 10 for making the formulation given the corresponding formula (e.g., ingredients and their relative quantities) and the total quantity/volume. Referring to FIG. 3A, a formula database 1210 associates formulas with operating parameters for a mixer 10 according to weight of the mixture being compound. These operating parameters are supplied to the mixer 10.

The interactive program module 250 (shown in FIG. 2A) is configured to obtain and transmit an "SOP file" to a requesting user device such as the user device 12. An SOP file can be a computer-readable digital or electronic file that encodes or specifies an "operating procedure" (sometimes referred to as a "standard operating procedure" or SOP). An SOP can include an ordered set of process steps or operating parameters for operating the mixer 10 for the formulation of two or more ingredients combined in relative proportions defined by a formula.

Figure 3B:
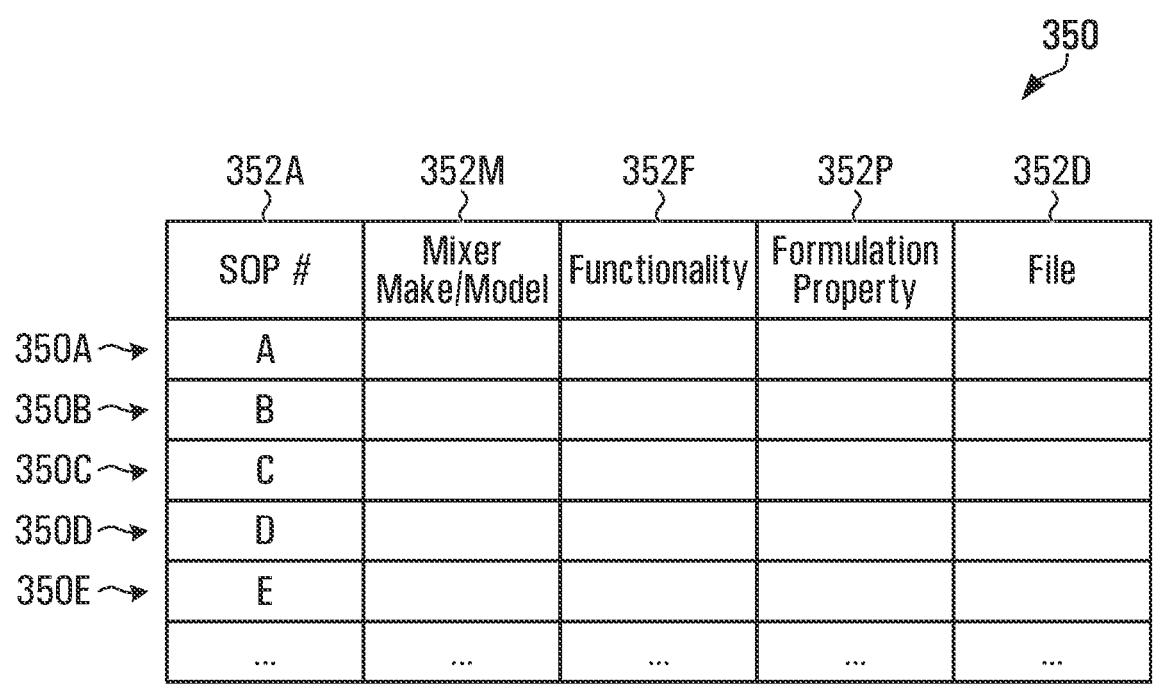
FIG. 3B illustrates a standard operating procedure (SOP) table for storing operating procedure information.

Referring to FIG. 3B, the first database 18 can be used for storing information and SOP files relevant to multiple operating procedures. FIG. 3B shows possible contents of the first database 18 as a table 350 of records 350A . . . 350E in memory, hereinafter referred to as an "SOP table". Each of the records 350A . . . 350E is associated with a respective operating procedure and includes a plurality of entries in a plurality of fields. The fields can include an SOP #field 352A, a mixer make/model field 352M, a functionality field 352F, a formulation property field 352P and a file field 352D.

The SOP #field 352A for the record associated with a given operating procedure stores a unique identifier of the given operating procedure.

The "functionality" field 352F can specify information regarding a specific use of the mixer 10. Examples of functionality are varied and can include one or more of (i) particle size reduction (micronization/grinding); (ii) melting; (iii) mixing of powders; (iv) mixing of creams/gels/topicals and (v) de-aerating (degassing).

The "formulation property" field 352P can specify information regarding the specific delivery form, dosage or other properties of the formulation that is to be produced by the mixer 10. Examples of formulation property are varied, and it is not an independent choice but rather depends on the mixer functionality. In some embodiments, formulation properties are selectable and a set of selectable formulation properties can be different for at least two different mixer functionalities. Table 1 shows an example association between mixer functionality and formulation property:

TABLE 1

| Mixer functionality: | Formulation property: |
| --- | --- |
| Particle size reduction | Lidocaine powder; Crystallized and large particle powders |
| Tablets | Enteric coated; Non-coated |
| Homogenizing powders | Progesterone capsules; Bi-estrogen capsules without progesterone; Bi-estrogen capsules with progesterone; Non-HRT powders |
| Mixing cream/gel/topical | HRT Cream containing 5% or less active ingredients; |
| compounding compositions | HRT Cream containing more than 5% active ingredients |

The "mixer make/model" field 352M for the record associated with a given operating procedure is optional and can identify the manufacturer, model and size of planetary mixer for which the given operating procedure has been designed. This is to accommodate differences in the calibration of RPM, counterbalance (if applicable), mixing time and order of steps from one manufacturer, model or size of planetary mixer to another, even where the mixer functionality and the formulation properties remain the same.

The "file" field 352D for the record associated with a given operating procedure includes a name of, or a pointer to, an SOP file, namely a digital or electronic file that encodes or specifies the given operating procedure. By way of example, the SOP file could be a text file that specifies the ordered set of process steps forming the given operating procedure (e.g., as shown in FIG. 3A).

The operating procedure encoded or specified by an SOP file can include a sequence of ordered process steps. Some of these process steps for operating the mixer can involve the setting of "operating parameters" for controlling operation of the mixer 10. The operating parameters can be provided to the mixer 10 using an input/output interface of the mixer 10 (such as a screen display with key/button input).

Examples of operating parameters that can be specified in a process step of a given operating procedure include one or more of:

rotation speed (in rpm),
  revolution speed (in rpm),
  time (in seconds); and
  counter-balance weight (in grams).

FIG. 3C shows a generalized example of contents of an SOP file for a first operating procedure. In this example, the mixer functionality is "mixing cream/gel/topical compounds" and the formulation property is "HRT Cream Containing 10% or Less of Active Ingredients" (where HRT is Hormone Replacement Therapy). This first operating procedure includes nine process steps. Process steps 4 and 5 involve mixing using a first set of operating parameters and process steps 8 and 9 involve mixing using a second set of operating parameters.

FIG. 3D shows a generalized example of contents of an SOP file for a second operating procedure. In this example, the mixer functionality is "particle size reduction" and the formulation property is "Crystalized and Large Particle Powders". This second operating procedure includes 14 process steps. Process steps 4 and 5 involve mixing using a first set of operating parameters, process step 7 using a second set, process step 10 using a third set, and process steps 13 and 14 using a fourth set of operating parameters.

A single process step can involve multiple consecutive mixing stages, each with its own operating parameters, together with intervening pauses. Table 2 shows an example of operating parameters that can be specified in two mixing stages of a given process step of a given operating procedure:

TABLE 2

| Process step 1 | Mixing stage 1 | Rotation @RT1 rpm |
| | | Revolution @RV1 rpm |
| | | Time T1 seconds |
| | | Counterbalance C1 grams |
| | Pause | P seconds |
| | Mixing stage 2 | Rotation @RT2 rpm |
| | | Revolution @RV2 rpm |
| | | Time T2 seconds |
| | | Counterbalance C2 grams |

The operating parameters can include revolution speeds of at least 400 revolutions per minute. For example, a suitable revolution speed can be in the range of 400 to about 4000 rpm, or 400 to about 2000 rpm, or any suitable value within these ranges. The operating parameters can include revolution:rotation rpm ratios of about 10:4.

The revolution rpm, the rotation rpm and the mixing time are configurable parameters and their values can be individually selectable. Alternatively, they can be selectable from pre-determined combinations of parameter values that are provided at the time of designing the operating procedure and creating its SOP file. The ratio between rotation rpm and revolution rpm can be a configurable parameter and thus would constrain the revolution rpm for a certain rotation rpm or vice versa. Moreover, the geometric configuration of the mixer 10 (e.g., the eccentricity (distance between the center of rotation and the center of revolution), the dimensions of the container, etc.), combined with the revolution rpm and rotation rpm, results in a certain acceleration (G-force, measured in g or $m/s^2$) being felt by the material in the container. The desired G-force can be an operating parameter input to the mixer 10, which could then result in selection, by the mixer 10, of a suitable revolution rpm and/or rotation rpm.

The desired G-force could be an operating parameter that forms part of one of a given one of the process steps of a given one of the SOP files stored in the first database 18. For example, the minimum or maximum G-force can be specified as an operating parameter, resulting in thresholding of the rotation rpm and/or the revolution rpm, depending on the values entered. Certain operating parameters (such as the rotation rpm or the revolution rpm) can be dynamic (e.g., vary over time) and can be encoded in the SOP file as a function of time to define a pre-determined curve. Further controllable operating parameters of superimposed revolution and rotation movements can be implemented by the mixer 10, such as the total weight of the container being mixed.

Those skilled in the art will appreciate that the reference to a "table" being used for storing records (including links/pointers to SOP files) is a conceptualization of an otherwise tangible and non-transitory medium for storing such information. In this regard, the first database 18 can implement any suitable organizational format or data structure in lieu of the SOP table 350.

Figure 3E:
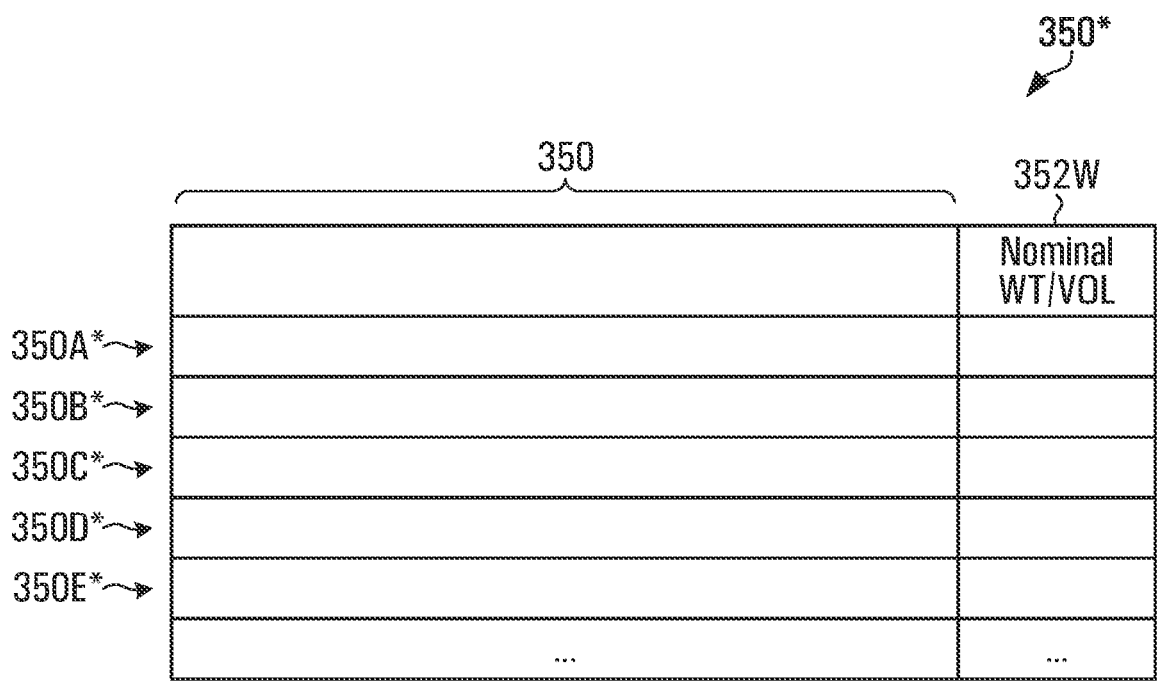
FIG. 3E illustrates an SOP table including an additional field.

Some operating procedures can require certain quantities of ingredients to be used to achieve an overall weight or volume of formulation (or range of weights/volumes). Some operating procedures can be further associated with a nominal weight/volume. FIG. 3E shows an SOP table 350* that is a variant of SOP table 350. SOP table 350* includes a plurality of records 350A* . . . 350E*. In SOP table 350*, each of the records 350A* . . . 350E* includes the same fields as SOP table 350, namely an SOP #field 352A, a mixer make/model field 352M, a functionality field 352F, a formulation property field 352P and a file field 352D. In addition, each of the records 350A* . . . 350E* in SOP table 350* includes a nominal weight/volume field 352W, which indicates the weight or volume of formulation that the respective operating procedure is specifically tailored for. There can be multiple records associated with operating procedures for which the only difference is the entry in the nominal weight/volume field.

Figure 3F:
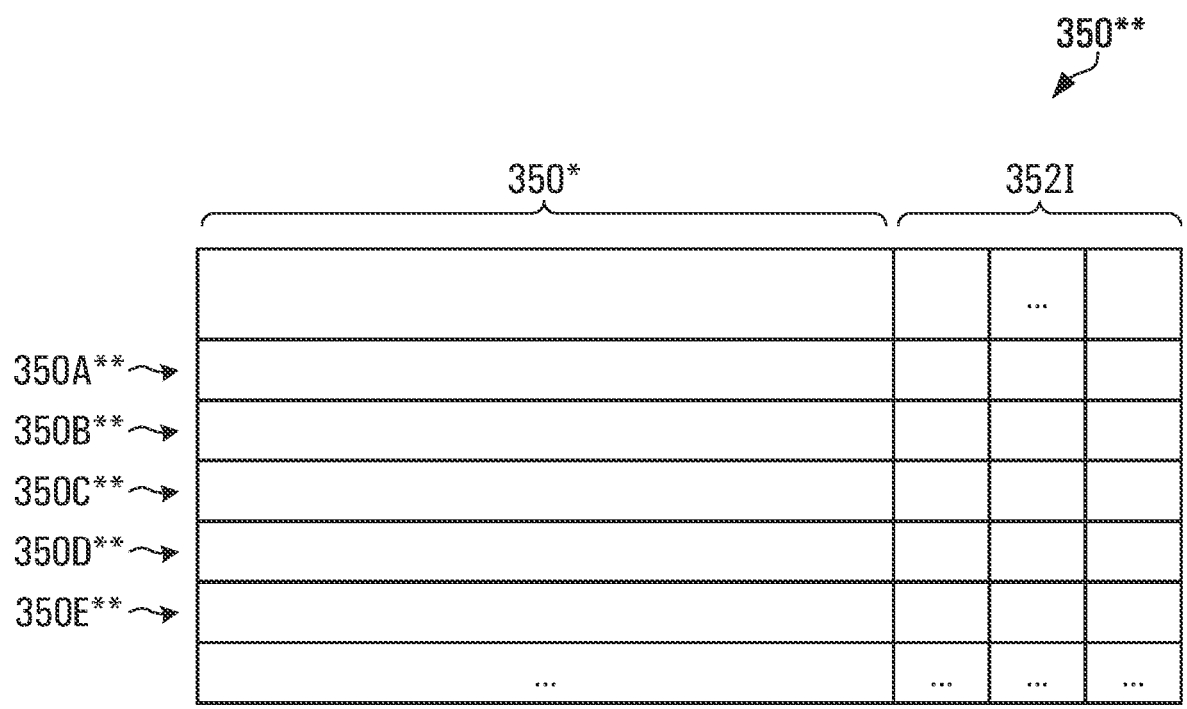
FIG. 3F illustrates an SOP table including additional fields.

FIG. 3F shows an SOP table 350 that includes records 350A . . . 350E**, each of which includes the same fields as the records in SOP table 350* of FIG. 3E. Additionally, one or more fields 352I is provided, which indicate specific quantities of ingredients associated with each associated operating procedure. These ingredients can be categorized at a coarse level (e.g., cream, base, oil, flavor, capsule, etc.) or they can be specified at a granular level or in which parts of the dispensing container the ingredients are mixed. (e.g., progesterone, size 0 EEZIFIT, size 00 CONI-SNAP #40, etc.). As increasing numbers of specialized operating procedures are developed for increasingly sophisticated versions of the interactive program module 250, it is expected that more and more granularity will be associated with the ingredients associated with each operating procedure (and stored in fields 352I of SOP table 350**).

Loading and Using SOPs with Mixers

The SOP file can include control messages executable by the mixer 10 (including a computing platform with a CPU, memory and interface to the various components of the mixer). The control messages can specify the parameters of the mixer 10 such as the rotational speeds and time of operation among others. In addition, the control messages can include user interface instructions configured to receive input from the user. The user interface instructions can include prompts that show on the mixer 10 display screen to instruct the user to perform certain functions on the mixer 10 that are specific to the selected SOP. For instance, in cases where the SOP includes several mixing steps, the user interface instructions display prompts and ask the user confirmation that certain steps have been completed, such as placement of certain ingredients in the mixer 10, before the mixer can operate.

Figure 4A:
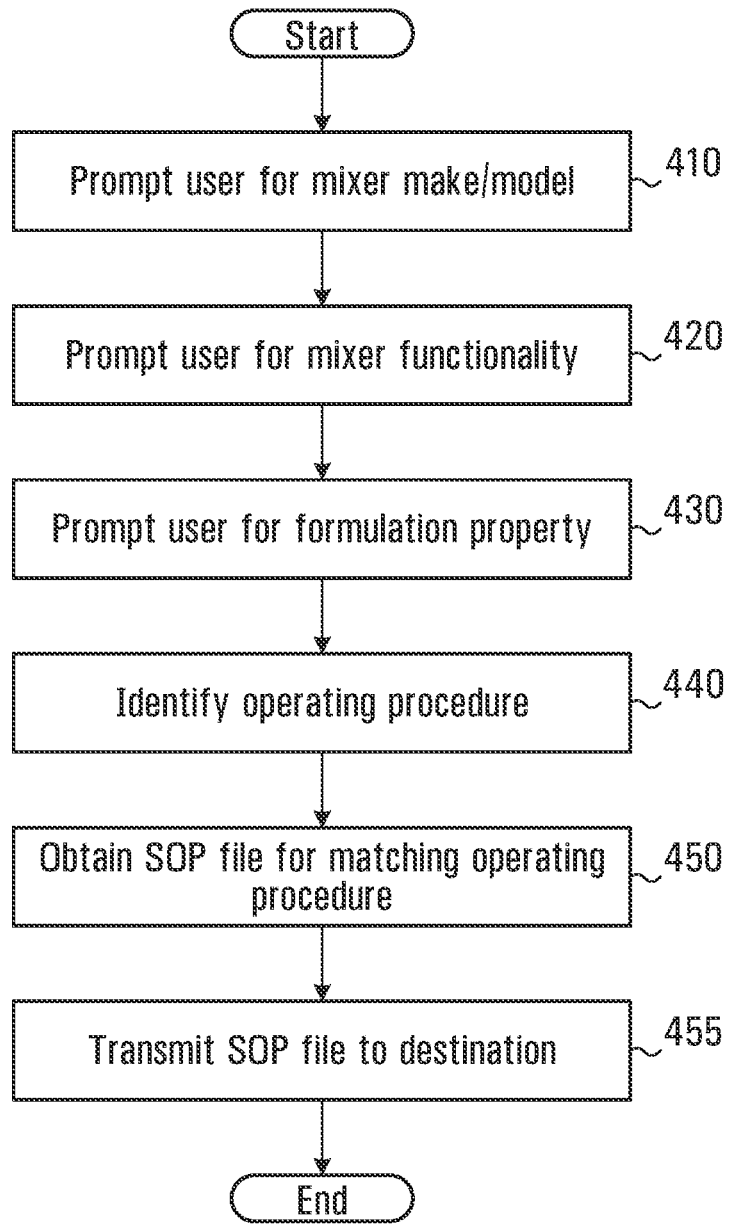
FIG. 4A is a flowchart illustrating steps that taken by an interactive program module to retrieve an operating procedure based on user input.
Figure 4B:
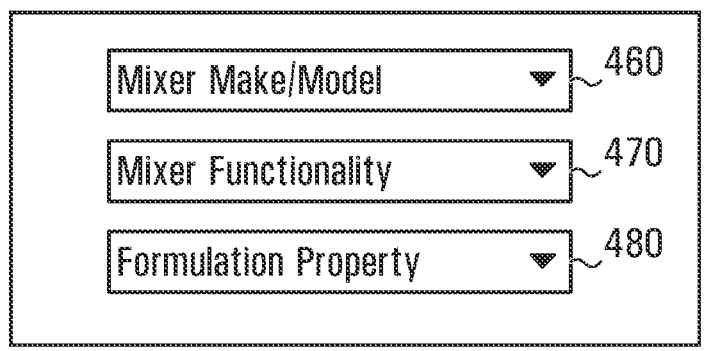
FIG. 4B illustrates a graphical user interface (GUI) on the user device that can appear during execution of the flowchart in FIG. 4A.

FIG. 4A shows a flowchart illustrative of a series of steps that can be executed by the interactive program module 250 (of FIG. 2A) once it is launched. The interactive program module 250 interacts with the user through GUI 290 presented via the user device 12, as illustrated in FIG. 4B. The user is assumed to be the rightful account holder of a user account.

At step 410, the interactive program module 250 causes the GUI 290 to display a graphical element 460 (e.g., a dialog box or menu) that presents a set of mixer make and model options, from which the user is prompted to make a selection. The set of mixer make and model options can be the set of all mixer make and model options for the various records stored in the SOP table 350.

At step 420, the interactive program module 250 causes the GUI 290 to display a graphical element 470 (e.g., a dialog box, list or graphical menu) that presents a set of mixer functionality options, from which the user is prompted to select. The set of mixer functionality options can be the set of all mixer functionality options for the various records stored in the SOP table 350, or it can be limited to only those associated with records that have matching mixer make and model as selected at step 460.

At step 430, the interactive program module 250 causes the GUI 290 to display a graphical element 480 (e.g., a dialog box, list or graphical menu) that presents a set of formulation properties, from which the user is prompted to select. The set of formulation properties presented via the GUI 290 can depend on the selected mixer functionality option. In other words, different selections of the functionality option will lead to different available selections of the formulation properties.

In this way, the user can specify a composition compounding formula (e.g., a specified list of ingredients and their relative quantities by weight, volume or concentration) with inputs through the GUI 290, which can include the mixer and model option, the mixer functionality option, and the formulation property option but is not limited thereto.

At this point in the process, the interactive program module 250 will have received various selections from the user and can have enough information to identify and obtain an SOP file. This is attempted at step 440. The interactive program module 250 can consult the SOP table 350 to identify an appropriate one of the records 350A . . . 350E that matches the user selections. Then, at step 450, the corresponding SOP file for the identified record is retrieved from memory, e.g., via the filename or pointer stored in the file field 352D for the identified record.

At step 455, the SOP file is transmitted to a destination associated with the account holder. The SOP file can be sent to the user device 12 over the data network 14 and the GUI 290 or the SOP file can be sent to an email address associated with the account holder, which could be stored in the other info field 3120 of the credentials table 310. Encryption or password protection can be used to keep the contents of the email secure.

Some steps can be performed in a different order than as illustrated in FIG. 4A.

Figure 5A:
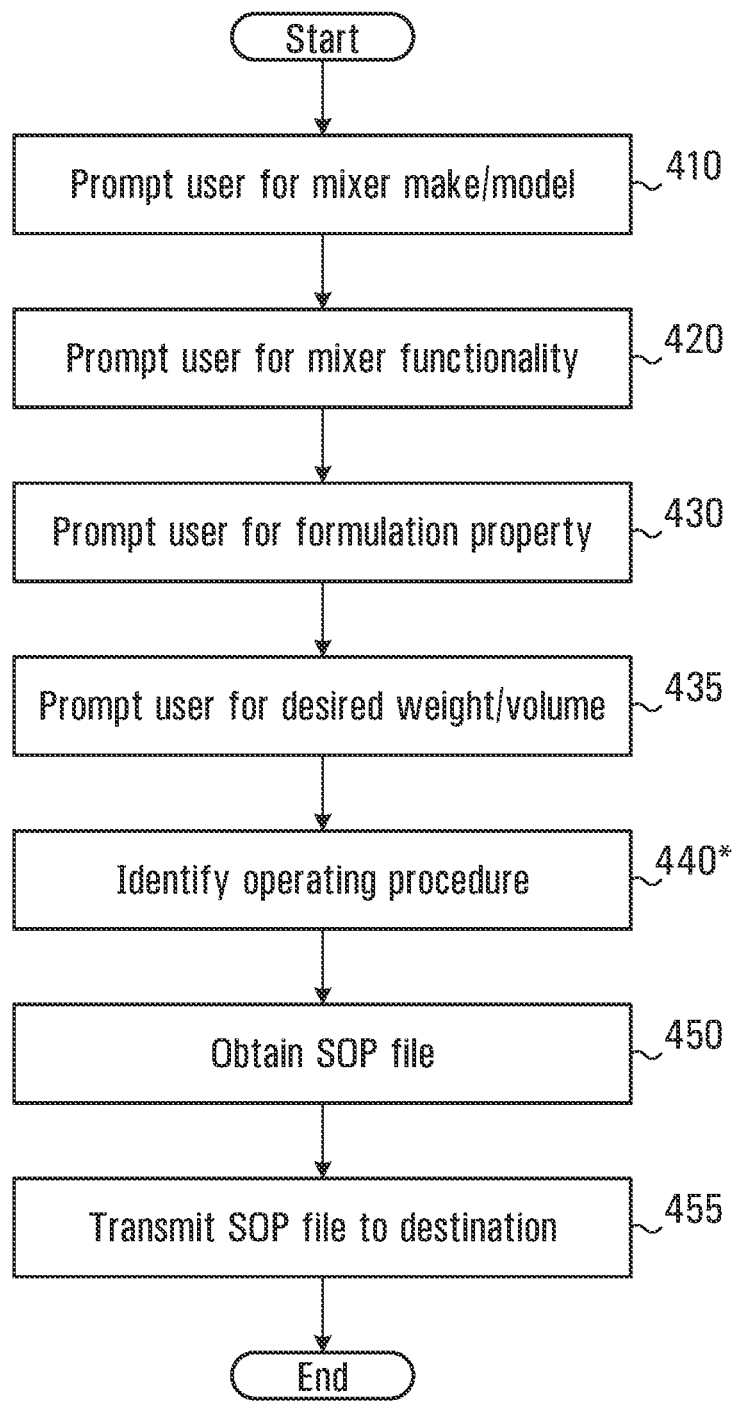
FIG. 5A is a variant of FIG. 4A with an additional step to obtain a desired weight or volume from the user.
Figure 5B:
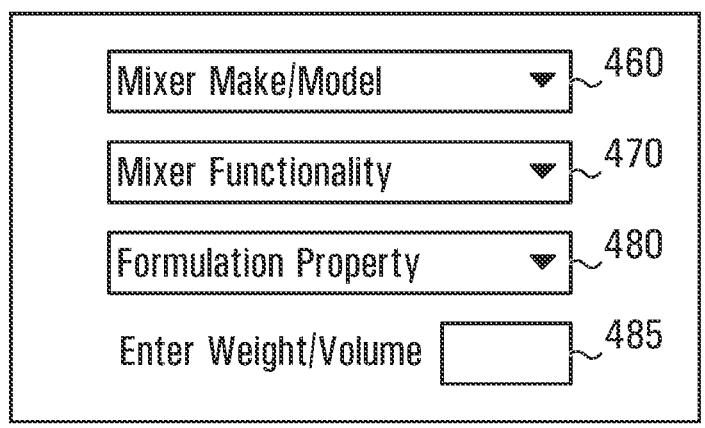
FIG. 5B illustrates a GUI on the user device that can appear during execution of the flowchart of FIG. 5A.
Figure 5C:
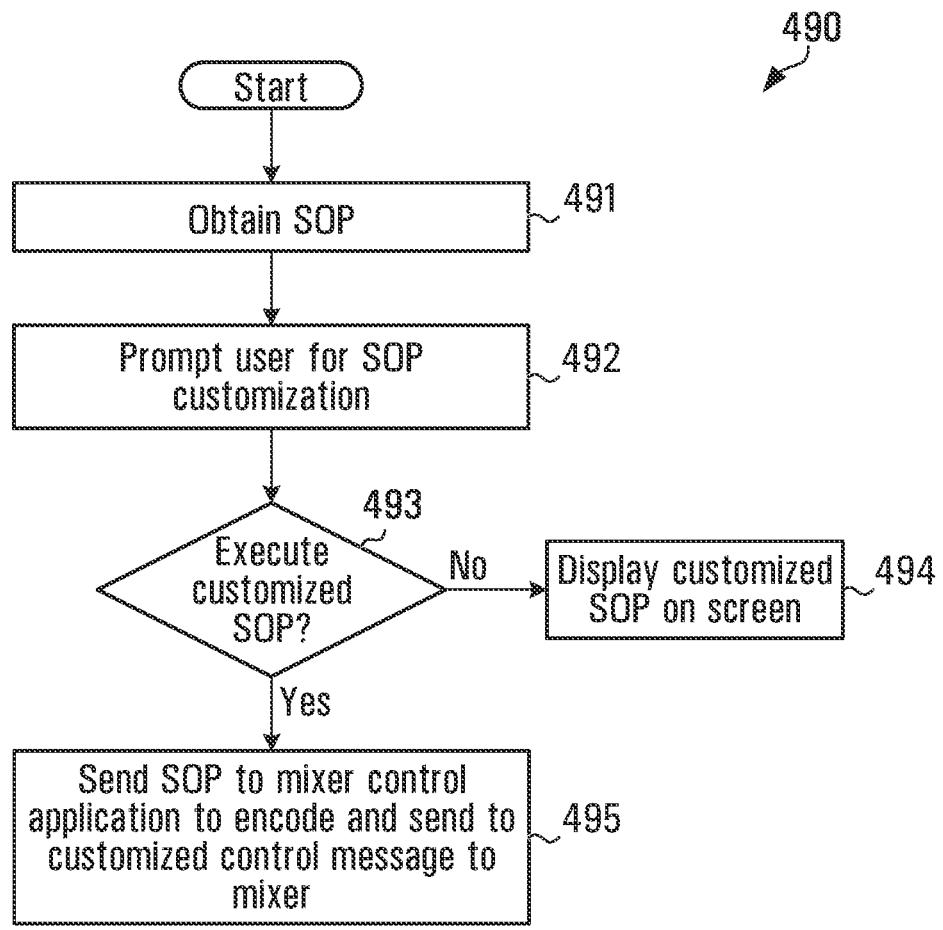
FIG. 5C is a flowchart illustrating steps that can be taken by an interactive program module to customize an SOP.

FIG. 5A is similar to FIG. 4A, but includes an additional step 435, whereby the interactive program module 250 causes the GUI 290 to display a graphical element 485 (e.g., a dialog box or menu; see FIG. 5B) that prompts the user to enter a desired weight/volume. Once the user has made all the appropriate selections via graphical elements 460, 470 and 480, including the desired weight/volume via graphical element 485, the interactive program module 250 can have enough information to obtain an actual SOP file, which is done at step 440*. The interactive program module 250 consults the SOP table 350* to identify the appropriate one of the records 350A* . . . 350E*. It should be noted that the input of the desired weight/volume affects the control messages executable by the mixer 10. For instance, a lesser volume can require less mixing time. In response to the input from the user specifying the desired weight/volume, the server 16 will customize the control messages executable by the mixer of the instructions about the machine settings in the embodiment where the setting are shown to the user and the user will program the mixer accordingly. Such customization is shown by process 490 and FIG. 5C. In this process, the user, through user device 12, obtains SOP at step 491 and based on the desired functionality and in accordance with FIG. 4A. Based on the desired weight/volume that cannot be included in the obtained SOP, the user device 12 can prompt the user at step 492 to customize the SOP to the desired weight/volume. Upon customization, the user device can decide for an action at step 493. Different actions can be taken. In one example, the user device 12 can simply display the customized SOP at step 494 for user's view only. In another example, the user can wish to run the SOP through the mixer in which case the customized SOP will be encoded to customized control messages by the mixer control application at step 495 and sent to mixer 10 for compounding.

The interactive program module 250 can restrict the desired weight/volume (as entered by the user via the graphical element 485) to only those pre-determined nominal weights/volumes of the records 350A* . . . 350E* in the SOP table 350*. This guarantees that obtaining the SOP file at step 440* involves a match between the desired weight/volume and the information in the nominal weight/volume field 352W of a one of the records 350A* . . . 350E*.

However, in some cases, the desired weight/volume entered by the user via the graphical element 485 may not correspond to the nominal weight/volume of one of the operating procedures in the SOP table 350*. In this case, the interactive program module 250 can carry out a comparison to identify the record with the closest matching nominal weight/volume to the desired weight/volume, and to retrieve the corresponding SOP file from memory. Alternatively, the interactive program module 250 can be configured to generate a customized SOP file based on the desired weight/volume and the nominal weight/volume. The customized SOP file can include scaled or interpolated quantities for the weight or volume of the ingredients used as well as the operating parameters (e.g., rotation speed, revolution speed, time, etc.). A table stored in the memory 220 can include conversions between operating parameters for different weights and volumes of a formulation. In this regard, further information on the formulaic generation of operating procedures can be found in U.S. patent application Ser. No. 15/809,636, filed Nov. 10, 2017, which is hereby incorporated by reference herein.

Figure 6:
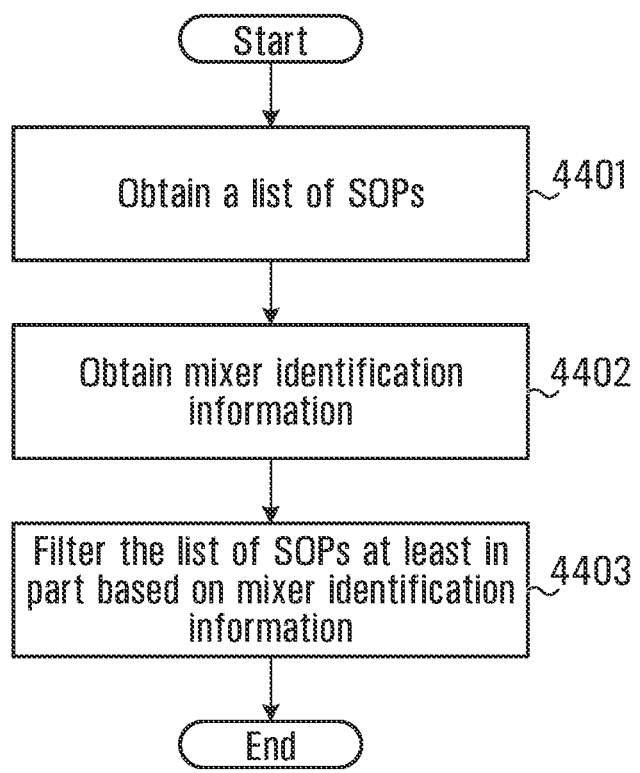
FIG. 6 is a flowchart illustrating a method of using an SOP.

Referring to FIG. 6, the SOPs made available to the user can be filtered based on the capabilities of the mixer 10. For instance, the database 18 can include a list of SOPs, some of which are compatible only with certain mixers. To avoid sending the user wrong SOP information, the first server 16 will first obtain a list of available SOPs at step 4401 and subsequently obtain mixer identification information at step 4402. The first server 16 after obtaining the mixer identification information can filter the SOPs at step 4403 based on the mixer 10 identification information such that the information received by the user would work with the mixer 10 the user has. The order of steps 4401 and 4402 can be reversed. For example, the first server 16 can obtain mixer identification information first and then obtain all available SOPs which will subsequently become filtered based on the mixer identification information. This filtering is useful in instances where in addition to the SOP, the first server 16 also sends mixer programming information, specifying the mixer settings to implement an SOP. The mixer programming information can be displayed on the user device 12 or can be sent as machine parameters directly to the memory of the mixer 10. In the former case, the user would need to set the various controls of the mixer according to the settings displayed on the user device 12. In the latter case the mixer 10 is automatically programmed as required for the SOP.

The mixer 10 can communicate via the data network 14 with the first server 16, second server 17, first database 18, and second database 19 to execute various user-assistance programs. These programs can include differing levels of interaction.

Figure 7:
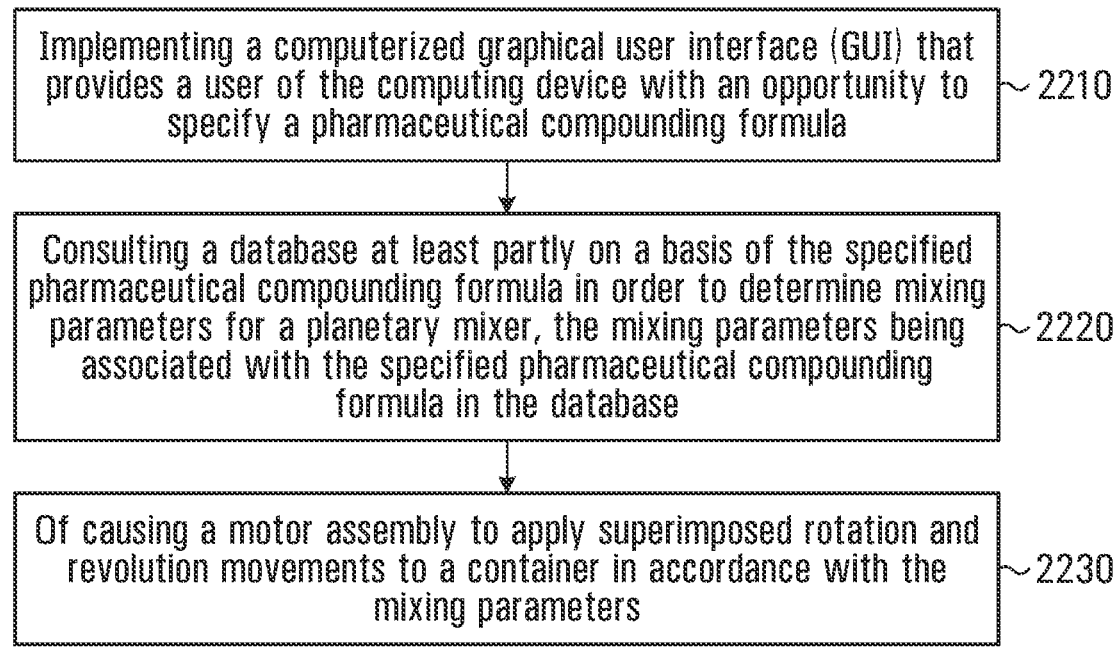
FIGS. 7-9 show various methods.

FIG. 7 shows a computer-implemented method for execution by a processor of a computing device such as processor 10 (FIG. 2A) and includes a step 2210 where a GUI functional block of code implements a GUI such as GUI 290 that provides the user of the computing device with an opportunity to specify a composition compounding formula. The composition compounding formula can be a pharmaceutical composition or a skin-care composition. The GUI functional block can be part of the interactive program module 250.

Step 2220 includes consulting a database arrangement such as database 18 and database 19 at least partly on a basis of the composition compounding formula specified in step 2210. The database in consulted to determine mixing parameters for a planetary mixer, the mixing parameters being associated with the specified composition compounding formula in the database.

The method also includes a step 2230 of causing a motor assembly to apply superimposed rotation and revolution movements to a container in accordance with the mixing parameters determined from step 2220.

Figure 8:
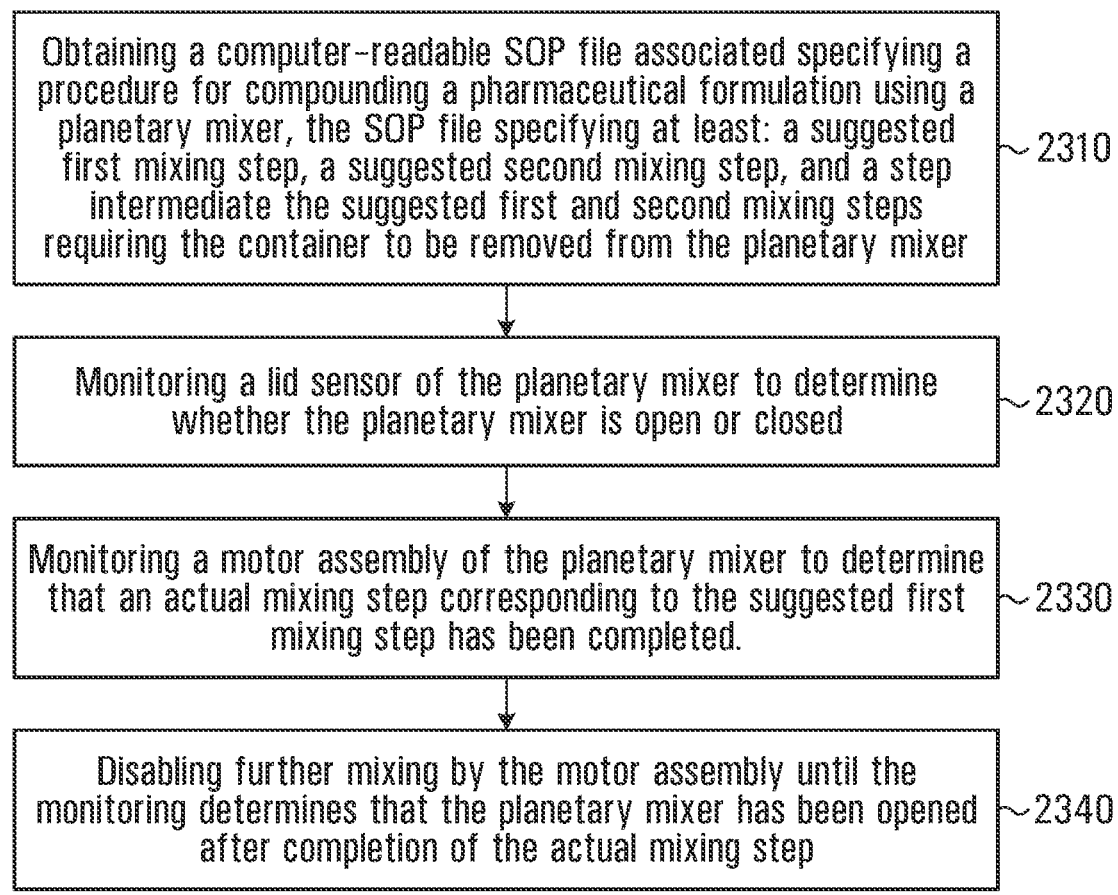

FIG. 8 shows a computer-implemented method for compounding using a planetary mixer, which includes a step 2310 of obtaining a computer-readable SOP file associated specifying a procedure for compounding a pharmaceutical formulation using a planetary mixer, the SOP file specifying at least: a suggested first mixing step, a suggested second mixing step, and a step intermediate the suggested first and second mixing steps requiring the container to be removed from the planetary mixer. The method also includes a step 2320 of monitoring a lid sensor of the planetary mixer to determine whether the planetary mixer is open or closed. The method further includes a step 2330 of monitoring a motor assembly of the planetary mixer to determine that an actual mixing step corresponding to the suggested first mixing step has been completed. Finally, the method includes a step 2340 of disabling further mixing by the motor assembly until the monitoring determines that the planetary mixer has been opened after completion of the actual mixing step.

Figure 9:
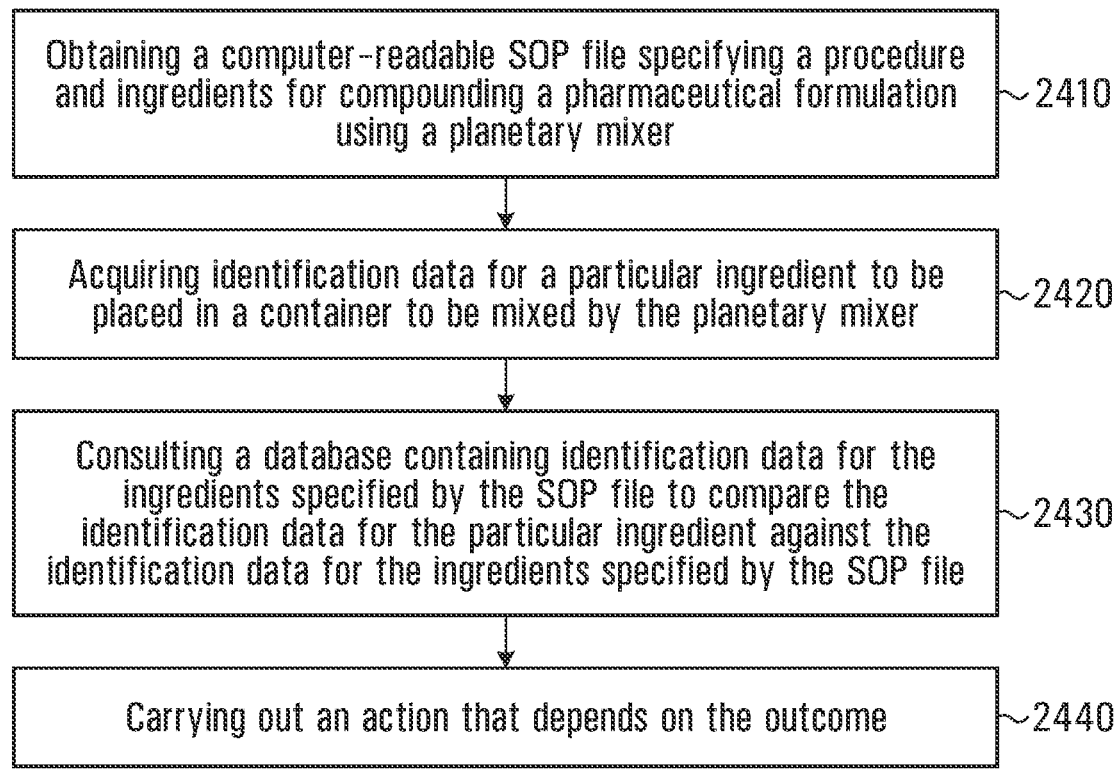

Referring to FIG. 9, a computer-implemented method includes a step 2410 of obtaining a computer-readable SOP file specifying a procedure and ingredients for compounding a pharmaceutical formulation using a planetary mixer. The method also includes a step 2420 of acquiring identification data for an ingredient to be placed in a container to be mixed by the planetary mixer as well as a step 2430 of consulting a database containing identification data for the ingredients specified by the SOP file to compare the identification data for the ingredient against the identification data for the ingredients specified by the SOP file. Step 2420 can be carried out by an ingredient validation functional block of code that validates ingredients are they are presented by a user. At step 2420, the ingredient functional block of code includes instructions for consulting a database such as database 18 and database 19 at least partly on a basis of the procedure specified in step 2410. The database is consulted to determine mixing parameters for a planetary mixer, the mixing parameters being associated with the specified composition compounding formula in the database. Step 2420 can include receiving a code generated by a code-reader (described in more detail below) when reading machine-readable data applied on a container holding a first ingredient. The code conveys one or more characteristics of the first ingredient. The database is consulted at least in part on the basis of the compounding formula specified in step 2210 to derive a formulation ingredient to be used in preparing the specified composition. The ingredient functional block determines at least in part on the basis of the code if the first ingredient matches the formulation ingredient.

Finally, the method of FIG. 9 includes a step 2440 of carrying out an action that depends on the outcome of step 2430. This step is carried out by a planetary mixer control functional block of code that configured for consulting the database at least partly on a basis of the specified compounding formula to determine mixing parameters for a planetary mixer, the mixing parameters being associated with the specified compounding formula. The planetary mixer control functional block of code, following step 2430, can cause a motor assembly of the planetary mixer to apply superimposed rotation and revolution movements to a container in accordance with the mixing parameters determined from the consulting. In the event that the determining step fails to match the first ingredient to the formulation ingredient, the action that is carried out is that the planetary mixer control functional block prevents operation of the motor assembly.

In any of the methods, once the mixer 10 has finished the mixing operation defined by the operating parameters entered into the mixer 10 in one of the above ways, the mixer 10 can be configured to send a completion message to the mixer control application 120 over the wired or wireless connection. In this way, the mixer control application 120 is alerted that mixing has terminated. In embodiments where the mixer 10 is connected to the data network 14, the user can carry the user device 12 into another room or facility and to be alerted, over the data network, that the mixing operation has finished. The completion message can be in the form of an email or text message or other visual or auditive cue.

The method steps of FIG. 7 to FIG. 8 can be carried out alone, in combination, or repeated. For example, the ingredient validation functional block that carries out step 2420 of FIG. 9 can configured for receiving a second code or a plurality of codes that are sequentially input by the code reader as the code reader sequentially reads machine-readable data on a plurality of containers holding respective ingredients, wherein each code conveys one or more characteristics of the respective ingredient. The method can go on to consulting the database arrangement at least in part on the basis of the compounding formula to derive a plurality of formulation ingredients to be used in preparing the composition, and determining at least in part on the basis of the codes if the ingredients held in the plurality of containers match the formulation ingredients. The planetary mixer control functional block can be configured to prevent operation of the motor assembly when the determining step fails to match all the codes to the formulation ingredients, as the action that is carried out in step 2440.

The GUI functional block associated with step 2210 of FIG. 7 can be responsive to the ingredient validation functional block to display an error message on the GUI when it is determined that there is a failure to match the code to the formulation ingredient. The error message can indicate that the ingredient held in the container is incorrect for the specified compounding formula.

Figure 10:
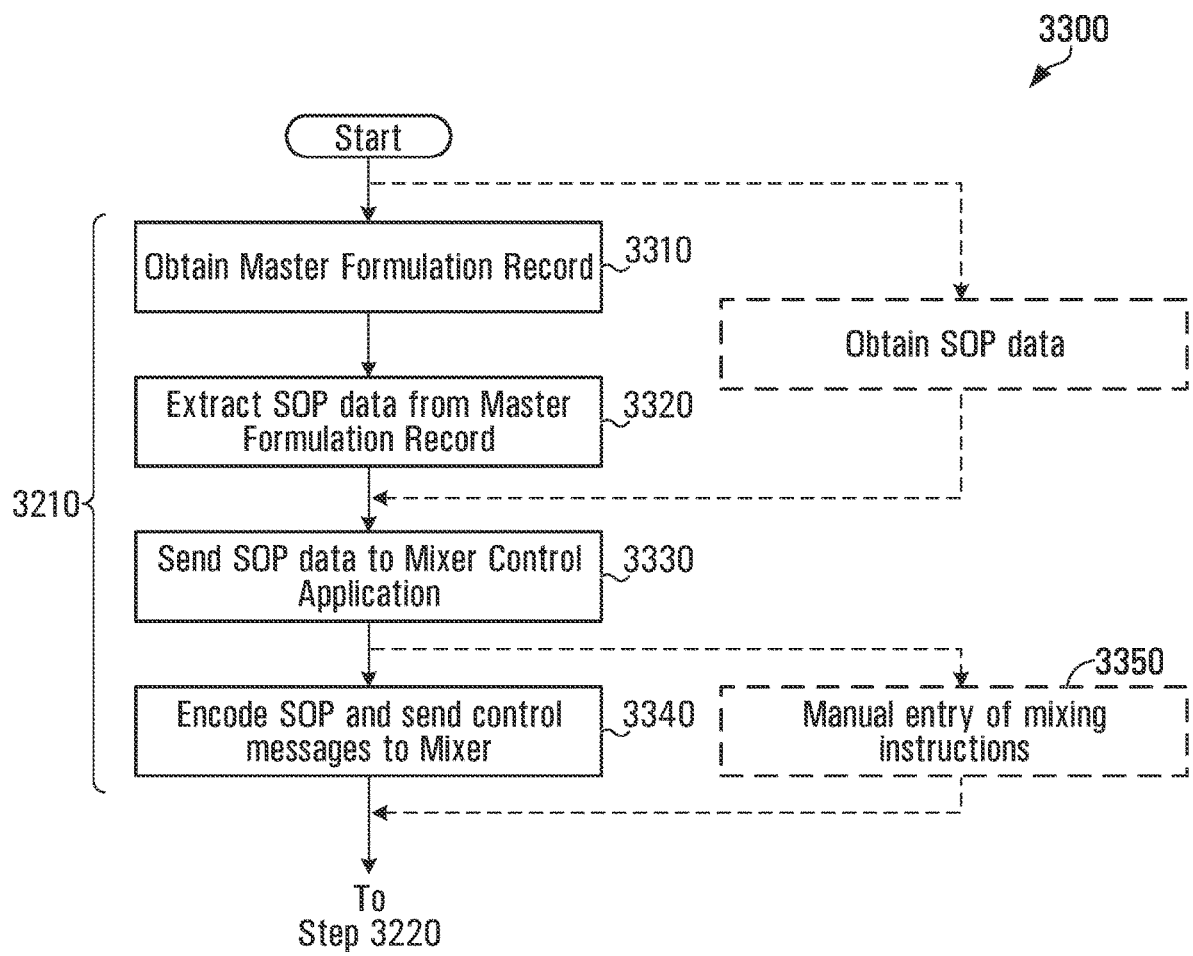
FIG. 10 is a flowchart of a process for generating regulatory records.

FIG. 10 shows the interactive program module 250 of the mixer 10 configured to obtain and transmit compounding information which are in different forms and contents. In one example, the compounding information can be in forms of an SOP file. SOP can include an ordered set of process steps for operating the mixer 10 for a specified composition using a specific make and model of planetary mixer under certain functionalities. Examples of SOPs are shown in FIGS. 3C and 3D. In one example, SOPs can reside on a database at a pharmacy server and can vary from one pharmacy to another. In another example, SOPs can reside on a remote server and can be accessed from multiple user devices 12 from different pharmacies.

Still referring to FIG. 10, an SOP transmitted to a requesting device, such as the user device 12, can itself originate from a Master Formulation Record (MFR). MFRs can also be computer-readable digital or electronic and are further comprehensive sources of information that not only contain the information within a standard operating procedures (SOPs) to compound a composition, but also contain information above and beyond the compounding process. Information within MFRs can include:

- Name, dosage and physical form of the compounded composition
- Expected yield
- Summarized and/or detailed calculations to determine quantities for active pharmaceutical ingredient (API), excipients, etc.,
- Summarized and/or detailed description of all ingredients, the quantity of each ingredient, source of each ingredient, their lot number, compatibility and stability info and expiry date
- Compatibility and stability data, including references when available
- References used to develop the formula and the consultation date, as appropriate
- Equipment needed to compound the preparation (and any special cleaning instructions)
- Special precautions to be observed by compounding personnel
- Instructions for mixing; e.g., the order of mixing, mixing temperatures, mixing speeds, duration, etc.
- Information on labelling; a list of instructions can be name of composition, dosage, beyond-use-date (BUD), to-be-stored conditions, prescription number corresponding to the formulation
- Description of final preparation
- Container type to be used in dispensing
- QA/QC procedures.

In one example, MFRs are a combination of computer-readable files residing on a database at a pharmacy server and can vary from one pharmacy to another. In another example, MFRs can reside on a remote server in unified format and can be accessed from multiple user devices 12 from different pharmacies. A user through user device 12 can interact with server to access the MFR database. In one example, once the communication is established between server and the user device 12, the user device can obtain a copy of the MFR on the user device memory.

SOPs and MFRs can be created for the first time and upon adding a new composition to be compounded. In one example, SOPs and MFRs could be created for the first time from external resources including Trissel's Stability of Compounded Formulations, Trissel's Handbook of Injectable Drugs, AHFS Drug Information, United States Pharmacopeia, Remington: The Science and Practice of Pharmacy, USP Dispensing Information, Journal of Pharmaceutical Sciences, American Journal of Health-System Pharmacy and International Journal of Pharmaceutical Compounding. Once new SOPs and MFRs are created, they can be stored on SOP databases or MFR databases and transmitted to a user device 12 and further encoded for prospective compounding processes.

MFRs could be the upstream source of information for generating SOPs. In other words, SOPs can be directly extracted from an MFR and subsequently transmitted to a user device 12. FIG. 10 illustrates obtaining composition preparation information. The user device 12 can interact with the MFR database to retrieve an existing MFR. The mixer control application 120 running on the user device 12 can further parse the information on MFR to extract the information to be included in an SOP. Regardless of the presence or absence of MFRs, SOPs can be consulted directly and retrieved by the user device 12. The mixer control application 120 can then encode the SOP into control messages and send them to mixer 10. In an optional alternative, the SOP is not encoded by the mixer control application 120, but rather its instructions are manually input by the user into the mixer 10. In some scenarios, existing MFRs can become partially modified. Reasons for such modifications can be a change in dosage (that is not covered by the existing MFR), a change in at least one ingredient (due to replacing an allergenic or prohibited ingredient with an alternative ingredient), updating mixing instructions (due to changes in compounded volume/weight) or any other reason known to a skilled person.

Figure 11:
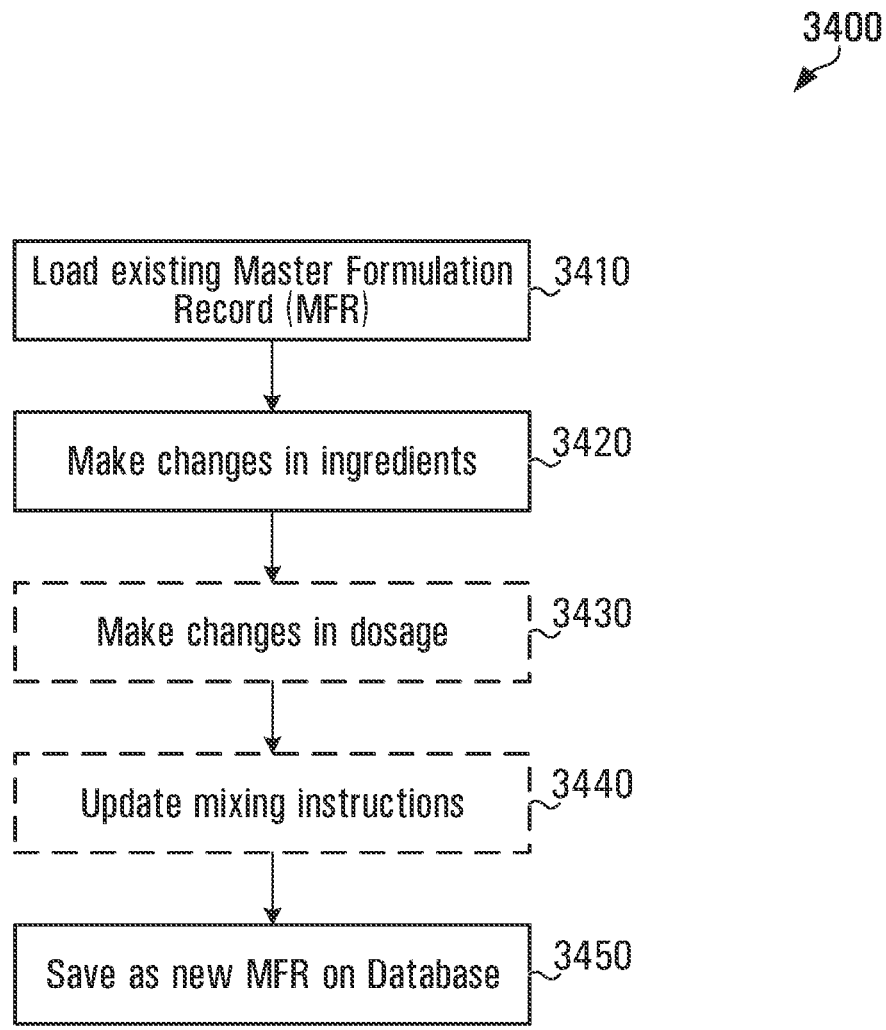
FIG. 11 is a flowchart of a process for creating a master formulation record.

Referring to FIG. 11, the user device 12 can interact with the MFR database to retrieve an existing MFR. The retrieved MFR can be further modified to replace at least one ingredient. In another example, the MFR can be optionally modified to change the compound dosage of active ingredient. In another example, the MFR can be further optionally modified to change the mixing instructions. Once modifications are completed, the user device 12 can save a new copy of the MFR that corresponds to new compound dosage and replaced ingredients. Subsequently, SOPs corresponding to the new MFR could be extracted using mixer control application 120 running on the user device 12.

Figure 12:
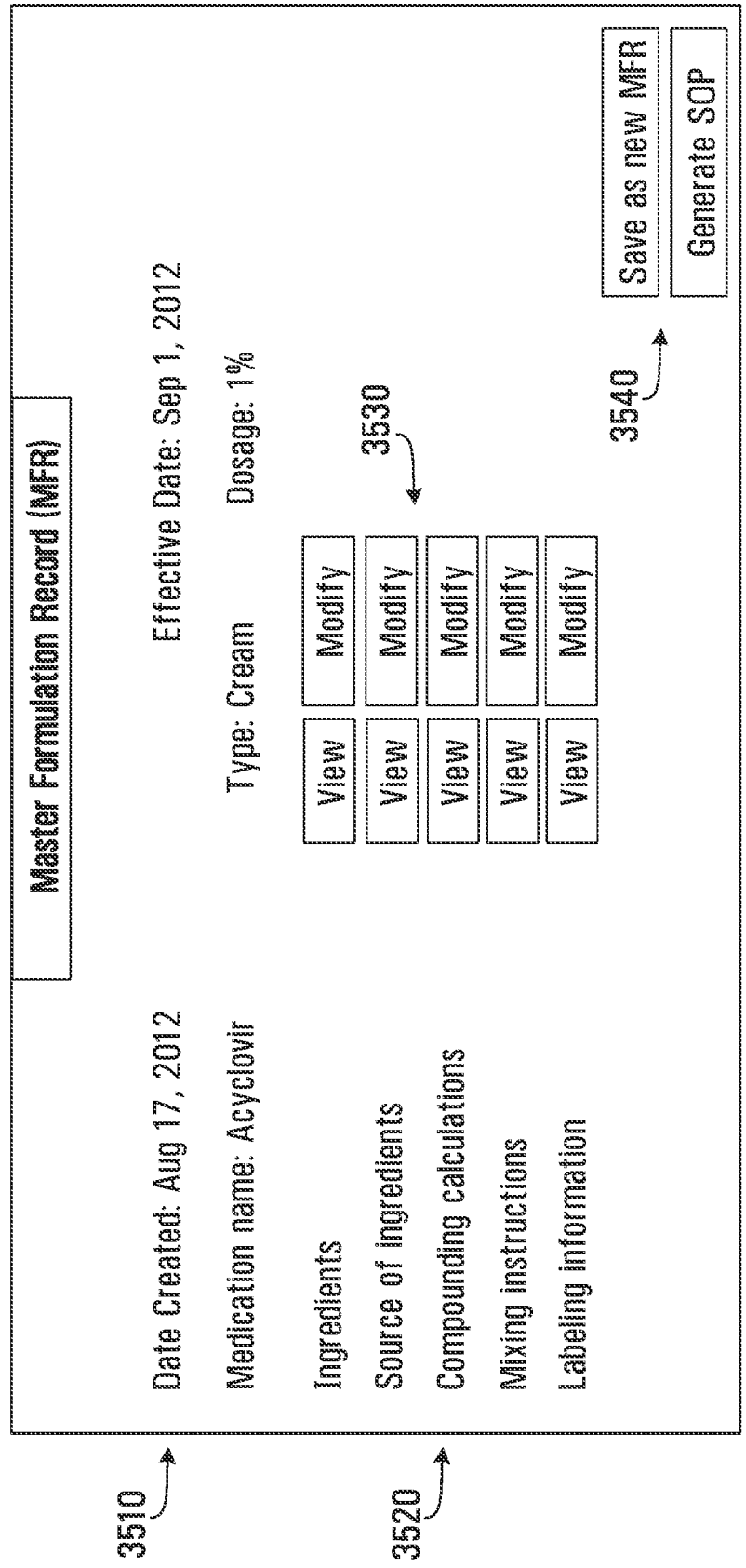
FIG. 12 illustrates a GUI on the user device that can appear during execution of the flowchart of FIG. 11.

FIG. 12 is an illustration of an MFR from a GUI perspective. Users can interact with MFR in several ways. In one example, elements of master formulation record (including ingredients, source of ingredients, compounding calculations, mixing instruction and labeling information) could be viewed. In another example, elements of master formulation record can be both viewed and modified. Users in this case can be able to save the modified MFR as a new record.

Verifying User Correctly Carrying Out SOP Steps

In some embodiments, the interactive program module 250 can reduce the occurrence of errors in the carrying out of an operating procedure. Instead of only supplying an SOP file to a requestor, the interactive program module 250 can be configured to require confirmation that the various steps in the SOP file are being performed correctly. For example, the interactive program module 250 can be configured to compare the operating parameters used actually and the operating parameters suggested by the SOP file, and taking an action, such as issuing an alarm, that depends on a result of the comparison. In a simple example, the interactive program module 250 can be configured to signal an alarm if a threshold amount of time has elapsed between steps. Such an alarm can be a visual alarm and/or auditory signal sent via a user interface of the mixer 10. In some cases, where the mixer 10 is a stand-alone device, the interactive program module 250 has no way of knowing whether the user has complied with any of the individual process steps of the SOP file. However, if the mixer 10 is connected to the first server 16 (e.g., via the data network 14, or via the mixer control application 120 running on the user device 12), the interactive program module 250 can have access to monitoring messages from the mixer 10. These monitoring messages can indicate the status of the mixer 10, whether the lid is open or closed, the values of the operating parameters being supplied to the mixer 10 and so on. This allows the interactive program module 250 to corroborate whether the steps in the SOP file have been correctly performed, which can potentially reduce errors.

For example, one of the process steps in the SOP file can require the user to remove the container from the mixer 10 to perform some action, such as add a wetting agent or further ingredient, and then to return the container to the mixer 10. In this case, based on monitoring messages received from the mixer 10, monitoring the state of the lid would allow the interactive program module 250 to determine whether this process step was being correctly followed.

The interaction carried out by the interactive program module 250 can also be carried out by the mixer control application 120 running on the user device 12, provided that the SOP file has been obtained and stored in memory.

Validating Ingredients Added

The systems and methods described herein help avoid human error by keeping track of which ingredients are added to a container when a mixture is being compounded. In some embodiments, the mixer control application 120 can be configured to validate collected data before authorizing the mixer 10 to start.

For example, it is possible to explicitly track the ingredients being added to a container to gain improved quality control and/or business insight. Many ingredients approved for use in a pharmacy setting are associated with a unique CAS number (a unique numerical identifier assigned by the Chemical Abstracts Service (CAS) to every chemical substance described in the open scientific literature). CAS numbers can appear on the bottles and containers of the various ingredients to be used in creating the formulation of choice. The CAS numbers can be encoded in a bar code or QR (quick response) code on the various ingredient containers. In some embodiments, ingredient containers can be identified by electronic tags.

Figure 13:
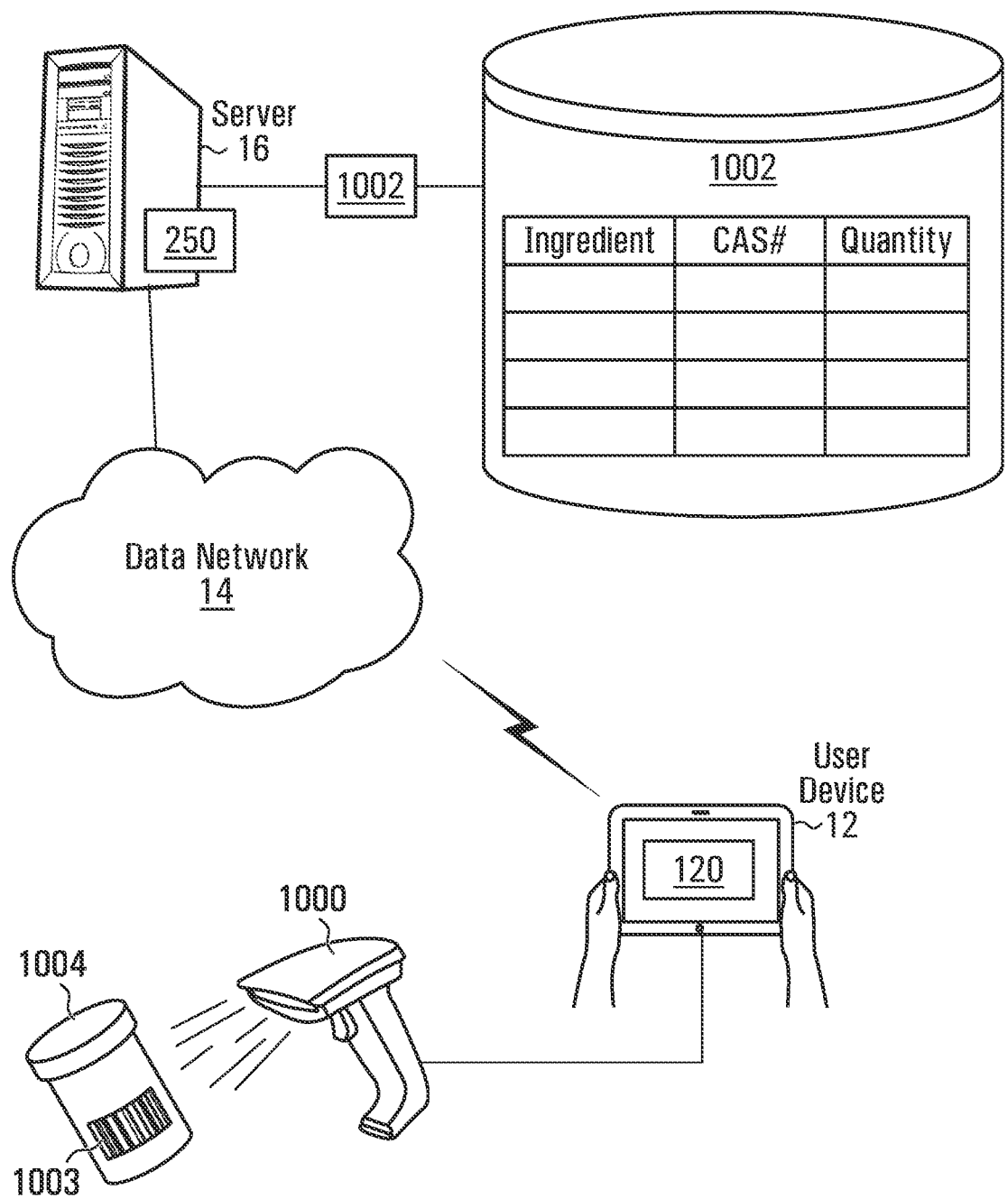
FIG. 13 is a diagram showing entities participating in a validation process.

Referring to FIG. 13, a data entry device 1000 (e.g., a keyboard, scanner such as a bar code scanner) is connected to the user device 12 running the mixer control application 120. The data entry device 1000 can be used to input or acquire the CAS number of an ingredient that a user is adding to the container in which mixing is to occur. This can be done by scanning an optical code such as a bar code or QR code 1003 in a region of a container 1004 containing the ingredient. It is assumed that the mixer control application 120 has obtained a SOP file (e.g., from the interactive program module 250) specifying or encoding a plurality of process steps, at least one of which involves mixing certain ingredients in certain proportions. The SOP file lists one or more ingredients. In addition, the mixer control application 120 has access to a database 1002 of CAS numbers associated with various possible ingredients, including those in the SOP file. Access to the database 1002 can be provided over the data network 14.

Figure 14:
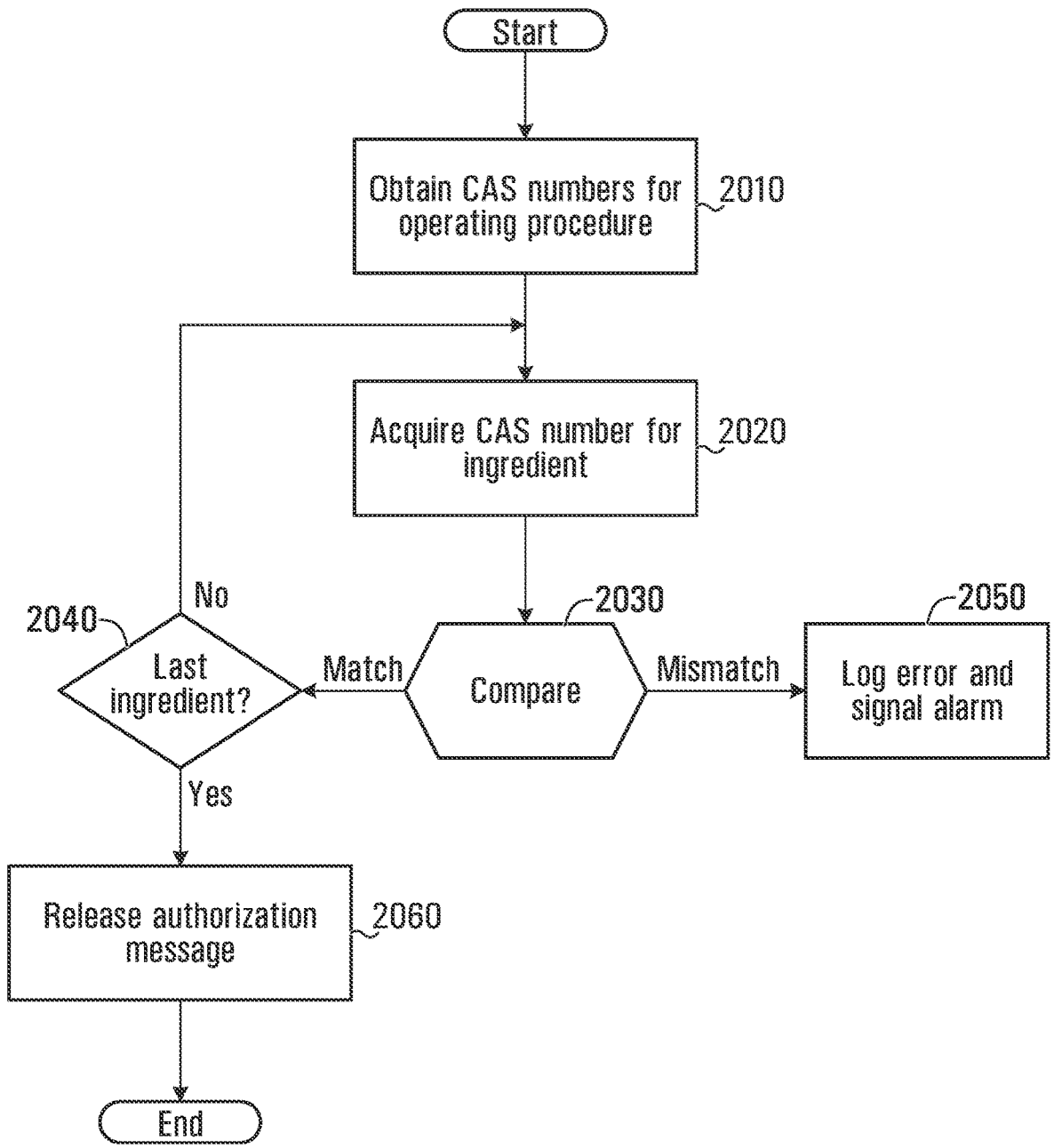
FIG. 14 is a flowchart showing steps in a validation process.

FIG. 14 shows the steps the mixer control application 120 executes to validate an ingredient. In some instances, the mixer control application 120 can be configured to disable the mixer 10 from mixing until the validation process has successfully completed.

In an initialization step 2010 the mixer control application 120 contacts the database 1002 to obtain the CAS numbers of the ingredients associated with a desired (e.g., a loaded) SOP file. At step 2020 ingredient data is acquired by the data entry device 1000. This can be a CAS number or image data that encodes a CAS numbers. At step 2030, the validation process compares the acquired CAS number to the CAS numbers of the ingredients associated with the SOP file. At this point, the validation process carries out an action that depends on the result of the comparing. For example, if there is a match, then the next step could be step 2040. If there is a mismatch, e.g., one of the acquired CAS numbers does not match any of the CAS numbers for the ingredients listed in the SOP file, then the validation process may, at step 2050, log the error and also to signal an alarm in real-time, in the form of a message, audible or visual cue. This can immediately alert the preparer of the formulation that there is a problem, potentially resulting in less wastage of time and material resources. An optional step (not shown) can check to determine whether the CAS number has been duplicately scanned and, if so, to issue an alarm.

At step 2040, the validation process determines whether the acquired CAS number corresponds to the last ingredient that needed to be scanned for the selected SOP file. If so, the mixer control application 120 may, at step 2060, enable the mixer 10 to authorize it to commence mixing. This can be done my sending an authorization message to the mixer 10. Mixing can occur using operating parameters provided as part of the SOP file by the mixer control application 120 or by the user directly via the user interface 850 of the mixer 10. Until the authorization message is received by the mixer 10, further mixing can be blocked (e.g., the mixing functionality of the mixer 10 can be disabled). This can also improve the reliability of the compounding process. The mixer 10 can override the blocking imposed on it by the mixer control application 120. For example, the mixer 10 can recognize a code. By entering the code via the user interface 850, the user can forcibly bypass any warnings issued by the mixer control application 120.

When the user enters a formulation that he/she wishes to create, the validation process can be used as one additional check to ensure that the correct ingredients are being added to the mixture. The CAS-based system is manufacturer-agnostic, as it is expected that all products will have a CAS number. In other cases, ingredients can also have a manufacturer-specific code, such as a bar code or QR code. As ingredients are being added, the scanner can be used to scan the bar/QR code, which is then sent to the first server 16, allowing the entity that owns/manages the first server 16 to keep track of which pharmacies use how much of which ingredients sourced by which manufacturers. This information is valuable as it could allow the entity that owns/manages the first server 16 to develop a sales strategy.

Figure 15:
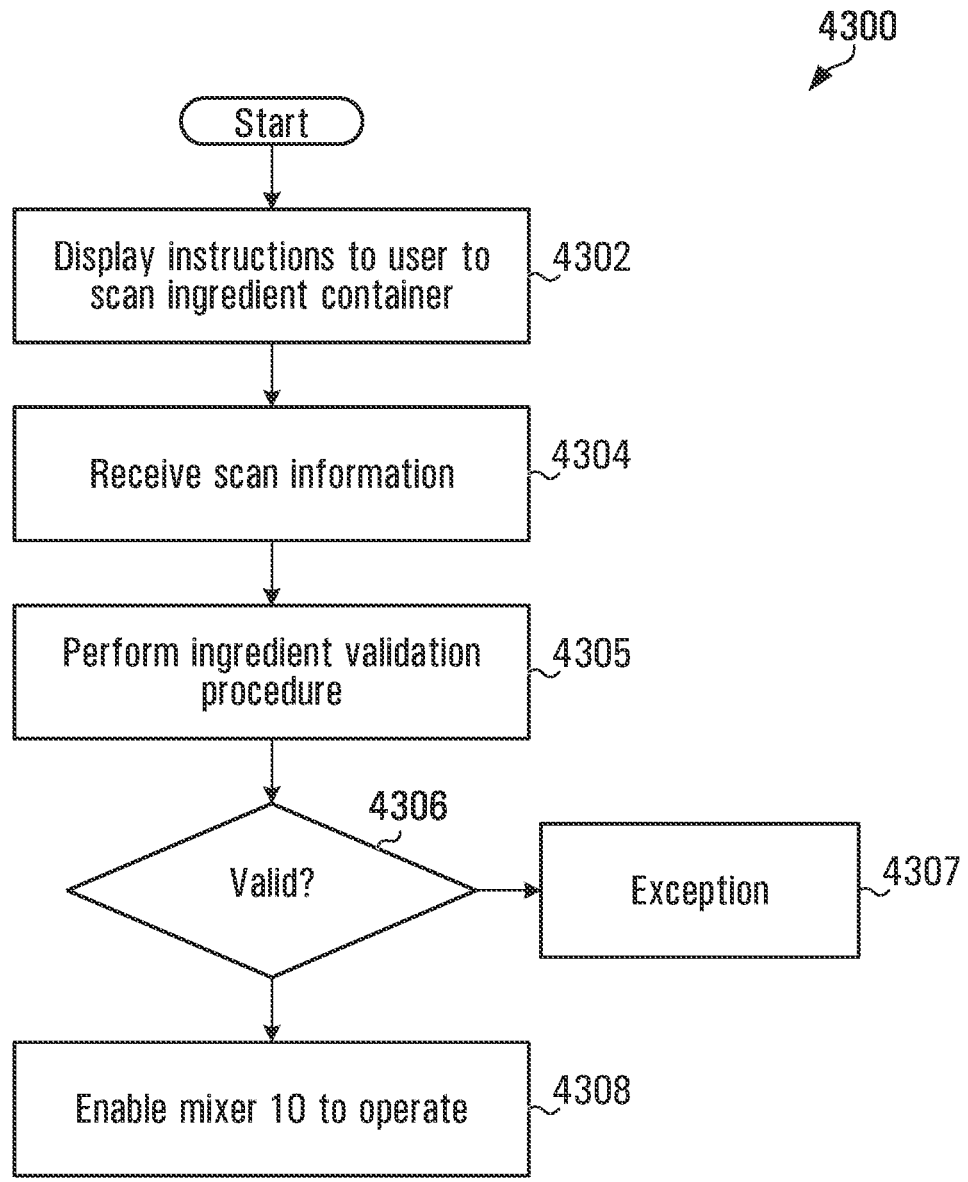
FIG. 15 is a flowchart of a process for executing the one-click refill.

FIG. 15 shows a process that conditions the services provided by the first server 16 to the user upon a validation of the ingredients specified in a SOP. After the process 4300 starts in a first step (it is assumed that the user has properly logged in his/her account and has selected an SOP to produce the desired composition), at step 4302 the first server 16 sends SOP instructions or mixer command signals to guide the user in preparing the formulation. One such instruction can include, for example, requesting the user to obtain a certain quantity of ingredient #1. The instructions can be displayed on the user device 12 indicating to the user the ingredient and the quantity thereof to be prepared. The instructions can also indicate to the user to provide ingredient identification information to validate the ingredient. The ingredient identification information can be provided via a data reading device such as the data reader 1000. In FIG. 13, the data reading device is a bar-code reader that reads the bar code 1003 on the container 1004 of ingredient #1. The ingredient identification information so scanned is uploaded to the first server 16 at step 4304. Alternatively, the ingredient identification information can also be entered manually, if the user is not equipped with a data reader 1000.

The manual data entry can be accomplished by the user typing on the user device 12 the ingredient identification information appearing on the label of the container 1004. The ingredient identification information thus received by the first server 16 is subjected to a validation procedure at step 4305. The purpose of the validation procedure, generally, is to reduce the possibility of human errors due to the use of incorrect ingredients. The validation procedure involves one or more of the following.

The validation procedure can involve a comparison of the ingredient identification information against a database of genuine ingredients to detect counterfeit ingredients. The database is part of the first server 16 and records the ingredient identification information at the time of manufacture and distribution of the container 10. So, if the user has obtained inadvertently a counterfeit ingredient, there would be no match with the database, which would trigger an exception at step 4307.

The validation procedure can also ensure the correct ingredient is used. The system logic identifies through the ingredient identification information the ingredient and compares it what the user has been asked to provide at step 4302. If there is no match, an exception is then triggered at step 4307.

The validation procedure can also ensure compliance with the expiry date of the ingredient. Through the ingredient identification information, the expiry date of the ingredient in that container is extracted from the database and the logic determines if the ingredient can still be used. In this fashion, expired ingredients will also trigger an exception at step 4307.

If no exception has been triggered at step 4307, as determined by decision step 4306, the process flow loops back to step 4302, where the instructions for the SOP are incremented, and can include the instructions for the operator to provide a quantity of ingredient #2 (whether the operator is human or robotic). The logic then performs steps 4304, 4305 and 4306 in relation to ingredient #2. This loop repeats for each instruction that requires the operator to provide an ingredient.

If an exception is triggered at 4307, the execution of the SOP is interrupted to prevent the operator from preparing an incorrect composition. Step 4307 can involve help instructions to allow the user to correct the situation. If the operator has input or failed to provide as requested the ingredient identification information, an error message is displayed on the user device 12 to indicate that no record of the ingredient has been found and a request is made to the operator to enter a valid ingredient identification. At this point the operator can obtain another container of the requested ingredient, enter the ingredient identification information and if the ingredient is validated the process resumes.

If the exception is the result of an operator scanning or entering an ingredient identification information of a genuine ingredient, but not the one asked at the step 4302, the first server 16 dispatches an error message to the user device 12 to indicate that there is a mismatch. The operator can then correct the mistake by obtaining the correct ingredient and suppling the ingredient identification information which, if validated at step 4305, enables the operation to resume.

If the exception is the result of an expiry date, that has either passed or is close to expiry, the first server 16 sends a message to the user device indicating the expiry date related issue and can request the operator to obtain an ingredient that is fresher. If the operator does that and supplies the ingredient identification information associated with a fresh batch, the exception is cleared.

If the exception is the result of an incorrect concentration of an active agent in the ingredient, the first server 16 sends a message to the user device indicating the active agent concentration related issue and can request the operator to obtain an ingredient that has a correct concentration. If the operator does that and supplies the ingredient identification information associated with a correct concentration, the exception is cleared.

When all exceptions have been cleared and when the SOP has reached a point where the ingredients need to be mixed, the first server 16 sends instructions to the user device 12 asking the operator to put the ingredients into the mixer 10 and sends control signals to enable the mixer to operate. In this fashion, the mixer 10 would not operate unless a validation has been performed on the ingredients required by the SOP to reduce the possibility of human error in preparing the composition.

It can be possible to render larger scale composition compounding more efficient by decoupling the preparation of mixing containers from the actual mixing of those containers with a mixer, such as the mixer 10.

For example, when access to APIs or controlled substances is restricted physically or otherwise, it can be more efficient to prepare numerous containers with such APIs or substances during a first time frame ("preparation phase"), and then to mix the contents of those containers during a subsequent time frame ("mixing phase"). In other cases, a container can be prepared by one group of specialists and mixed by another group of specialists. There is a serious risk of error and it can be beneficial to keep track of which prepared containers contain which ingredients to be able to instruct the mixer 10 with the correct operating parameters.

Validating BUD of Ingredients

Without wishing to be bound by theory, the maximum BUD of a compounded composition can be reliant at least in part upon at least one of: (1) the expiration date of its ingredients (included in the batch information); (2) its form (included in the composition information); (3) its mode of administration, if applicable (also included in the composition information); and/or (4) its storage conditions (also included in the composition information). In some cases, the BUD of the compounded composition can be driven by the composition form, mode administration and storage conditions, or in other cases by the earliest expiration date of any ingredient. In some examples:

- the maximum BUD of a compounded solid composition (also known as solid dosage forms) can be no more than 180 days (6 months) from the date the compounded composition is compounded (when the BUD is derived based on the composition information only).
- the maximum BUD of a compounded solid composition (also known as solid dosage forms) can be no more than 180 days (6 months) from the date the compounded composition is compounded or the earliest expiration date of any ingredient used, whichever is shorter, when stored at controlled room temperatures (CRT) (when the BUD is derived based on the composition information and the batch information). A list of solid compositions within this category could be capsules, tablets, granules or powders.
- The maximum BUD of a compounded non-aqueous composition other than solid compositions (that have a reduced water activity ($a_w$)=<0.6) is no more than 90 days (3 months) from the date the compounded composition is compounded (when the BUD is derived based on the composition information only).

The maximum BUD of a compounded non-aqueous composition other than solid compositions (that have a reduced water activity ($a_w$)=<0.6) is no more than 90 days (3 months) from the date the compounded composition is compounded or the earliest expiration date of any ingredient used, whichever is shorter when stored at controlled room temperatures (CRT) (when the BUD is derived based on the composition information and the batch information). A list of non-aqueous compositions within this category could be suppositories, ointments, fixed oils or waxes.

the maximum BUD of a water-containing oral composition (also known as non-preserved aqueous dosage form) can be no more than 14 days from the date the compounded composition is compounded (when the BUD is derived based on the composition information only).

the maximum BUD of a water-containing oral composition (also known as non-preserved aqueous dosage form) can be no more than 14 days from the date the compounded composition is compounded or the earliest expiration date of any ingredient used, whichever is shorter, when stored at controlled cold temperatures (e.g., in a refrigerator) (when the BUD is derived based on the composition information and the batch information). A list of aqueous compositions within this category could be aqueous compositions are those with a water activity ($a_w$)>0.6 including: emulsions, gels, creams, solutions, sprays or suspensions.

the maximum BUD of a water-containing topical/dermal or mucosal liquid and semisolid composition can be no more than 30 days from the date the composition is compounded (when the BUD is derived based on the composition information only).

the maximum BUD of a water-containing topical/dermal or mucosal liquid and semisolid composition can be no more than 30 days from the date the composition is compounded or the earliest expiration date of any ingredient used, whichever is shorter, when stored at controlled cold temperatures (when the BUD is derived based on the composition information and the batch information).

Figure 16:
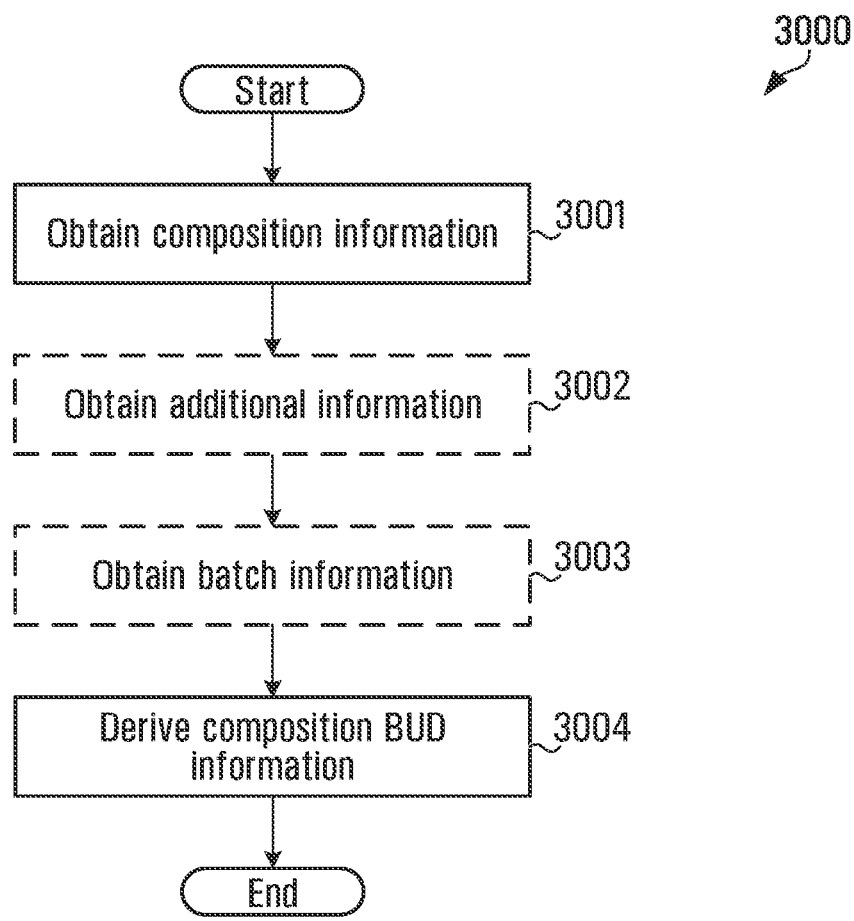
FIG. 16 is a flowchart of a process for recommending a beyond-use-date.

The data analytics module 610 can be configured to provide a recommendation of a BUD to the account holder X for a composition compounded or to be compounded. FIG. 16 shows a process 3000 for making a BUD recommendation. In a first step 3001, the data analytics module 610 obtains composition information that can include ingredients for the specific composition, a composition type (e.g., solid, aqueous, non-solid non-aqueous, etc.), a mode of administration for the composition (e.g., oral, dermal, topical, mucosal, etc.), storage conditions for the composition, etc.

Figure 17:
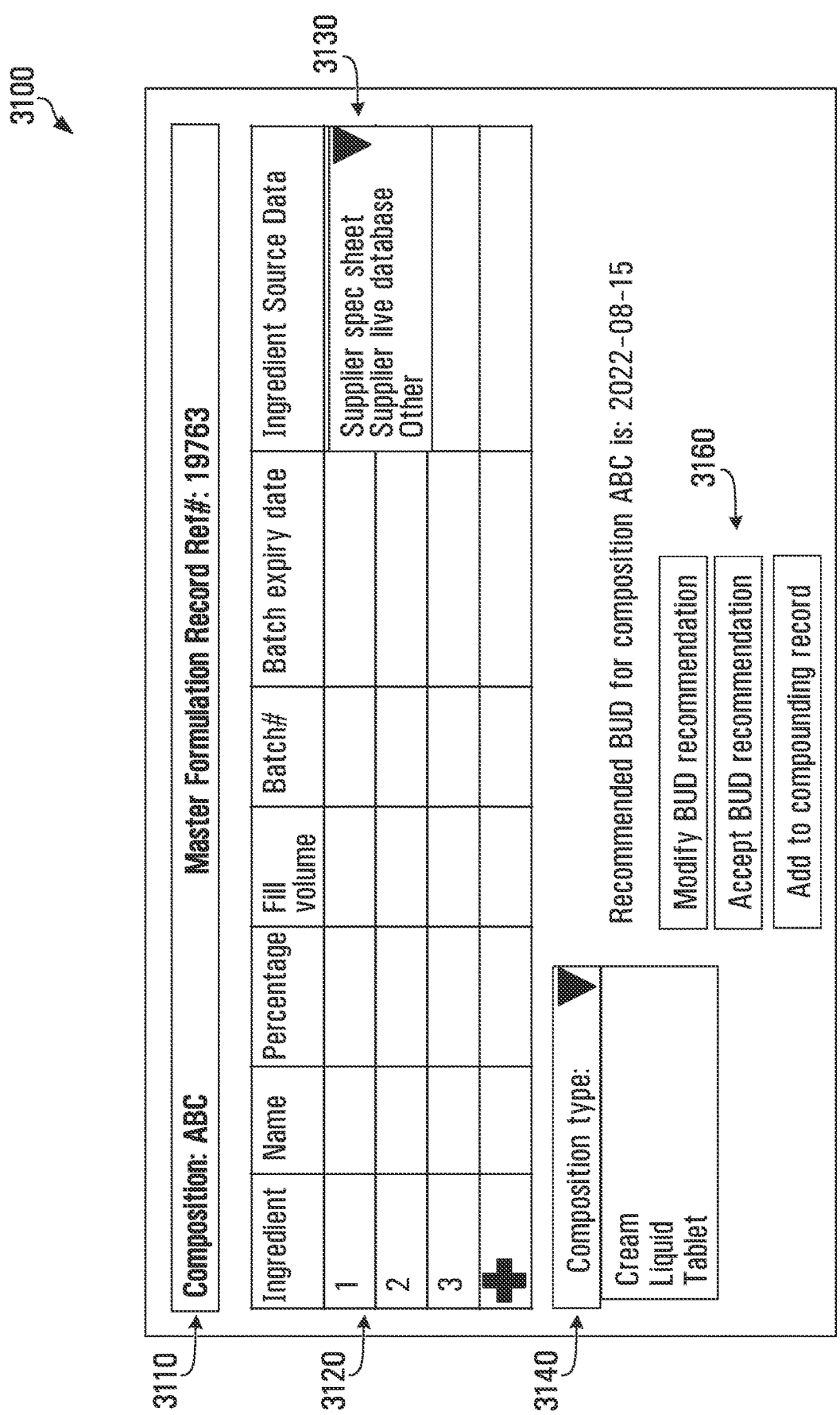
FIG. 17 illustrates a GUI on the user device that can appear during execution of the flowchart in FIG. 16.

The user device 12 can prompt the account holder X at step 3001 via the interactive program module 250 to interact with the database on the server 16 (or 19) and access an MFR or an SOP corresponding to the composition wherein names of the individual ingredients, their relative proportions and composition type can be entered or otherwise selected by the account holder X via a graphical user interface GUI 3100, for example of the GUI 3100 being shown in FIG. 17.

In an optional step 3002, additional information can also be obtained in addition to the composition information obtained at step 3001, such as container type, storage conditions, etc. to the additional information can be obtained through access to an MFR or a SOP corresponding to the composition for which the BUD should be derived. Alternatively, the additional information can also be obtained via external, public or private sources of compounding practices, scientific literature, etc. In a further optional step 3003, batch information can also be obtained. Within the context of the present disclosure the term "batch" can be used interchangeably with "lot" and generally refers to a specific portion/fraction/quantity/volume of an ingredient having entirely uniform character and quality. The batch information can include information regarding a date of preparation of a batch, a date of shipping of a batch, an expiry date for the batch, storage conditions, etc. In one example, the composition information obtained at step 3001, as well as the additional information and the batch information optionally obtained at steps 3002 and 3003, respectively, can be derived from information present in the database 18 however this needs not be the case in other examples.

There can be multiple, distinct batches of one specific ingredient, each one of the batches of the specific ingredient having a different expiry date. In this case, the user device 12 upon interacting with the inventory database can return a list of all the existing batches within the inventory containing the same specific ingredient and run a decision logic on which batch of the specific ingredient needs to be used for compounding and BUD recommendation.

At step 3004 the composition BUD information is then derived based on the composition information obtained at step 3001, and optionally also based on the additional information and/or the batch information obtained at steps 3002 and 3003, respectively. In other words, the composition BUD information can be derived only based on the composition information (e.g., the composition type, the mode of administration for the composition, etc.), however it can also be derived based on the composition information and the additional information, the composition information and the batch information as well as based on the composition information, the additional information and the batch information, as further described below. The composition information includes a maximum BUD for the composition compounded or to be compounded.

A first example of a logical process at step 3004 can therefore be to determine a form, a mode of administration and storage conditions from the composition information obtained at step 3001 and then derive the composition BUD information using a prescribed timeframe associated with the combination of form, mode of administration and storage conditions. For example if the prescribed timeframe associated with the combination of form, mode of administration and storage conditions is 30 days, then at step 3004 the composition BUD information (e.g., the maximum BUD) is derived by adding 30 days to the date of the compounding (which for example can also be the date at which the process 3000 is run). Because the BUD generated at step 3004 is a maximum BUD, an operator will be in a position to edit the maximum BUD such that the "actual" BUD is nearer to the date of compounding of the composition compared to the maximum BUD, however because the outcome of step 3004 is a maximum BUD the operator will not be in a position to edit the BUD such that the "actual" BUD is further from the date of the compounding compared to the maximum BUD. Another example of a logical process at step 3004 can include an identification of the nearer BUD between the maximum one prescribed by (i) the composition form, mode administration and storage conditions and (ii) the earliest expiration date of any ingredient used.

In some cases, the BUD can also be reliant on stability information regarding specific drug(s) used in the compounded composition, stability association regarding known associations of ingredients, etc. This information is generally obtained from technical documentation, scientific literature or stability tests. Such references include: Trissel's Stability of Compounded Formulations, Trissel's Handbook of Injectable Drugs, AHFS Drug Information, United States Pharmacopeia, Remington: The Science and Practice of Pharmacy, USP Dispensing Information, Journal of Pharmaceutical Sciences, American Journal of Health-System Pharmacy and International Journal of Pharmaceutical Compounding.

In one example, the recommended BUD can be determined immediately after the composition is compounded by the mixer 10. In another example, the recommended BUD can be determined before the composition is compounded by the mixer 10 and can be during the selection of batches or lots of individual ingredients to be used for compounding.

Referring to FIG. 17, the recommended BUD for the composition could be stored for future references. In one example the recommended BUD could be transmitted through the user device 12 and as shown in the example of GUI 3100 by adding the recommended BUD into the compounding record and storing the compounding record on the database. The GUI 3100 can include a header section 3110 for composition name and the master formulation reference to which it relates. The GUI 3100 can further include a table of ingredients 3120 wherein the ingredients to be used for compounding the composition mentioned in section 3110 can be added. Parameters that can be filled into the table and for each ingredient, can include name, percentage, batch number and expiry date. The GUI can also have a drop-down menu 3130 wherein the source of data obtained for each of the ingredients can be selected. In one example, the source data could be from the supplier spec sheet that can be manually entered by the user and through the user device. In another example, the source data could be from the supplier spec sheet and could be available on the first database 18 or second database 19 and can be automatically filled in. In another example, the source data can be obtained from suppliers' live database. In this example, the user can input the name of the ingredient that has been supplied by a supplier in one column and upon selecting the supplier's live database, the remaining information will be filled in automatically. Further, the user, through the GUI 3100 can access to another drop down menu 3140 wherein the composition type can be selected for BUD recommendation. Composition types that can be selected from the drop-down menu 3140 include cream, liquid, tablet, etc. Once the information is filled in, the BUD for the composition will be illustrated on the BUD recommendation section 3150. The operator at this point can choose among several options 3160 with respect to the recommended BUD. The operator can opt to modify the BUD recommendation in case a change can be needed in the information provided prior. The operator can also accept the recommended BUD and take appropriate action. The operator can also have the option to add the recommended BUD to the compounding record.

RFID Containers with Mixers

Referring again to FIG. 13, the data entry device 1000 can make use of non-contact tags, such as RFID tags, rather than a QR or bar code scanner) to acquire the CAS number of an ingredient that an operator is adding to the container in which mixing is to occur. This tagging solution electronically tags individual containers as part of the system's validation processes. The RFID tag can include a memory, an antenna, and a microcontroller that allows reading and writing of the memory content. The RFID tag can be a passive RFID tag, to which power is supplied when writing to the memory, and which can be read by energizing it wirelessly from a distance, such that it releases the contents of its memory. An active RFID tag can also be used, whereby the tag includes a built-in power supply that is replenished by a battery, kinetic movement, etc.

The proposed tagging solution influences two phases of composition compounding, referred to generally herein as a "preparation phase" and a "mixing phase".

Figure 18:
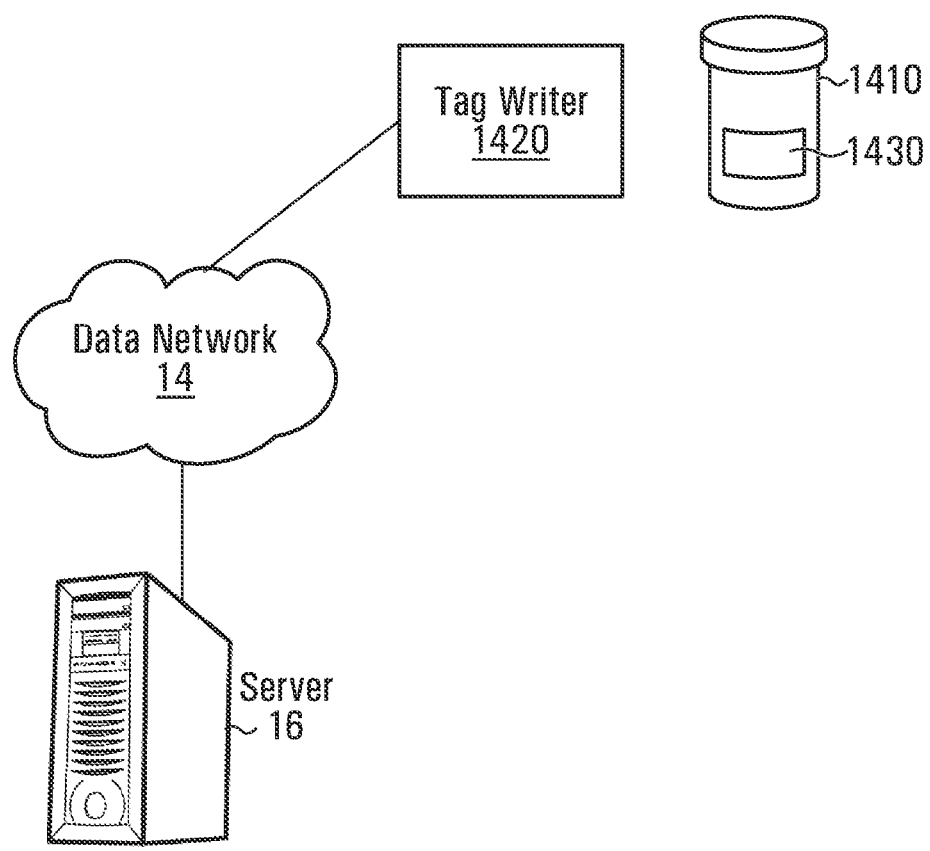
FIG. 18 is a block diagram showing a server, a tag reader and a tag-enabled container.

FIG. 18 shows a tag-enabled container 1410 and a tag writer 1420. The container 1410 includes a tag 1430 such as an RFID tag. Other devices can also be suitable, such as bar codes or devices based on NFC or Zigbee technology, for example. The tag writer 1420 can be a device that is capable of writing information to a tag such as the tag 1430 of the container 1410. The tag writer 1420 can be connected to a back-end server, such as the first server 16. The tag writer 1420 can have a console that can be accessed by the operator. The operator can access a separate user device (such as the user device 12) that is connected to the tag writer 1420, e.g., over a wireless or wired link. The operator can use the user device 12 to connect to the back-end server (e.g., first server 16) over a data network (e.g., data network 14), such as the internet. In any event, the operator is assumed to be desirous of preparing a total weight/volume of a formulation defined by a formula, e.g., a list of ingredients in certain absolute and relative quantities. During the preparation phase, the operator fills the tag-enabled container 1410 with the appropriate ingredients in the appropriate absolute and relative quantities, and then enables a write operation to the tag 1430 of the tag-enabled container 1410 using the tag writer 1420. The information written to the tag 1430 could be the formula (including, or not, the total weight/volume), or a code that is maintained in the back-end first server 16 and maps to the formula but is meaningless to someone who does not know this mapping.

The above operations can also be done in reverse, e.g., the tag 1430 can be written to first and then the tag-enabled container 1410 can be filled. The tag 1430 can be a loose item and its memory is written to separately by the tag writer 1420, following which the loose tag is affixed to a virgin (non-tag-enabled) container, thus yielding in a tag-enabled container such as the container 1410. It can also be possible to integrate tag writing with the validation process. For example, the tag writer 1420 can be configured to write to the tag 1430 only if the validation process has been passed successfully, and/or to write to the tag 1430 an indication of whether the validation process was passed successfully or even carried out.

The preparation phase is now complete, the result being a filled tag-enabled container 1410 whose tag 1430 is indicative of its contents, either explicitly or by way of a code. The mixing phase follows.

Figure 19:
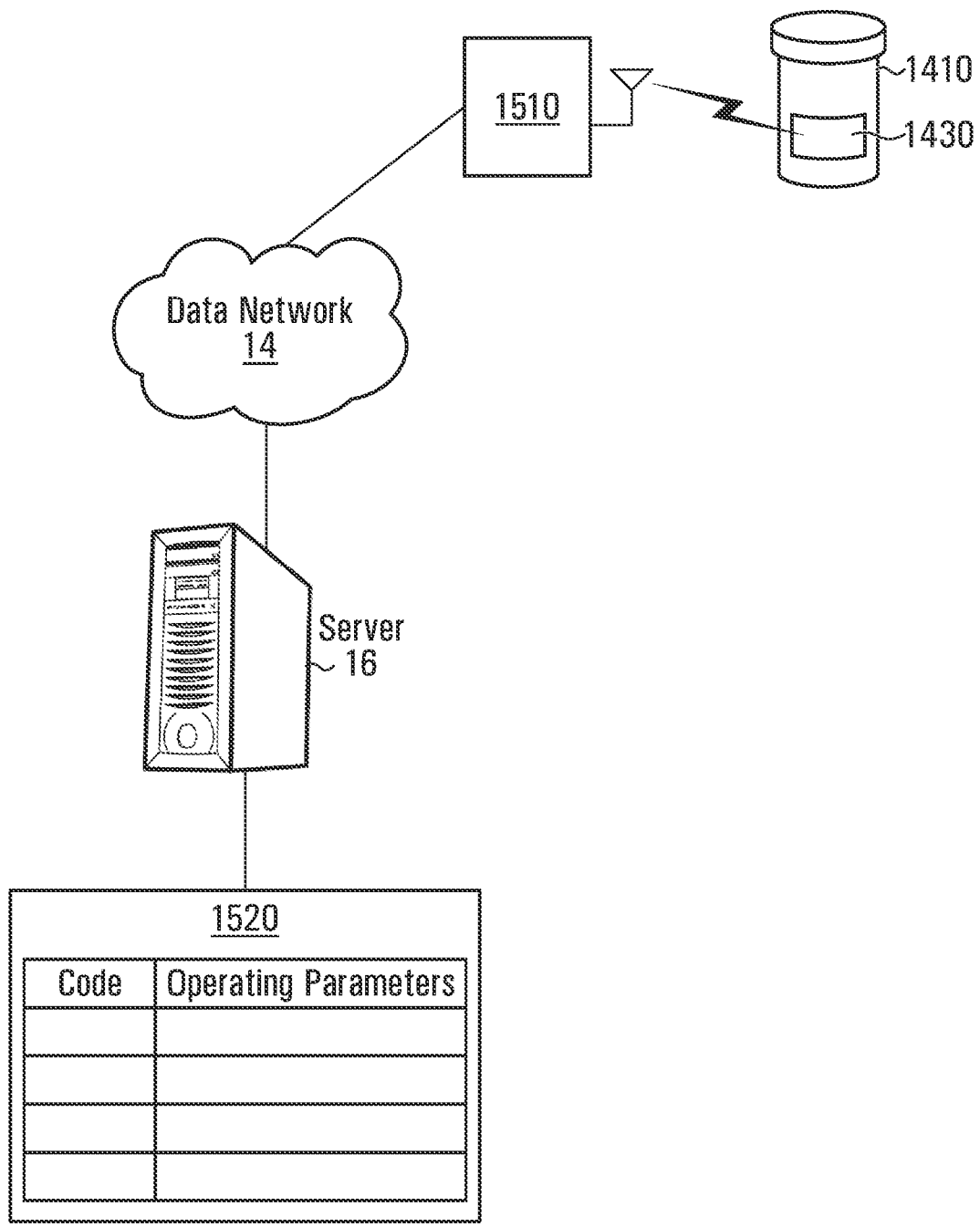
FIG. 19 is a block diagram showing the tag reader being coupled to a database containing operating parameters.

FIG. 19 shows the tag-enabled container 1410 and a tag reader 1510. The tag reader 1510 is connected to a database 1520. The database 1520 can be stored in the first server 16, to which the tag reader 1510 can be connected via the data network 14. In one embodiment, which can be applicable in the case where the tag 1430 stores the contents of the container 1410 explicitly, the database 1520 stores a mapping between formulas (and possibly also total weight) and the optimal operating parameters for the mixer 10 (e.g., the database 1520 stores a table similar to table 1210). In another embodiment, which can be applicable in the case where the tag 1430 stores a code that uniquely corresponds to a formula (and possibly also total weight), the database 1520 stores a mapping between codes and sets of optimal operating parameters for the mixer 10.

In either case, the operating parameters are retrieved from the database 1520 and conveyed to the mixer 10. This can be done in a variety of ways.

Figure 20A:
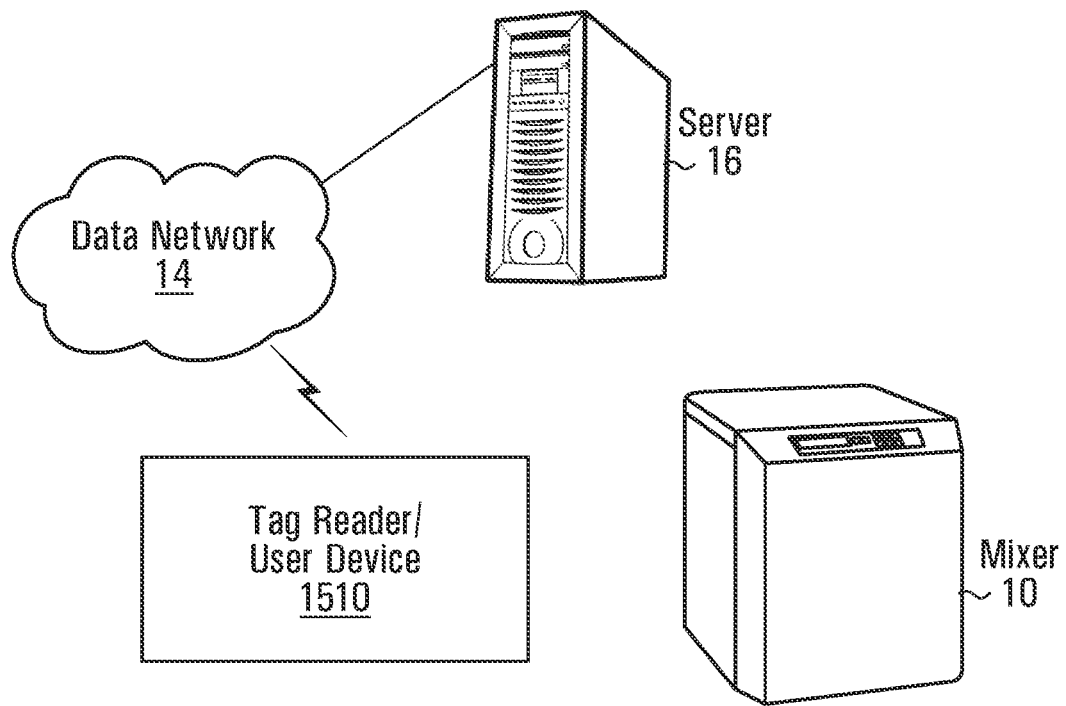
FIGS. 20A to 20C illustrate the tag reader and the mixer in various states of interconnectedness.

FIG. 20A shows that the tag reader 1510 can be integrated with a user device (e.g., a smartphone or tablet), and the operating parameters are sent from the first server 16 to the user device/tag reader for display thereon. The operator then enters the operating parameters into the mixer (not shown). For this embodiment, the mixer 10 does not require an external or networked connection.

Figure 20B:
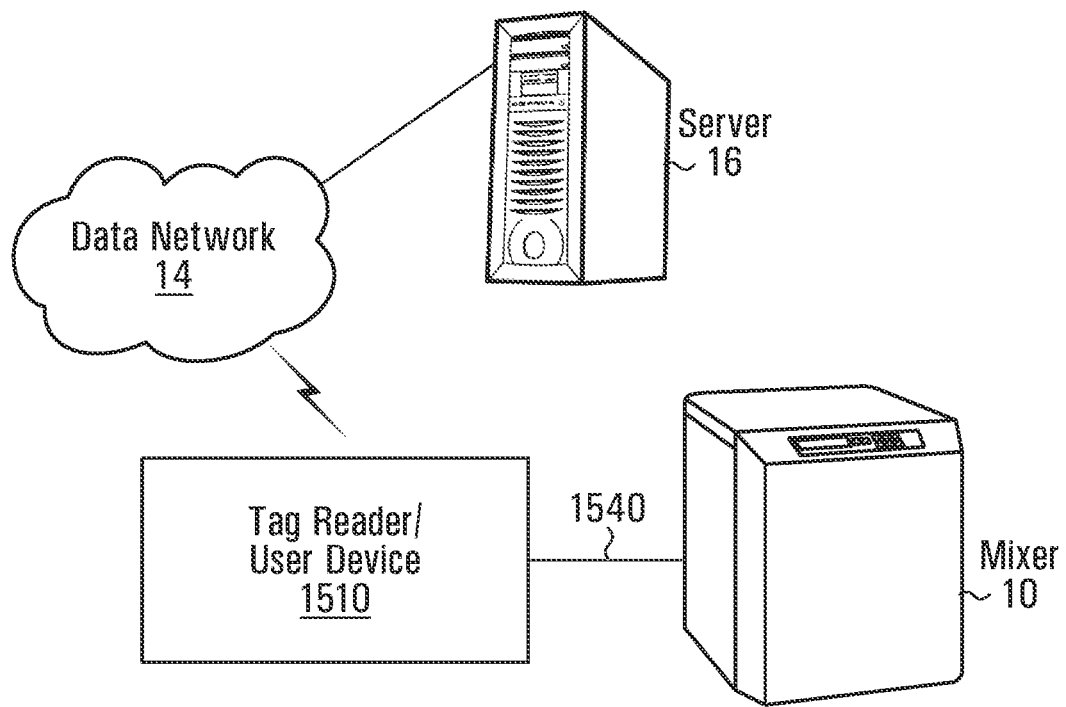

FIG. 20B shows that the tag reader 1510 can be embodied as a separate system, and the mixer 10 has an external wired or wireless connection 1540 to the tag reader 1510. In this case, the operating parameters are sent from the first server 16 to the tag reader 1510, which sends the operating parameters to the mixer 10 via the external connection 1540.

Figure 20C:
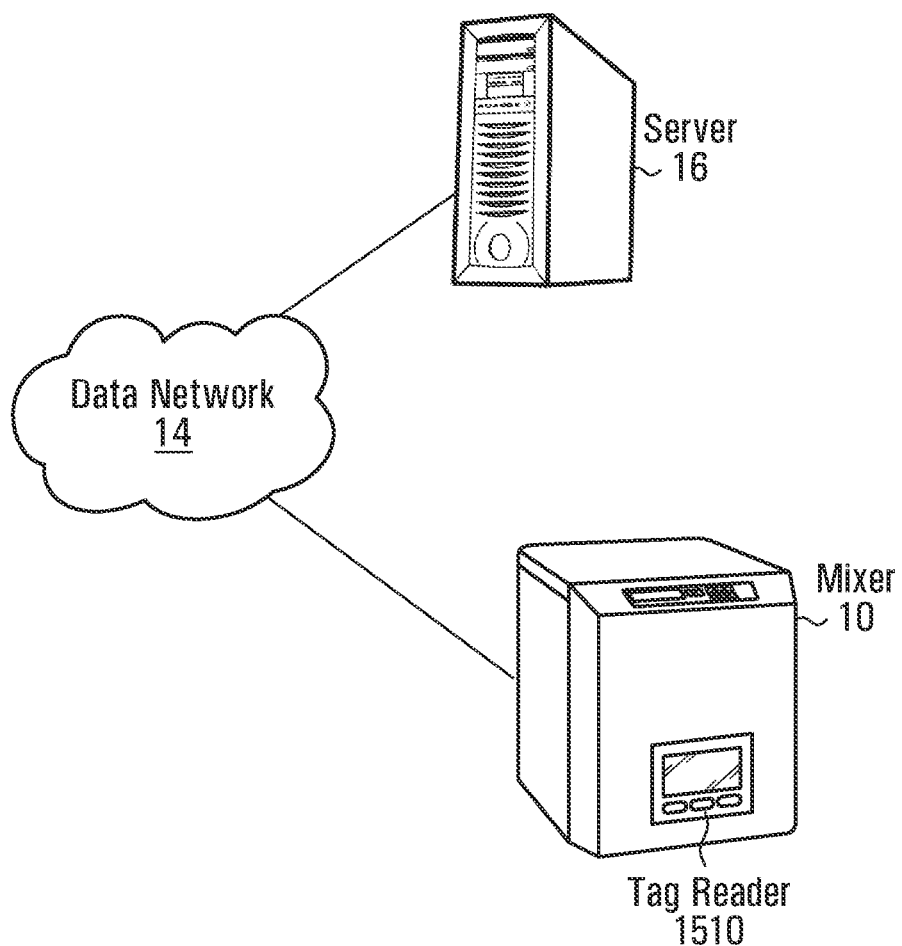

FIG. 20C shows that the tag reader 1510 is built into the mixer 10, and the mixer 10 has a connection to the data network 14. In this case, the operating parameters are sent directly form first server 16 to the mixer 10 over the data network 14.

The possibility of human error is significantly reduced as the operator does not need to enter any data into the mixer 10. The tag-enabled container 1410 is simply read by the tag reader 1510, and the operating parameters for the desired formulation are sent to the mixer 10. The individual performing the mixing phase does not need to be as skilled as the person performing the preparation phase. This could reduce operating costs and increase efficiency of a compounding pharmacy that implements the described method.

Figure 21:
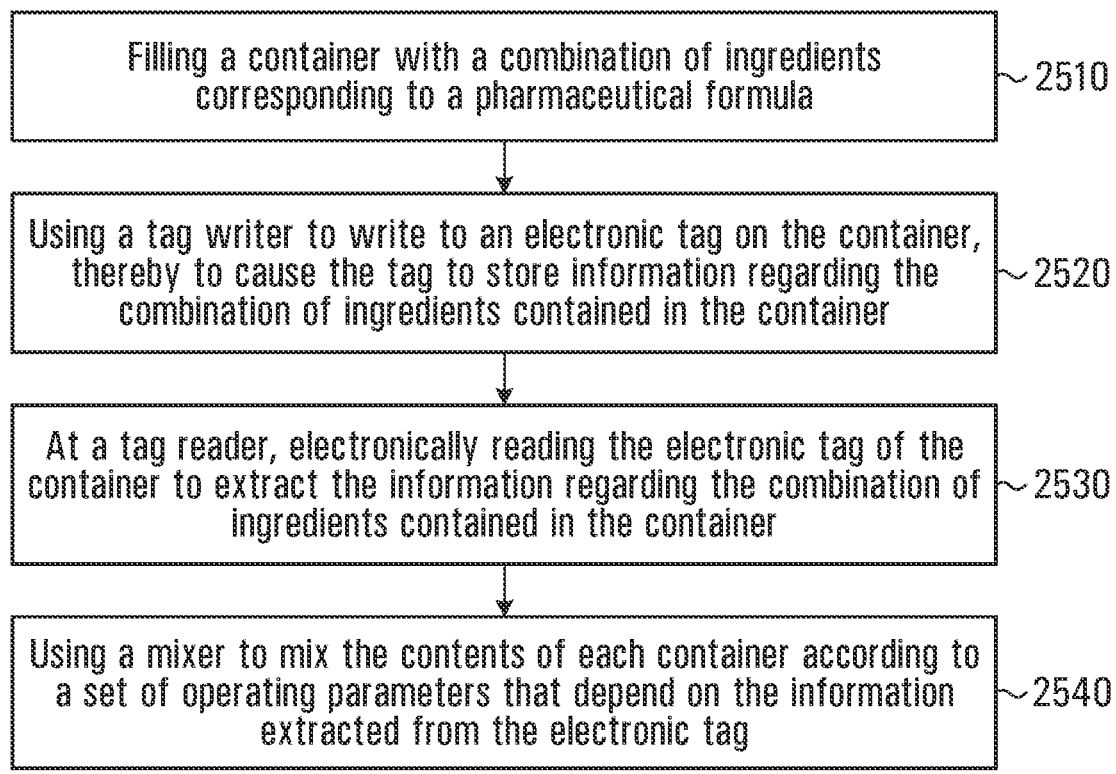
FIG. 21 shows a method of reading electronic tags.

FIG. 21 shows a manufacturing method that includes a step 2510 of filling a container with a combination of ingredients corresponding to a pharmaceutical formula; a step 2520 of using a tag writer to write to an electronic tag on the container, thereby to cause the tag to store information regarding the combination of ingredients contained in the container; a step 2530 of, at a tag reader, electronically reading the electronic tag of the container to extract the information regarding the combination of ingredients contained in the container; and a step 2540 of using a mixer to mix the contents of each container using a set of operating parameters that depend on the information extracted from the electronic tag.

Use of Scales with Mixers

Figure 22:
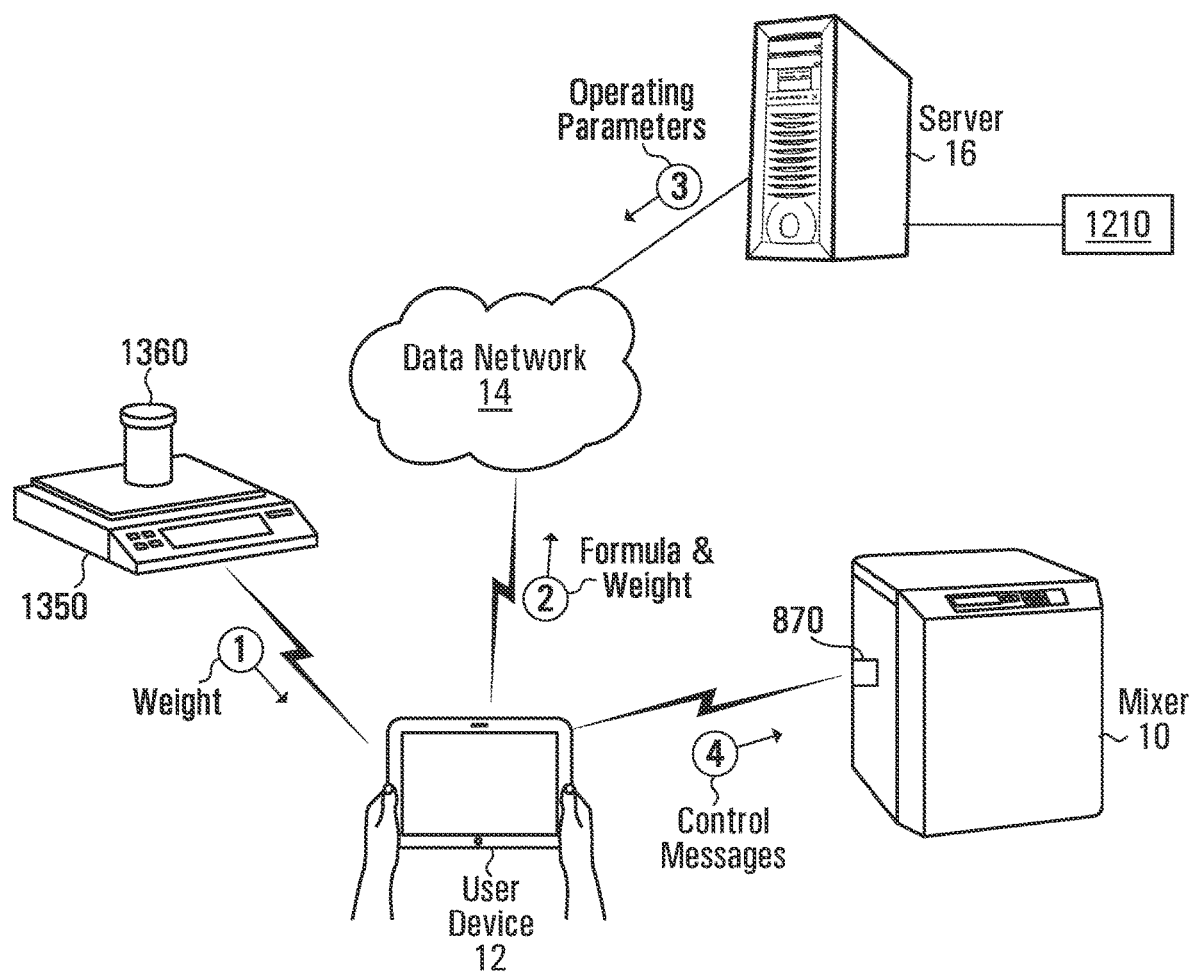
FIG. 22 is a user device and mixer with a scale.

Referring to FIG. 22, the validation process can involve a scale 1350 that ensures that not only are the correct ingredients being added to the mixing container, but they are being added in the correct quantities and/or proportions. Specifically, scale 1350 is connected to the user device 12 and is configured to output weight measurements. The mixer control application 120 is configured to read the weight measurements made by the scale 1350. The received weight measurements and the weight that specified in the SOP file are compared. The SOP file can not specify the weight of each ingredient but rather the relative proportions of the weight of each ingredient. In such cases, the scale 1350 can be used to collect the weight of each ingredient being added by the operator, and then the mixer control application 120 calculates the relative proportions to determine whether they correspond to, or are within a certain tolerance of (e.g., within 0.1%, 1% or 5%) of the relative weight proportions of the ingredients listed in the SOP file.

In one example, and in case of network-enabled mixers, the scale 1350 and mixer 10 can be both connected to the remote server 18 and the server 18 can be able to manage the interplay between the scale 1350 and mixer 10. The user device 12 can obtain an SOP wherein the weights indicated in the SOP, are different beyond a certain acceptable tolerance. In such case, the scale readouts and the weight indicated in the SOP are compared at database 18 and the user device 12 can in turn receive communication as to not operate the mixer until the difference in weights from the two sources is resolved. The beyond-tolerance discrepancy in weights can be corrected by the user device 12, wherein the user device 12, can obtain the scale 1350 readout and further adjust the mixing parameters (e.g., RPM and mixing duration) to account for the discrepancy.

To use the scale 1350, the operator places a container 1360 containing the ingredients onto the scale 1350 and enters the corresponding formula on the user device 12 in one of the above ways. The user device 12 reads the scale 1350 to obtain a weight, then accesses the formula database 1210, which could be in the memory of the user device 12 or accessible over the data network 14.

This approach can be particularly suitable when the formula database 1210 has varying operating parameters for different total formulation weights, even for the same formula. Once the operating parameters are received, the user device 12 places the operating parameters into one or more control messages that is/are sent to for the mixer 10. Optionally, the operating parameters are also displayed on the screen of the user device 12. The operator adds ingredients to the container 1360 using a formula, selects the formula via a graphical user interface on the user device 12, and presses "start". The remaining operations are automated.

In some instances, the operator places a container 1360 containing the ingredients onto the scale 1350 and enters the corresponding formula via a graphical user interface on the mixer 10. The mixer 10 reads the scale 1350 to obtain a weight, then accesses the formula database 1210, which could be in the memory of the mixer 10 or accessible over the data network 14. Here, the operator adds ingredients to the container 1360 according to a formula, selects the formula via a graphical user interface on the mixer 10, and presses "start". The remaining operations are automated.

Automation of Refill Requests

In some scenarios, a composition could to be repeatedly compounded using the exact same procedures used for the first time by the operator (e.g., pharmacist) to compound the composition. This can be the case when a refill on a previously compounded composition is requested by an individual (e.g., patient) who had consumed the composition. Repeating the exact same compounding procedure that was once carried out successfully could not only save time for the operator (e.g., pharmacist) but also would minimize compounding errors that can otherwise be introduced into the compounding process.

Figure 23:
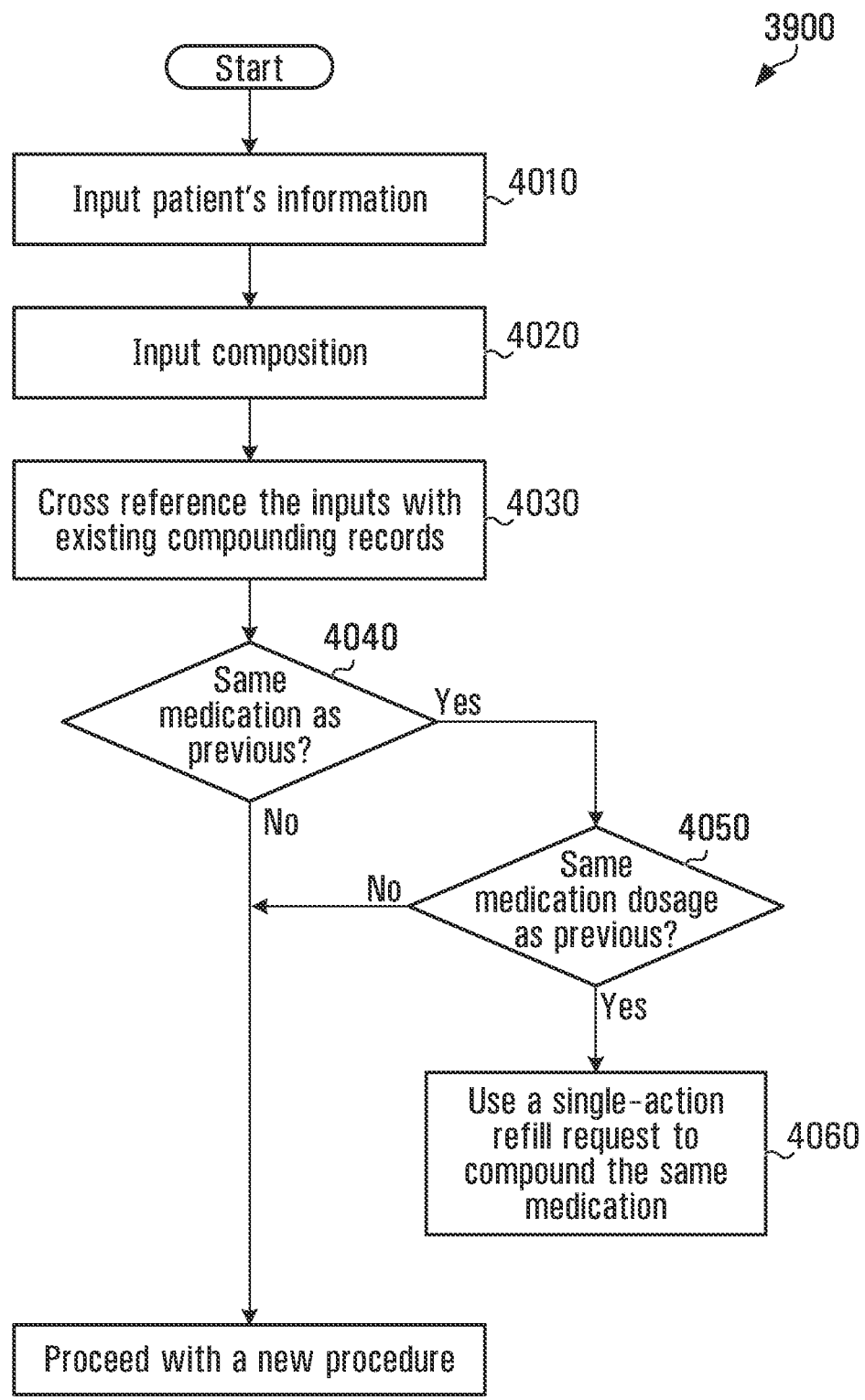
FIG. 23 is a flowchart of a process for one-click refill.

FIG. 23 shows that prior to initiating the compounding process, the operator (e.g., pharmacist) can select to enter the individual's name at step 4010 as well as the composition to be compounded for the individual at step 4020. In one example, the operator through user device 12 can query the compounding records database at step 4030 to verify whether records of compounding same composition for the same individual have existed at step 4040. The user device 12 can further match the dosage of the previously compounded composition in the compound record with the received composition refill request at step 4050 before taking any action. The compounding record database can reside at the local pharmacy server and can be accessed by the user device. The compounding record database can reside over a remote server storing the databases of a plurality of pharmacies all of which can be accessed by the user device to query a compounding record. Once the compounding record corresponding to the first time the composition was compounded for the individual is retrieved, the operator through user device 12 can run a single-action command at step 4060 that will initiate a sequence of automatic communications between the server, database and user device which ultimately translates into control messages sent to mixer 10 via mixer control application 120 for compounding.

Figure 24:
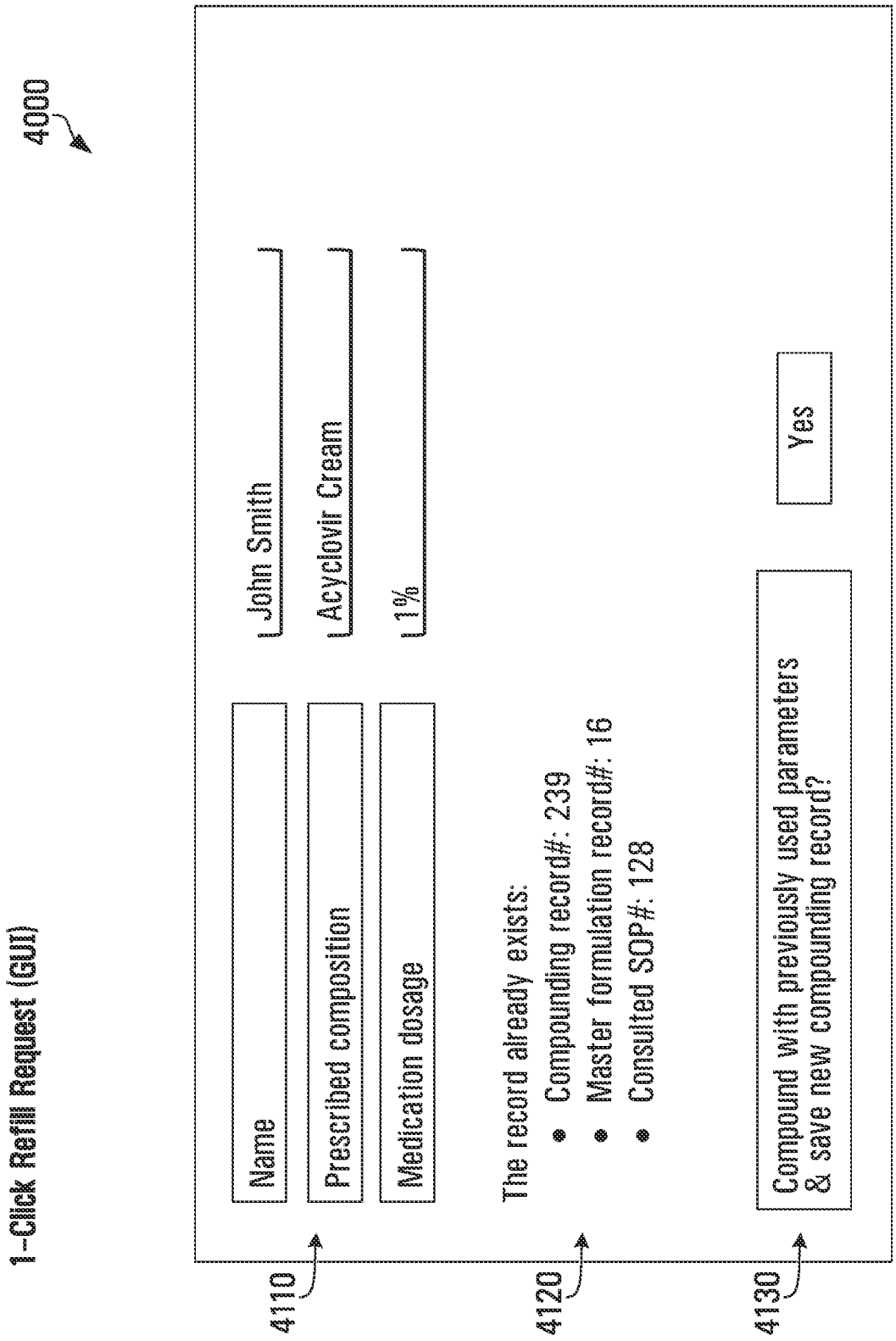
FIG. 24 illustrates a GUI on the user device that can appear to the user.

In FIG. 24, the user device 12 can prompt the operator through a GUI 4000 to enter an individual's name, prescribed composition name and composition dosage at section 4110. The user device 12 upon receiving the information will instantly query the compounding records database. The compounding record database can reside on the local pharmacy server or on a remote server storing the databases of a plurality of pharmacies all of which can be accessed by the user device. In case of the existence of one or more prior compounding record for the same individual, same composition and same dosage, a notification 4120 can appear on the GUI 4000. In one example, the notification can be in the form of a pop-up message appearing as a side window on the GUI 4000 notifying on the existence of one or more prior compounding records only. In another example, the notification can be in the form of a message on the same window of the GUI 4000 notifying on the existence of one or more prior compounding record only. In another example, the notification can point toward prior compounding record number(s) existing on the compounding record database. In another example, the notification can point toward not only the prior compounding record number(s) but also the previously consulted SOP or MFR. The notification can further activate a dialogue box 4130, requesting permission for repeating the prior compounding process (refill request) using the previously used parameters. The operator through user device 12 can proceed by a single-action button to initiate a sequence of automatic communications between the server, database and user device which ultimately translates into control messages sent to mixer 10 via mixer control application 120 for compounding. This will be described shortly. In case of multiple compounding records pointing toward the same individual and same composition, the operator, through user device 12, can run a decision logic as to which of the compounding records need to be considered for data extraction and repetition of the compounding process.

Figure 25:
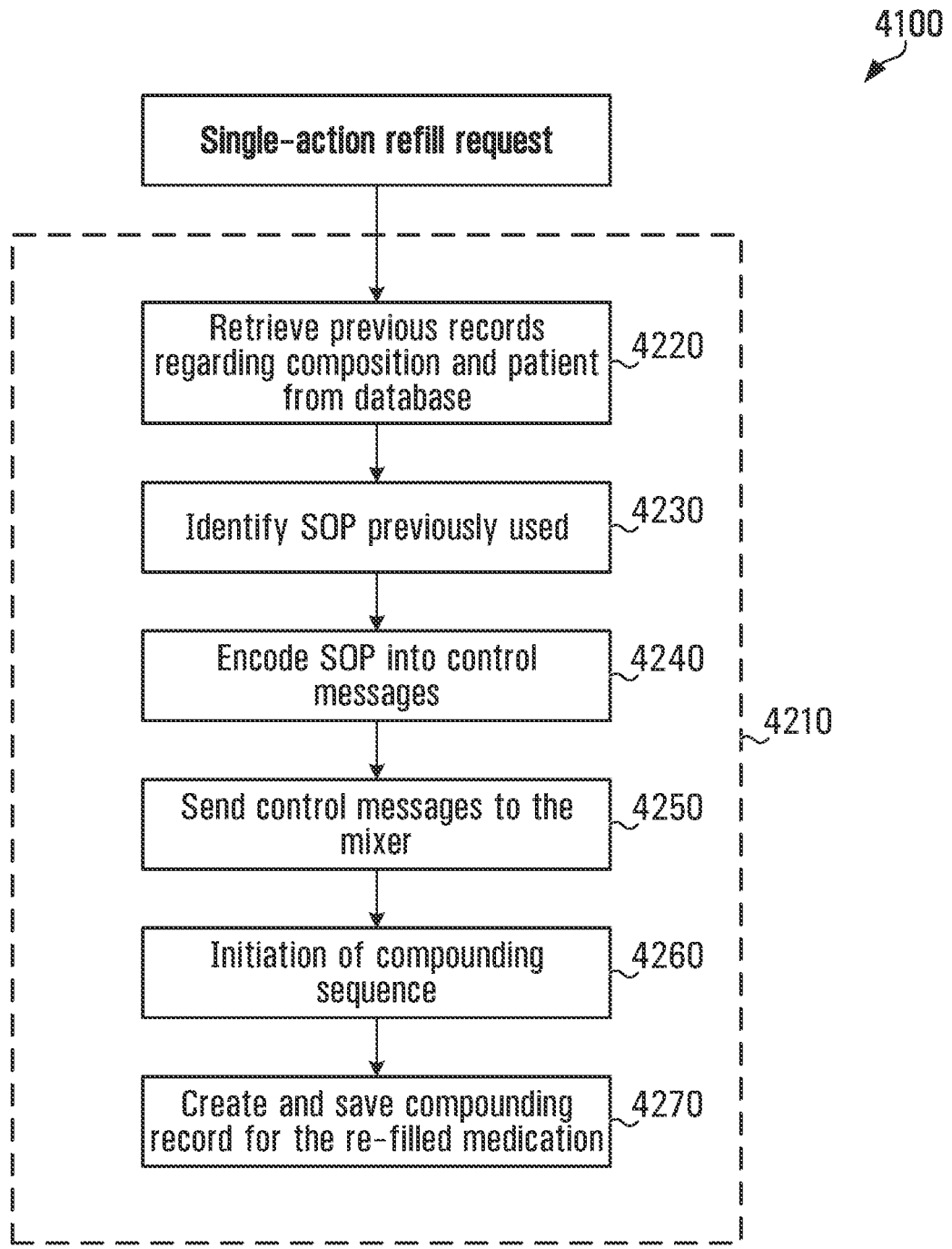
FIG. 25 is a flowchart of a process for refill requests.

The sequence (executed behind the single-action button) for initiating the refill request is explained with reference to FIG. 25. Once the single-action button for the refill request is clicked via a GUI, the user device 12 initiates communications with the server to retrieve the previous compounding record at step 4220. In one example, the user device can communicate with the server located at the pharmacy level and query the database to retrieve the compounding record (or records) associated with the previously completed compounding process. In another example, the user device 12 can communicate with the remote server and query the database to retrieve the compounding record (or records) associated with the previously completed compounding process. Once the compounding record corresponding to the previously completed compounding process is retrieved, the operator through user device 12 can obtain the previously consulted SOP at step 4230. The consulted SOP can then be transmitted to user device 12 upon communication between the user device and the server database storing the SOP. The user device 12, through mixer control application 120, encodes the SOP into control messages at step 4240 and subsequently transmits them to the mixer 10 at step 4250. Once the control messages are transmitted to the mixer, the mixer 10 can repeat the compounding process at step 4260 in a way described elsewhere within this disclosure. Upon completion of the compounding process, the procedure in FIG. 26 will be executed to obtain necessary information for generating a new compounding record at step 4270. The newly generated compounding record can be stored at the compounding record database either on a local server at the pharmacy level or on a remote server where it could be accessed from all the pharmacies having communications with the remote server and through the user devices located at each pharmacy.

Figure 27:
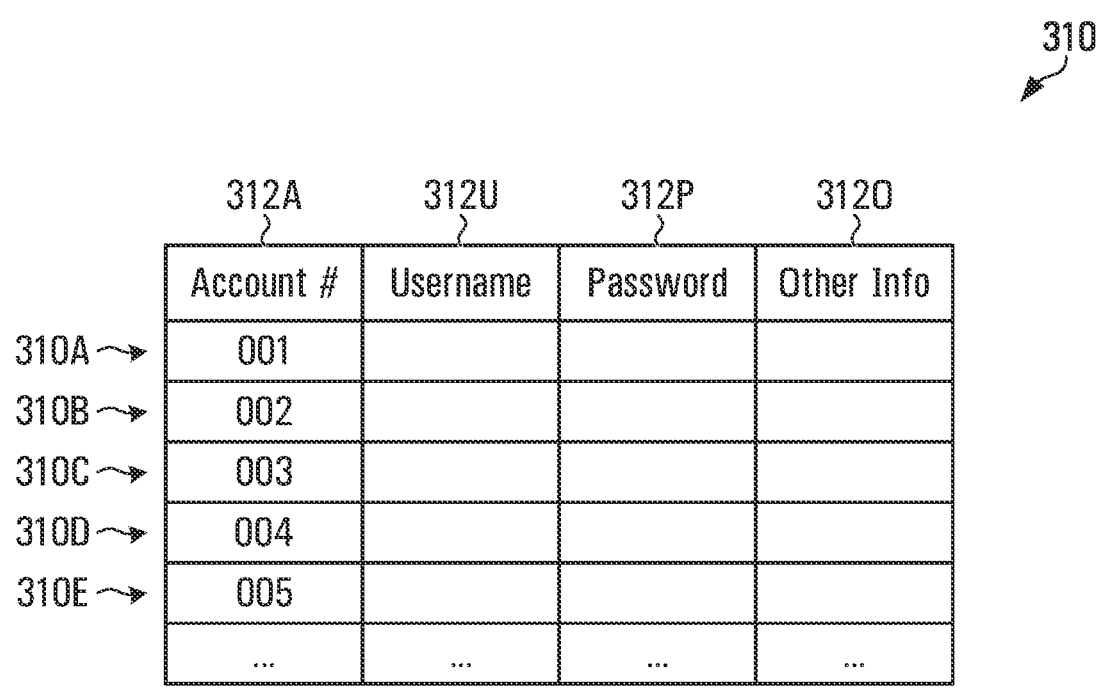
FIG. 27 illustrates a credentials table for storing account information.

An additional front-end feature performed by the initialization module 240 is an account verification process before activating the link or icon 242. FIG. 27 shows possible contents of the first database 18 as a table 310 of records 310A . . . 310E, hereinafter referred to as a "credentials table". Each of the records 310A . . . 310E in the credentials table 310 includes a plurality of entries, in each of an account number field 312A, a username field 312U, a password field 312P and possibly other fields (e.g., other information field 3120). For a given one of the records 310A . . . 310E, the entry in the account number field 312A is information corresponding to an account holder associated with that record (e.g., a unique account number or customer name). The entry in the username field 312U and password field 312P represents credential information that can be set up by the account holder during a prior "account setup" phase. The entry in the info field 3120 could be related to other information associated with the account holder, such as the make and model of a mixer purchased by the account holder, the date of purchase, the software version and servicing information, etc. Those skilled in the art will appreciate that the reference to a "table" being used for account information is a conceptualization of an otherwise tangible and non-transitory medium for storing such information and the first database 18 can implement any suitable organizational format or data structure in lieu of the credentials table 310.

Referring back to FIGS. 2A and 2B, as part of the account verification process the initialization module 240 can be configured to request credentials (e.g., a username and/or password) from the user device 12. The initialization module 240 verifies these credentials against the information stored in the credentials table 310 of the first database 18 and requires a match before the interactive program module 250 is launched and presented to the user via the user device 12

The account verification process can also include a verification of the identity of the mixer 10 as an authorized network device. For instance, the first server 16 can be configured to provide services only to authorized devices and before proceeding with delivering services the process will verify if the mixer 10 is a device on the authorized list. The verification can include receiving from the mixer 10, in addition to the model number and other characterizing information, a unique identifier that distinguishes the machine from other machines of the same model. The unique identifier can be a serial number that is encoded in the mixer 10 memory in tamper-proof fashion.

The methods described above with respect to the front-end uses of the machines, methods, and systems described herein can be combined. For example, the system can implement a GUI functional block configured for implementing a GUI that provides a user with an opportunity to specify a compounding formula for a composition. The system and code also has an ingredient validation functional block configured for consulting a database on the basis of the compounding formula to derive a formulation ingredient to be used in preparing the composition, receiving a code generated by a code-reader when reading data applied on a container with a first ingredient, and then determining on the basis of the code if the first ingredient matches the formulation ingredient. A planetary mixer control functional block is configured for consulting the database on a basis of the specified compounding formula to determine mixing parameters for a planetary mixer. The mixing parameters are associated with the specified compounding formula, and the block causes a motor assembly of the planetary mixer to apply superimposed rotation and revolution movements to a container in accordance with those mixing parameters. If the determining step fails to match the first ingredient to the formulation ingredient, the block prevents operation of the motor assembly.

In some embodiments, the ingredient validation functional block is configured for receiving a plurality of codes sequentially input by the code reader for respective containers and ingredients, consulting the database on the basis of the compounding formula to derive a plurality of formulation ingredients to be used in preparing the composition, and determining at least in part on the basis of the codes if the ingredients held in the plurality of containers match the formulation ingredients. The planetary mixer control functional block is configured to prevent operation of the motor assembly when the determining step fails to match all the codes to the formulation ingredients. The GUI functional block is responsive to the ingredient validation functional block to display an error message on the GUI when the determining fails to match the code to the formulation ingredient, and the error message can indicate that the ingredient held in the container is incorrect for the specified compounding formula.

In some embodiments, a non-transitory medium storing computer-readable instructions which when read and executed by at least one processor of a computing device implements a GUI functional block configured for implementing a GUI that provides a user with an opportunity to specify a compounding formula for composition. An ingredient validation functional block is configured for receiving a code input by a code reader reading data on a container holding and associated with a first ingredient, and processing the code to determine if the first ingredient is a valid ingredient for the specified compounding formula. A planetary mixer control functional block is configured for consulting a database arrangement on a basis of the specified compounding formula to determine mixing parameters for a planetary mixer that are associated with the specified compounding formula, and causing a motor assembly of the planetary mixer to apply superimposed rotation and revolution movements to a container in accordance with the mixing parameters determined from the consulting. The planetary mixer control functional block can prevent operation of the motor assembly when the ingredient validation functional block determines that the first ingredient is not valid for the specified compounding formula.

In some embodiments, the ingredient validation functional block determines that the first ingredient is not valid when the first ingredient is a wrong ingredient for the specified compounding formula or when the first ingredient has a use-by date that has passed. The ingredient validation functional block is configured to consult the database to derive the use-by date of the first ingredient from the code, the concentration of an active agent in the first ingredient, and can determine that the first ingredient is not valid when the first ingredient has a wrong concentration of an active agent. The GUI functional block is responsive to the ingredient validation functional block to display an error message on the GUI when it is determined that the first ingredient is not a valid ingredient.

In some embodiments, a non-transitory medium storing computer-readable instructions, which when read and executed by at least one processor of a computing device, implement a method, including implementing a computerized GUI that provides a user of the computing device with an opportunity to specify a compounding formula for a composition to be prepared by subjecting a plurality of ingredients to a mixing cycle in a planetary mixer, wherein the mixing cycle includes a plurality of mixing steps, where each mixing step includes applying superimposed rotation and revolution movements to a container including two or more of the ingredients therein. Also included is consulting a database on the basis of the specified compounding formula to derive mixing parameters for each step of the mixing cycle associated with the specified compounding formula, receiving a first code generated by a code-reader reading machine-readable data on a first container holding a first ingredient, and processing the first code for determining if the first ingredient is a valid ingredient for a first mixing step of the specified compounding formula. If it is determined that the first ingredient is a valid ingredient, then the planetary mixer is enabled to perform the first mixing step of the plurality of mixing steps according to the determined mixing parameters for the first mixing step. The method includes receiving a second code input by the code reader in response to reading machine-readable data on a second container holding a second ingredient, processing the second code to determine if the second ingredient is a valid ingredient for a second mixing step of the specified compounding formula, and if it is determined that the second ingredient is a valid ingredient enabling the planetary mixer to perform a second mixing step of the plurality of mixing steps, including subjecting the first ingredient, the second ingredient and possibly additional ingredients to superimposed revolution and rotation movements according to the mixing parameters determined for the second mixing step.

In some embodiments can the method can include determining that either one of the first ingredient and the second ingredient is not valid when the first ingredient or the second ingredient is a wrong ingredient for the respective mixing step of the specified compounding formula, when either one of the first ingredient and the second ingredient has a use by date that has passed or when either one of the first ingredient and the second ingredient has a wrong concentration of active agent.

In some embodiments, a computer-implemented method for compounding using a planetary mixer, comprising: specifying on a GUI a compounded product to be prepared by mixing a plurality of ingredients in a planetary mixer, generating a first prompt on the GUI directing a user to scan a first container holding a first ingredient with a code-reader to read data on the first container, to generate a first code associated with the first ingredient. The method includes consulting a database on the basis of the first code and the specified compounded product to determine if the first ingredient is a valid ingredient for the specified compounded product, obtaining machine instructions for the planetary mixer for performing a first mixing step of a plurality of mixing steps for preparing the compounded product and applying the machine instructions to the planetary mixer to cause the planetary mixer to perform the first mixing step which includes subjecting a container holding the first ingredient and an additional ingredient to a superimposed rotation and revolution movements. The method includes generating a second prompt on the GUI directing the user to scan a second container holding a second ingredient with the code-reader to read data on the second container, to generate a second code associated with the second ingredient, consulting the database to determine if the second ingredient is a valid ingredient for the specified compounded product, obtaining machine instructions for the planetary mixer for performing a second mixing step of the plurality of mixing steps for preparing the compounded product and applying the machine instructions to the planetary mixer to cause the planetary mixer to perform the second mixing step which includes subjecting the container in which are placed the first ingredient, the second ingredient and the additional ingredient to a superimposed rotation and revolution movements. The method also includes disabling performance of the first mixing step or the second mixing step if the method determines that at least one of the first or second ingredients is not valid.

In some embodiments monitoring a lid sensor of the planetary mixer to determine whether the lid of the planetary mixer is open or closed and disabling execution of the second mixing step until the lid sensor indicates that the lid has been operated after completion of the first mixing step.

Back End Uses
Administrative Compliance and Record Management

To comply with regulatory bodies across different jurisdictions with respect to compounding compositions (e.g., pharmaceutical or cosmetical), one aspect is to have proper documentation that specify extra measures for uninterrupted progress of every compounding process. While proceeding with a compounding process using a standard documented set of compounding instructions is an important measure, it cannot be enough. In fact, the requirement for proper documentation needs to go beyond the actual compounding process but rather encompass steps prior and after compounding to ensure preparation quality and safety.

Figure 28:
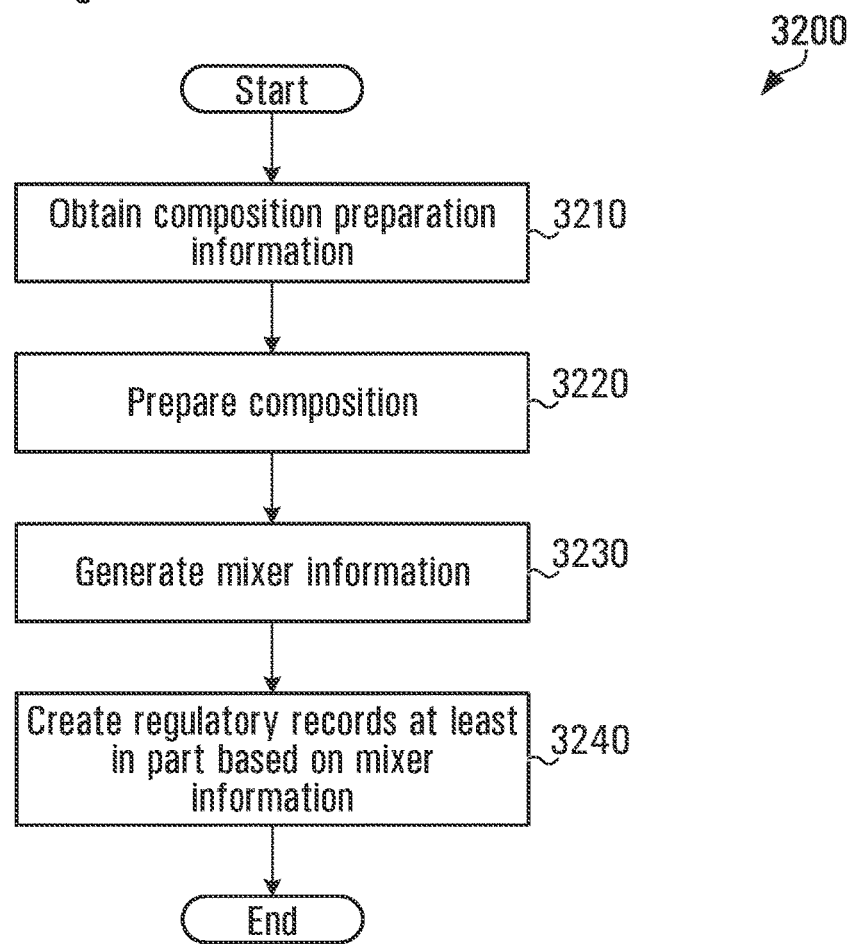
FIG. 28 is a flowchart of a process for generating regulatory records.

FIG. 28 is a flowchart of a process 3200 for managing records. The process starts by step 3210 wherein the operator, through user device 12, obtains obtaining composition preparation information. Generally, the compounding information are well-documented computer-readable files that can be communicated from a source (e.g., database on a server) to a requesting device (e.g., a user device). Furthermore, compounding information can be obtained from different sources and can reside on different locations. In one example, compounding information can be located on the database 19. In another example, compounding information can be located on the database 18. The obtained composition preparation information from step 3210, can be transmitted to a user device 12, converted to control messages via mixer control application 120 and sent to mixer for initiating the composition compounding process at step 3220. The mixer will in turn generate information regarding the assigned compounding process at step 3230 and in the form of a computer-readable file. In one example, mixer information during compounding can be in the form of a log file stored in the memory of the mixer 10. In another example, mixer information during compounding can be transmitted as a log file to the memory of the user device 12. The mixer information can be further combined with additional post-compounding information at step 3240 to create a regulatory record corresponding to the executed and successfully completed compounding process.

Figure 29:
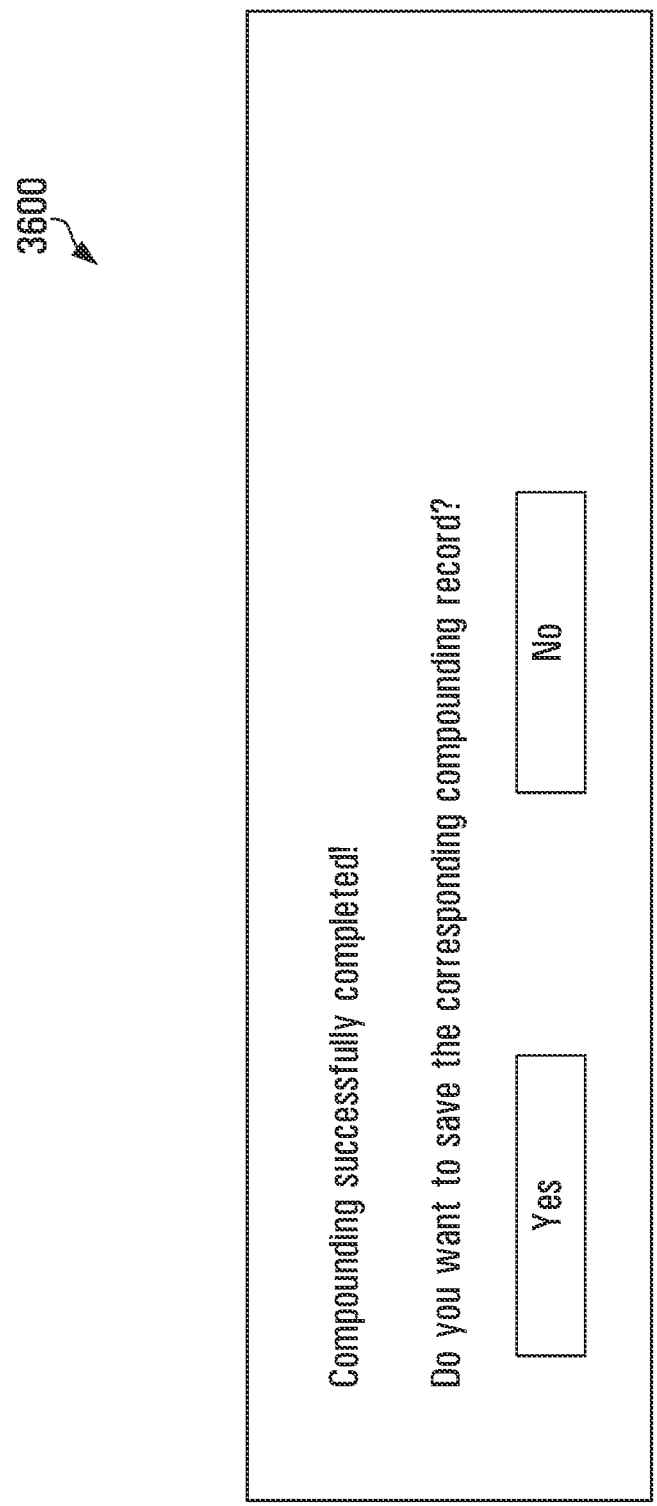
FIG. 29 illustrates a GUI on the user device that can appear during execution of the flowchart in FIG. 28.

Every time a composition is successfully compounded for a specific prescription using the planetary mixer, a unique regulatory record (like a summary report) known as a compounding record corresponding to the executed compounding process can be created. This corresponds to step 3240 of FIG. 28 where the regulatory record is created at least in part based on the information generated from the mixer 10. FIG. 29 is an example of a notification that can appear upon completion of a compounding process prompting the operator for saving the compounding record. In one example, the notification can appear on the mixer 10 screen display. In another example, the notification can appear on the GUI of the user device 12. The compounding record can be generated at the memory of the mixer 10 and can be transmitted to the memory of the user device upon interaction between user device 12 and mixer 10. The compounding record can be directly generated in the memory of the user device 12. The compounding records generated upon compounding completion for every composition can be further stored on a database (local or remote) and can be further consulted in future follow-ups, as required.

Items that can be included in a compounding record are:
Name of the individual to whom the compounded composition is prescribed (e.g., patient)
Commercial or assigned name and dosage form of the compounded medication
Reference to the master formulation record and/or SOP used for compounding
Total amount to be compounded
Name of all ingredients, the quantity of each ingredient, source of each ingredient, their lot number, compatibility and stability info and expiry date
Name of the persons (pharmacist, QC, etc.) that were involved in the compounding process
Labelling details; instructions can be name of medication, dosage, BUD, to-be-stored conditions, and prescription number corresponding to the medication
QC summary in case of any inconsistencies between the final compounded composition and what was expected using a master formulation record o
Storing compounding records even for those compounding events that went wrong (status message to be stored in at the end of each record: approved, rejected, discarded, off-spec, etc.)

Figure 26:
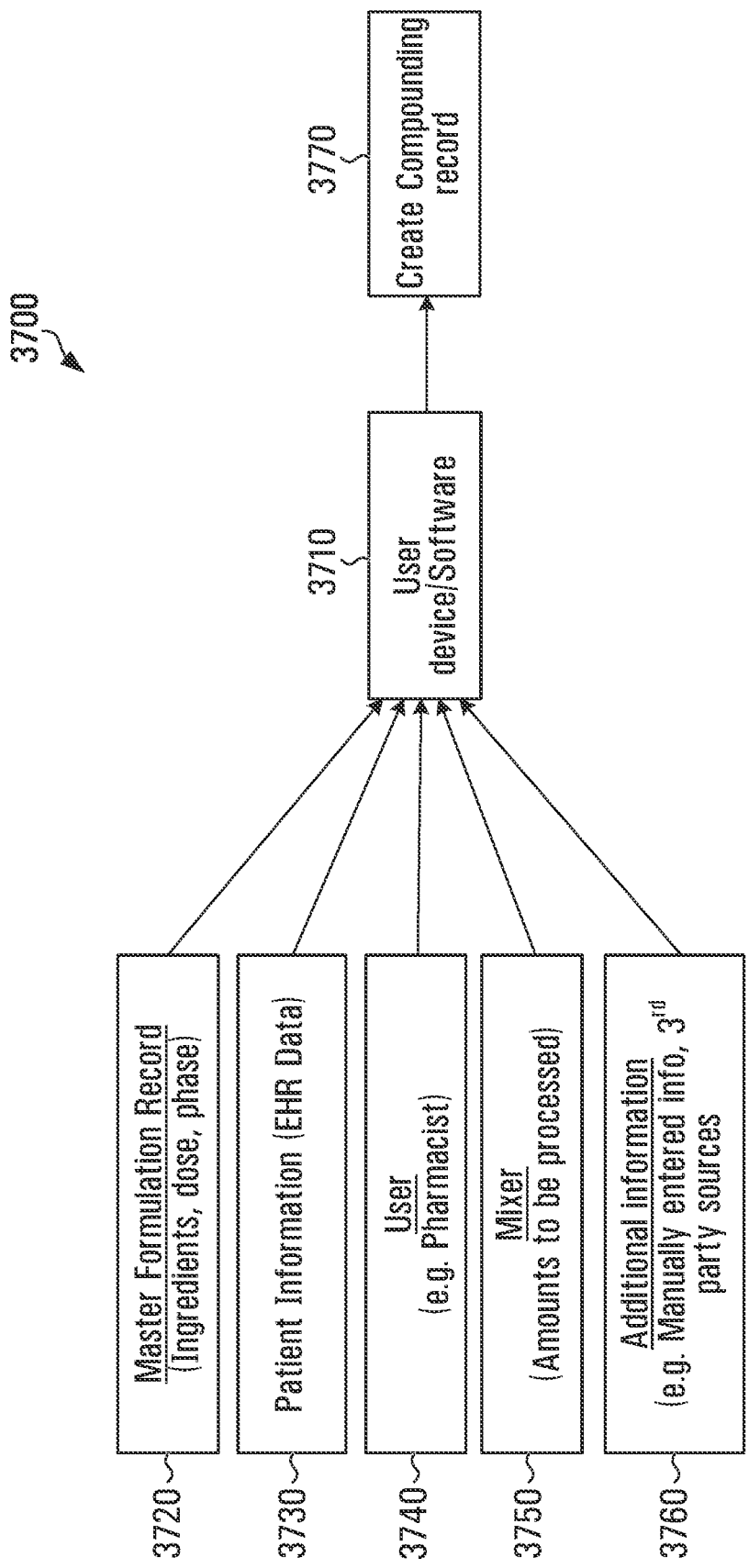
FIG. 26 shows the type of information used for generating regulatory records.

Generally, information within compounding records are obtained from a plurality of information sources. FIG. 26 shows that the user device 12 interacts with:
MFR database to obtain MFRs to obtain a list of information including ingredients, dosage, composition type and beyond-use date
Patient to obtain information including patient's name
Users or operators (e.g., pharmacists and pharmacy supervisors) to obtain their names for future follow-ups
Mixer 10 to obtain operating parameters
$3^{rd}$ party sources for additional information that could be optionally entered manually into the compounding record.

FIG. 30 is an example of a compounding record accessed through user device 12 and from a GUI perspective. The information contained in the compounding record are obtained from different sources as also explained in FIG. 26 to create a log-shaped file summarizing the entire compounding process and parameters that can be required for future references. In one example, the compounding record can include information on the composition that was compounded as well as the ingredients used along their sources. In one example, the compounding record can have hyperlinks through which details on parameters (including ingredients and sources of ingredients used) could be viewed in further details. In another example, the compounding record can include the master formulation record number or SOP number accessed and consulted prior compounding the composition. This will be useful for future references, wherein the repetition of the same compounding process can be required (refer to refill request section). In another example, the compounding record can include the names of the operators (e.g., pharmacists) who executed the compounding process through user device 12. In another example, a second review is done by a second user (e.g., a pharmacy supervisor) to double-check the overall compounding process execute and ensure no inconsistencies and therefore, a compounding record can include the name of the second reviewer for future references and follow-ups.

Creation and Use of Account Profiles

Figure 32A:
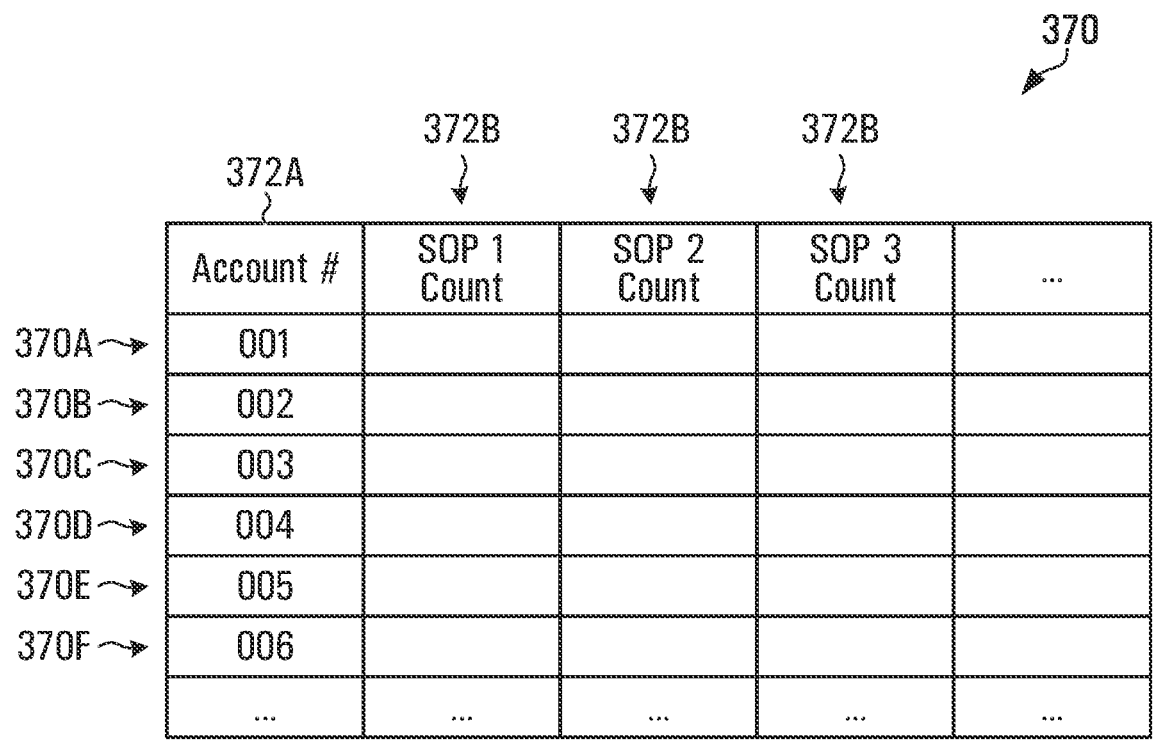
FIG. 32A illustrates a table for storing operating procedure information in association with account information.

The interactive program module 250 can be configured to track the frequency with which the SOP files are consulted or retrieved by each account holder. FIG. 32A shows a table 370 of records 370A . . . 370F, hereinafter referred to as a "usage table". Each of the records 370A . . . 3F0D includes a plurality of entries, in each of an account #field 372A and a plurality of SOP count fields 372B. For a given one of the records 370A . . . 370F, the entry in the account #field 372A is information corresponding to an account holder associated with that record, as previously described (e.g., it could be a unique account number or customer name or legal entity name). As for the SOP count fields 372B, each of these fields can pertain to a different SOP file that was requested by the account holder in question. Those skilled in the art will appreciate that the reference to a table is merely a conceptualization, as other organizational formats or data structures can be suitable and can thus be employed instead of a table. The usage table 370 can further store the times at which the various SOP files were requested by the various account holders.

Figure 32B:
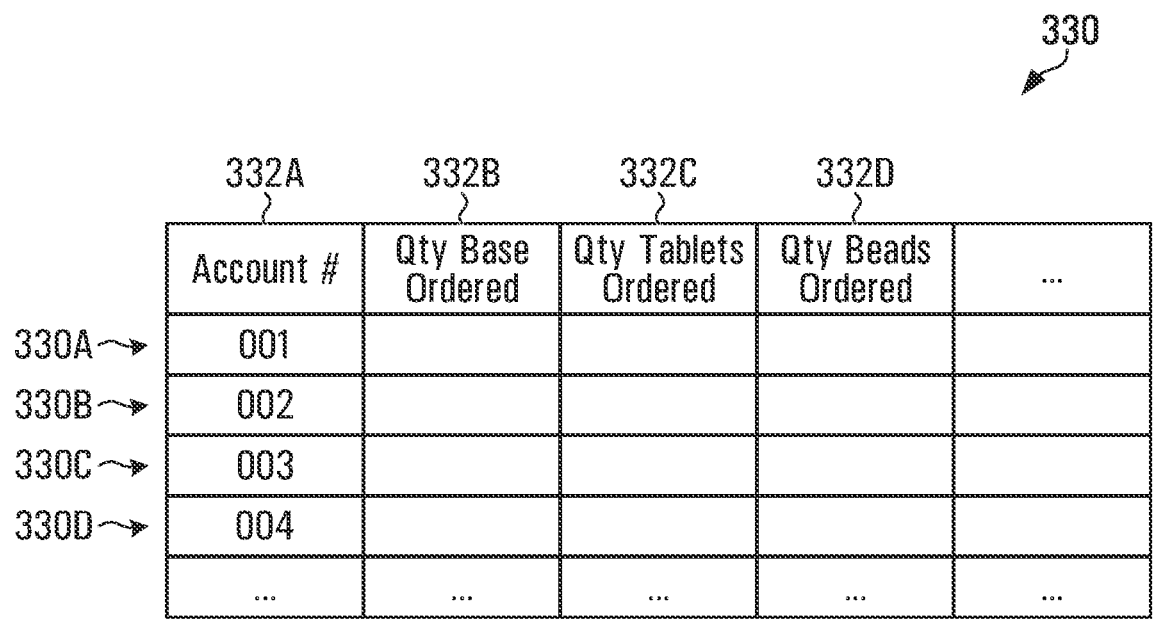
FIG. 32B illustrates a table for storing ingredient and quantity information in association with account information.

In cases where the entity that maintains the first server 16 is not only a supplier of SOP files for the mixer 10 but is also a supplier of ingredients used in mixing, additional information pertaining to the account holders is available to this entity. This additional information can also be stored in the first database 18. FIG. 32B shows a table 330 of records 330A . . . 330D, hereinafter referred to as a "sales table". Each of the records 330A . . . 330D in the sales table 330 includes a plurality of fields, including an account #field 332A and a plurality of purchased ingredient quantity fields 332B, 332C, 332C, 332E. For a given one of the records 330A . . . 330D, the entry in the account #field 332A is information corresponding to an account holder associated with that record, as previously described (e.g., it could be a unique account number or customer name or legal entity name). As for the purchased ingredient quantity fields 332B, 332C, 332D, 332E, each of these fields can pertain to a different item that has been purchased by the account holder in question.

Figure 31:
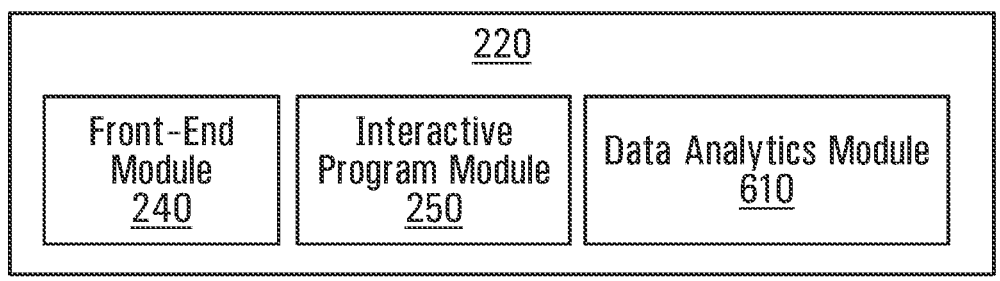
FIG. 31 is a block diagram showing example contents of the memory of the server, including a data analytics module.
Figure 33A:
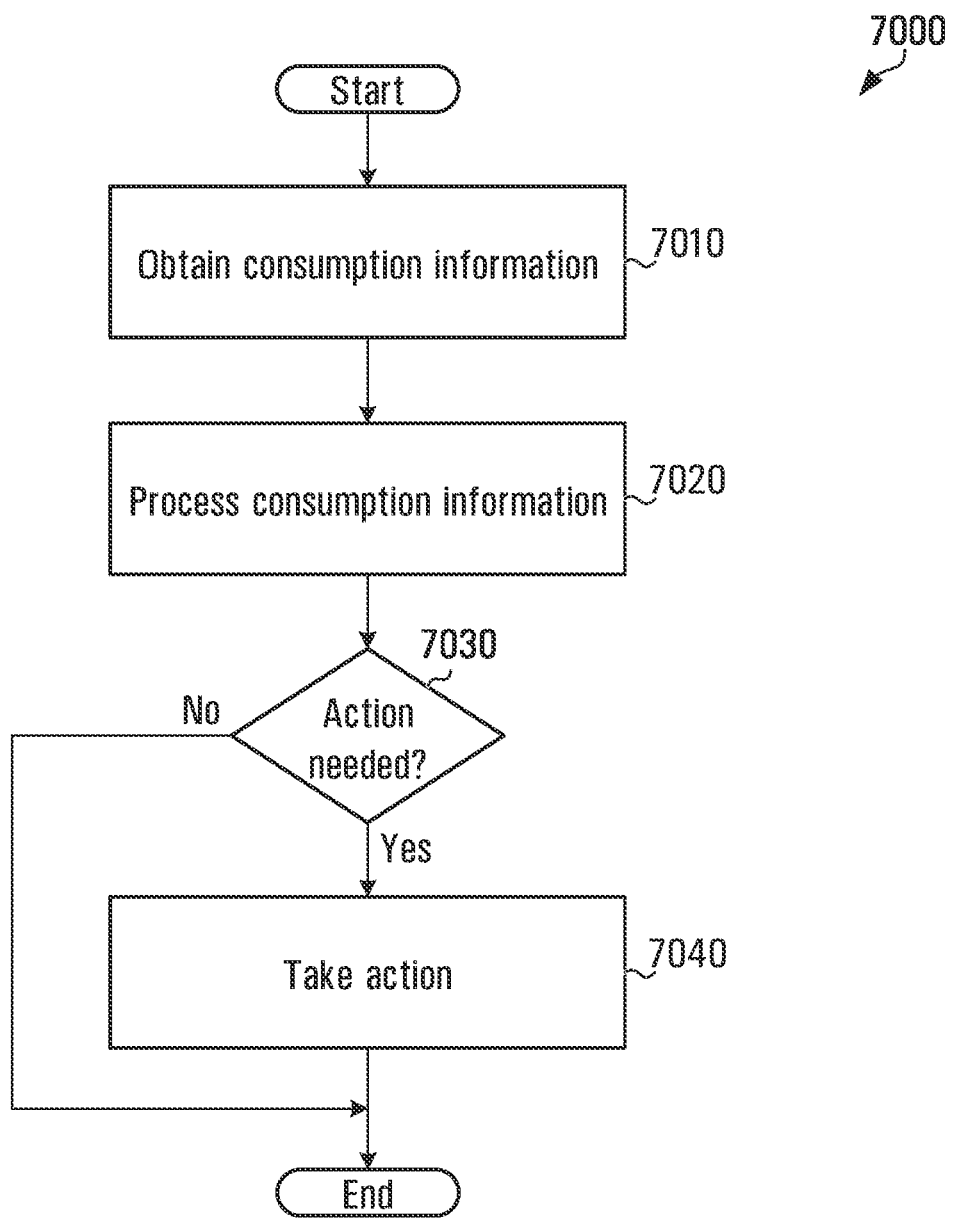
FIGS. 33A-B are flowcharts illustrating steps that can be taken in executing the data analytics module for inventory management.

The information in the credential tables 310 (FIG. 27) and the sales table 330 can have value in terms of data analytics and marketing. FIG. 31 shows a data analytics module 610 that can be implemented by the first server 16, namely as a result of the processor 210's execution of computer-readable instructions stored in the memory 220. The data analytics module 610 is configured to monitor the data at least in the credential tables 310 and the sales table 330, as further described below, and to carry out a process 7000 illustrated by FIG. 33A, performed for an account holder X.

Specifically, at step 7010 the data analytics module 610 obtains consumption information for at least one ingredient and for an account holder X, as further described below. This can be done in a number of ways, for example the consumption information can be obtained via data stored in the credential tables 310 and the sales table 330 of the first server 16 for an account holder X, but can also be obtained via data stored directly on the mixer 10 or data stored on the second database 19 of the second server 17 in other examples. In other examples, the consumption information obtained at step 7010 will need to include aggregate consumption information for multiple account holders—this is the case where multiple account holders use the mixer 10 within a single pharmacy such that all account holders effectively share the same inventory. In another example, the consumption information obtained at step 7010 can need to include aggregate consumption information across multiple mixers 10—this is the case where multiple mixers 10 are being used within the same pharmacy and all mixers 10 share the same inventory. In other words, in some instances a distinct account can be created for the aggregate of the individual account holders (e.g., users) using the mixer 10—this would be the case where multiple users use the same mixer 10 within the pharmacy and therefore monitoring consumption across all the users is needed for proper inventory management. A distinct account can also be created for the aggregate of mixers 10 in the pharmacy—this would be the case where multiple mixers are being used within one pharmacy, potentially with multiple account holders each using each one of the mixers 10, and therefore monitoring consumption across all mixers is needed for proper inventory management. The account can be set in any other suitable way, depending on whether all users share, or not, the same inventory, whether all mixers share, or not, the same inventory, etc.

In a second step 7020, the data analytics module 610 processes the consumption information and then determines at step 7030 whether an action is needed. The processing can be done in several ways and involve a number of steps, as further described below. For example, the processing at step 7020 can involve determining an expected consumption for an account holder X based on past orders and/or current inventory stocks in the pharmacy where the mixer 10 is used, and then assessing at step 7030 whether there is a discrepancy between the expected consumption for the account holder X and an actual consumption for the account. Alternatively, the processing at step 7020 can involve comparing the consumption information obtained at step 7010 with a threshold inventory quantity for each ingredient in the inventory, such threshold being set by the account holder X. If the data analytics module 610 concludes at step 7030 that no action is needed, the process 7000 ends. If the data analytics module 610 concludes at step 7030 that an action is needed, the data analytics module 610 then takes an action at step 7040.

Figure 33B:
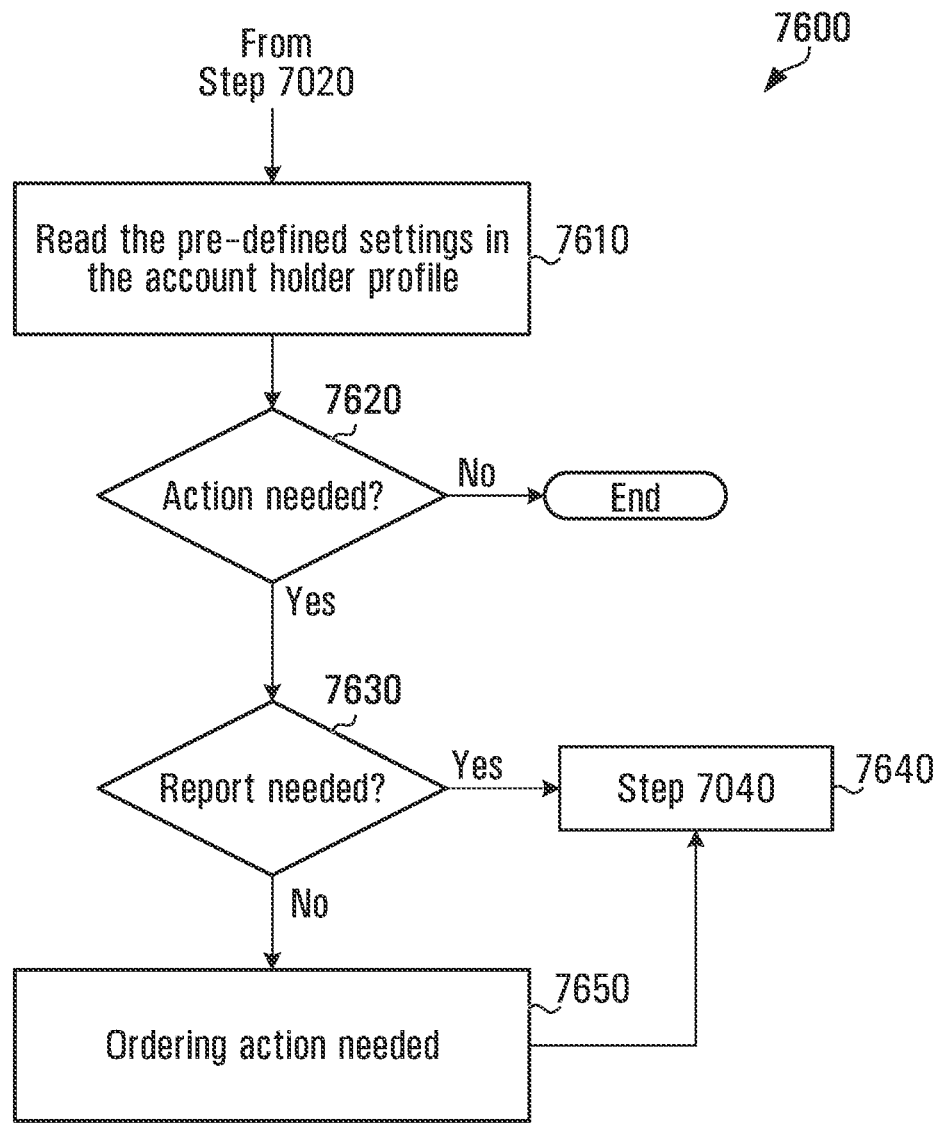

At step 7030, referring to FIG. 33B, a setting saved in the profile of the account holder X can be a read step 7610 that then determines whether an action needs to be taken at step 7620 and what the action should be. For example, the account holder's profile can be set such that no action will be taken at step 7620, whether or not there is any discrepancy between the expected consumption and the actual consumption for the account holder X, or whether the consumption information obtained at step 7010 is within the threshold inventory quantity for each ingredient in the inventory.

The granularity with which the purchased ingredients are designated by the purchased ingredient quantity fields 332B, 332C, 332D, 332E depend on the record keeping practices of the supplier. At a very coarse level, the purchased ingredients designated by the purchased ingredient quantity fields 332B, 332C, 332D, 332E can be categorized as base, chemical, color, flavor, oil, excipient powder, tablets and capsule, for example. At a finer level of granularity, each of the categories could be expanded, in some cases down to the molecular level (e.g., Acesulfame Potassium, Acetaminophen, Acetazolamide, etc.). The number of purchased ingredient quantity fields 332B, 332C, 332D, 332E can be very large when it is desired to keep detailed records on the purchasing history of account holders. The sales table 330 can further store the purchasing timeline of the various items purchased by the various account holders. The credential table 310 and the sales table 330 could be merged, as each includes a respective account #field, which could refer to the same account holder.

The account holder's profile can be set such that at step 7040 a report is generated and communicated to the account holder X, regardless of whether there is a discrepancy between the expected consumption and the actual consumption for the account holder X. The report can include an aggregate of the consumption information obtained at step 7010 and be communicated to the account holder X at any suitable time interval (e.g., once a day, once a week, once a month, etc.). The report can include a list of ingredients that have been used/consumed over the prescribed time interval, which mixer 10 has been used, etc. The report can be communicated to the account holder in any suitable manner—for example the report can be communicated to an email address or phone number associated with the account holder, or in any other suitable manner. The report can also be delivered to the account holder directly via the user device 12 and the account holder X can then use the report to manage the inventory.

In another example, the account holder's profile can be set such that the action is to communicate to the account holder X the remaining quantities of ingredients in the inventory of the account holder X. This can be achieved based on the consumption information obtained at step 7010, the data analytics module decreasing the quantity of the ingredients in the inventory based on a quantity of ingredient extracted from the consumption information. This requires some knowledge by the data analytics module 610 of the initial quantities of the various ingredients in the account holder's stock, which could be inputted directly by the account holder X or alternatively the data analytics module 610 could extract this information from the ingredient table 2600 (e.g., the inventory quantity field 2602E) of the database 19 (as further described in connection with FIG. 34). In communicating the remaining quantities of ingredients in the inventory of the account holder X, the data analytics module could highlight remaining quantities that are below a pre-determined threshold, for example the one found in the minimum inventory quantity field 2602L of the ingredient table 2600 in the second database 19.

In another example, the account holder's profile can be set such that the action is an ordering action based upon the processing of the consumption information at step 7020. As discussed, the processing at step 7020 can involve determining whether there is a discrepancy between the expected consumption and the actual consumption for the account holder X or, alternatively, comparing the consumption information obtained at step 7010 with a threshold inventory quantity for each ingredient in the inventory set by the account holder X. Any other suitable processing logic could also be performed at step 7020 however the outcome is always to identify an ingredient, or a list of ingredients, for which an inventory quantity is running low or likely to run low (e.g., based on the frequency of orders for the account holder X, etc.). In this case, the action at step 7050 can include automatically placing an order for the ingredient or list of ingredients and communicating a notification to the account holder X to advise him of the order. Alternatively, the ordering action at step 7050 can include generating a pre-order for the ingredient or list of ingredients and communication the pre-order to the account holder X for approval, modification or cancellation.

Figure 33C:
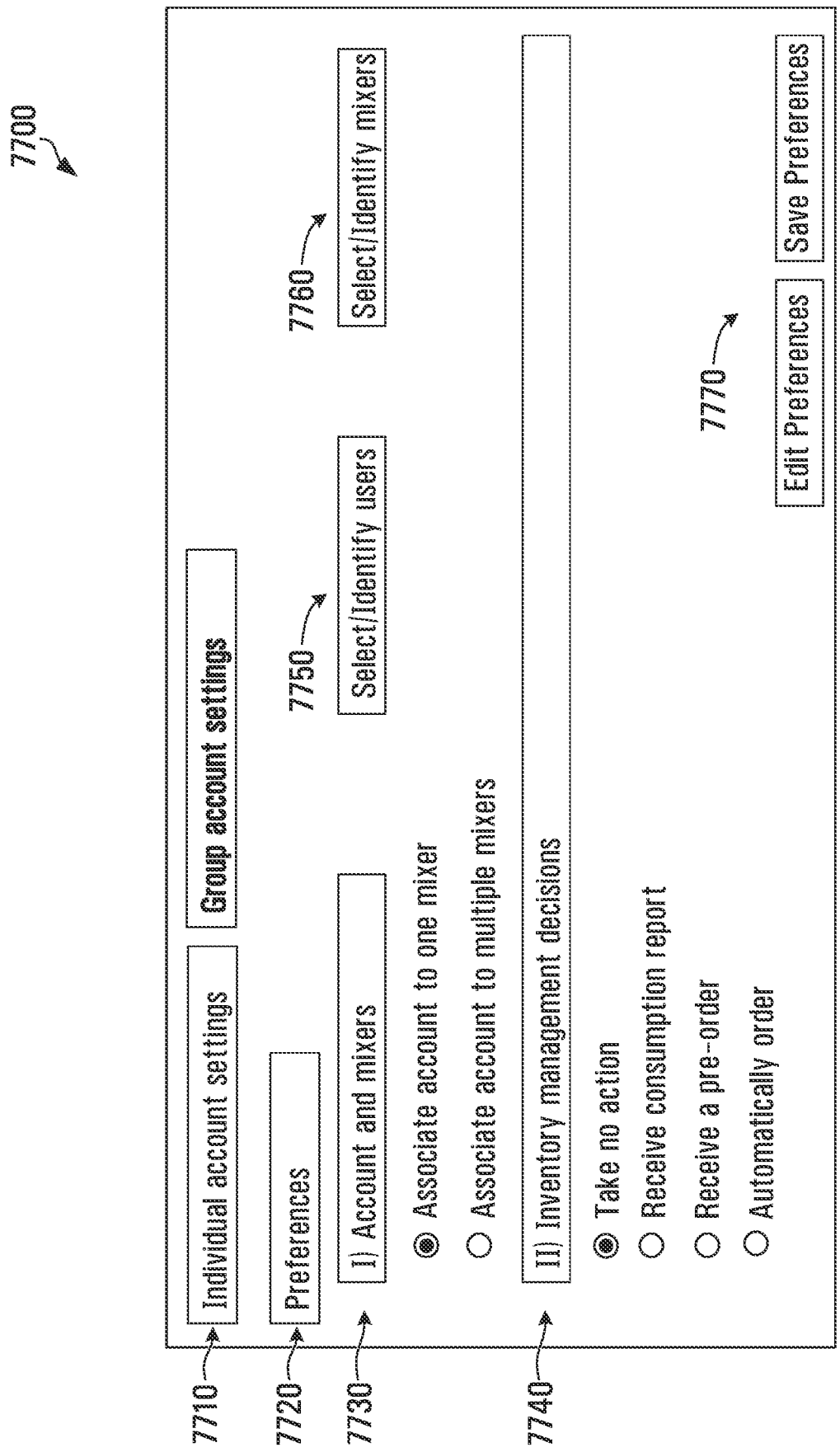
FIG. 33C illustrates a GUI on the user device that can be used to define the actions taken during execution of the flowchart in FIG. 133A or 133B.

The account holder's profile and account holder's profile setting serve at least two purposes: i) define account holders and interactions between account holders and mixer(s) and ii) define an action to be made by the account holder(s) with respect to inventory management. The account holder's profile and account holder's profile setting will now be described referring to FIG. 33C wherein an example of a GUI 7700 is shown that manages accounts setting and their preferences with respect to the action to be taken according to FIG. 33A or 33B. The account holder's profile can have separate sections for different account type as shown in 7710. The account can be defined either for an individual (one account to be accessed by one user) or a group of individuals (one account to be accessed by multiple users). An individual can have its own account and/or be a member of group accessing a group account as well. This can be the case when an account holder performs a composition compounding independently but supervises the composition compounding process performed by another user. In one example the preferences menu 7720 of the GUI has two sub-menus, an account and mixers sub-menu 7730 and an inventory management sub-menu 7740. account and mixers sub-menu 7730, either one of the individual account or the group account can be able to define various account settings. In one example, via the sub-menu 7730 the account holder can be prompted via an input object 7750 to identify at least one user (e.g., person using the mixer(s) 10 within the pharmacy) that should be associated with the account. Via an input object 7760 the account holder can also be prompted to identify at least one mixer that should be associated with the account. In another example, via the sub-menu 7740 the account holder X can be prompted to select an inventory management functionality to implement the process 7600 of FIG. 33B, For example, the account holder X can specify via various input objects whether the account holder X does not wish to use any inventory management function, whether the account holder X wishes to be provided with consumption reports, or whether the account holder X wishes to use the system to receive pre-orders or even communicate orders on behalf of the account holder X as per FIGS. 33A and 33B. The preferences menu 7720 can be edited and/or saved via the input objects 7770.

Analysis of User Behavior

Figure 33D:
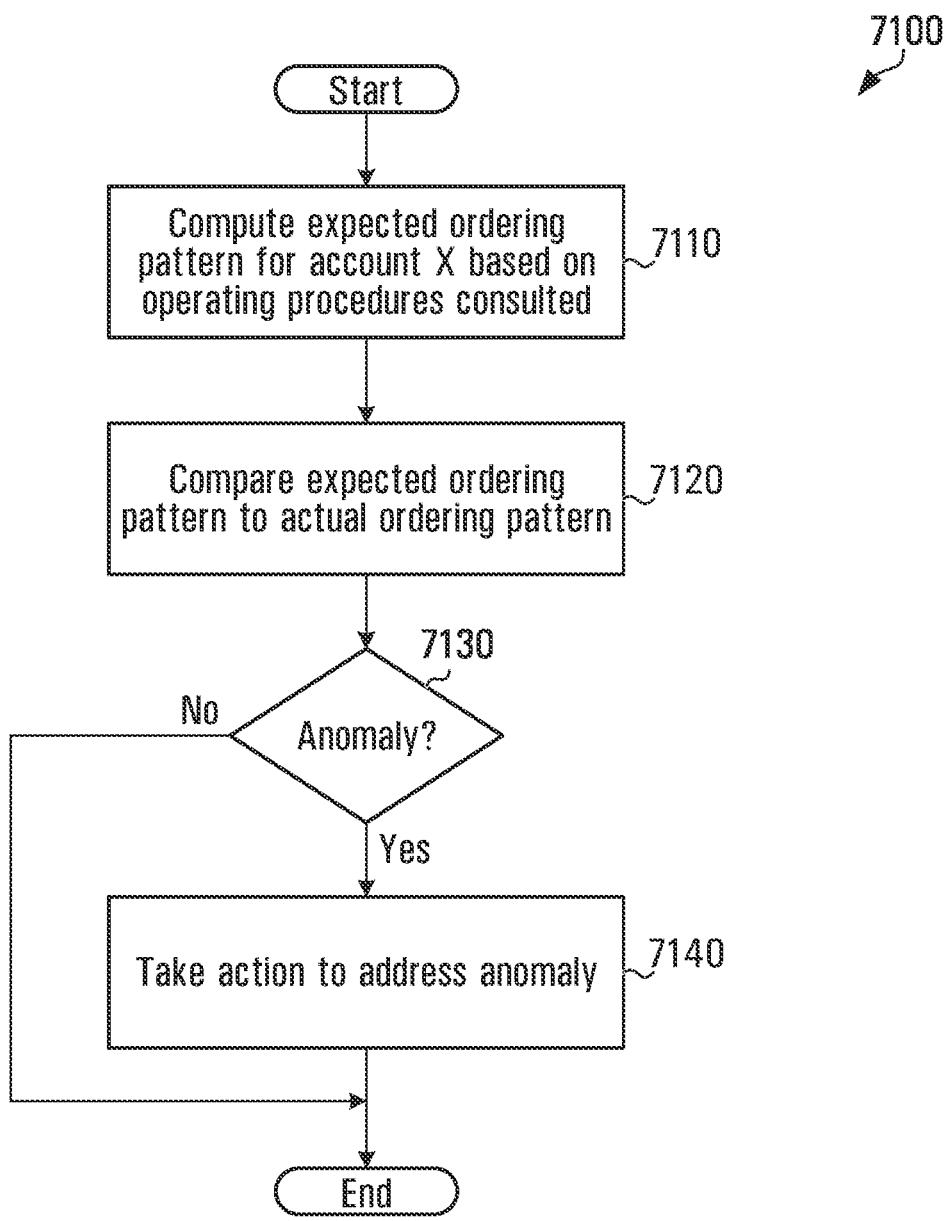
FIGS. 33D-H are flowcharts illustrating steps that can be taken in analyzing user behavior.

FIG. 33D illustrates a specific embodiment of the process 7000, namely process 7100, in which the consumption information is derived at least in part based on expected and actual ordering patterns for an account holder X. Ordering patterns could be defined as the pattern with which account holder X orders his/her required ingredients. An example of ordering patterns includes ordering a specific quantity on a timely basis (e.g., every week, month, quarter, etc.). Specifically, at step 7110, the data analytics module 610 computes an expected ordering pattern for account holder X. This can be done by consulting the usage table 370 of the first database 18 which, it will be recalled, tracks the frequency with which the SOP files are consulted by each account holder. As part of this step, the data analytics module 610 determines which SOP files were requested. The data analytics module 610 also consults, for example, SOP table **350\*\*, which indicates the quantities of ingredients associated with each operating procedure. This allows the data analytics module 610 to estimate or predict that an ingredient or set of ingredients should have been purchased by the account holder, if the steps in the requested SOP files were actually carried out; this is referred to as the "expected ordering pattern". While reference is specifically made here to the consultation of SOPs by the data analytics module 610, in other examples other files stored on or otherwise accessible via the first database 18** could be accessed to track the frequency with which the SOP files are consulted, such as Master Formulation Records, as will be further defined below, etc.

Of note, the process 7100 can start in several ways and at varying, constant or not constant, time intervals—for instance, step 7010 can be performed at regular, pre-determined time intervals that could be set by the account holder X. In some example, the assessment can be performed once a week, once a day or even several times a day to ensure that the account holder X has enough quantity of the relevant ingredients in stock to run the SOPs consulted by the account holder. The data analytics module 610 can track the frequency of SOP consultation for all the SOPs within the SOP table 350 that the account holder X has accessed at least once. In other examples, the process 7100 can start following a specific action by the account holder X—for example when the mixer 10 is turned on, when the mixer 10 is turned off, when the account holder X is placing an order with the entity that control the first server 16 or when the account holder completes the performance of a SOP on the mixer 10. In this latter case, at step 7110 the data analytics module 610 cannot track the frequency of SOP consultation for all the SOPs within the SOP table 350, but only for the SOP that was last performed on the mixer 10 by the account holder X.

At step 7120, the data analytics module 610 compares the expected ordering pattern to the actual history of orders placed by the account holder, as obtained from the purchased ingredient quantity fields 332B, 332C, 332C, 332E in table 330. As part of this step, the data analytics module 610 determines, for example, the extent to which the account holder has ordered, within a period of time (e.g., the last 6 months, the last month, etc.) the ingredients that should have been purchased by the account holder as determined at step 7110.

At step 7130, the data analytics module 610 determines whether there is an "anomalous ingredient supply condition". This could involve comparing, and assessing a level of discrepancy between, the ordered ingredients and the expected ordering pattern, for one or more ingredients. For this purpose, arithmetic or statistical techniques could be used. If there is no anomalous ingredient supply condition, no specific action needs to be taken. However, if there is an anomalous ingredient supply condition, such as ingredients that were purchased in a quantity less than would have been expected based on the expected ordering pattern, the data analytics module 610 proceeds to step 7140. At this stage, the data analytics module 610 can prompt the account holder to order the ingredient, or plurality of ingredients, or can generate an alarm message. This alarm message can be sent to the entity that controls the first server 16, or to any third party, signaling the anomaly. This could then result in a sales call or other offer being electronically triggered and delivered to an address associated with the account holder X. Alternatively, the data analytics module 610 can also automatically place an order with the entity that controls the first server 16 and then notify the account holder X that an order has been placed. The action that will be taken at step 7140 will be reliant upon the setting read in the profile of the account holder X at step 7610 and that has been selected by the account holder via the GUI of FIG. 33C.

Without knowledge that the mixer 10 was used to carry out the operating procedures and without knowing how many times the steps in the SOP files were performed, the knowledge gained by the data analytics module 610 can be imperfect. However, if the mixer 10 itself is configured to store the SOP table 350 and is also configured to track the rate at which different SOP files are carried out, and if this information is fed back to the data analytics module 610 (e.g., over the data network 14), this can be a powerful tool to estimate the replenishment needs of the account holder and/or can provide new marketing opportunities for the supplier of ingredients. While the data analytics module 610 can be on the server 16, is need not be the case and the data analytics module 610 can operate directly at the level of the user device 12 or the mixer 10 in some cases. In other words, both stand-alone and network-enabled mixers 10 can implement the above functionality and can be used to estimate ingredient consumption based on SOP access for an account holder X.

Figure 33E:
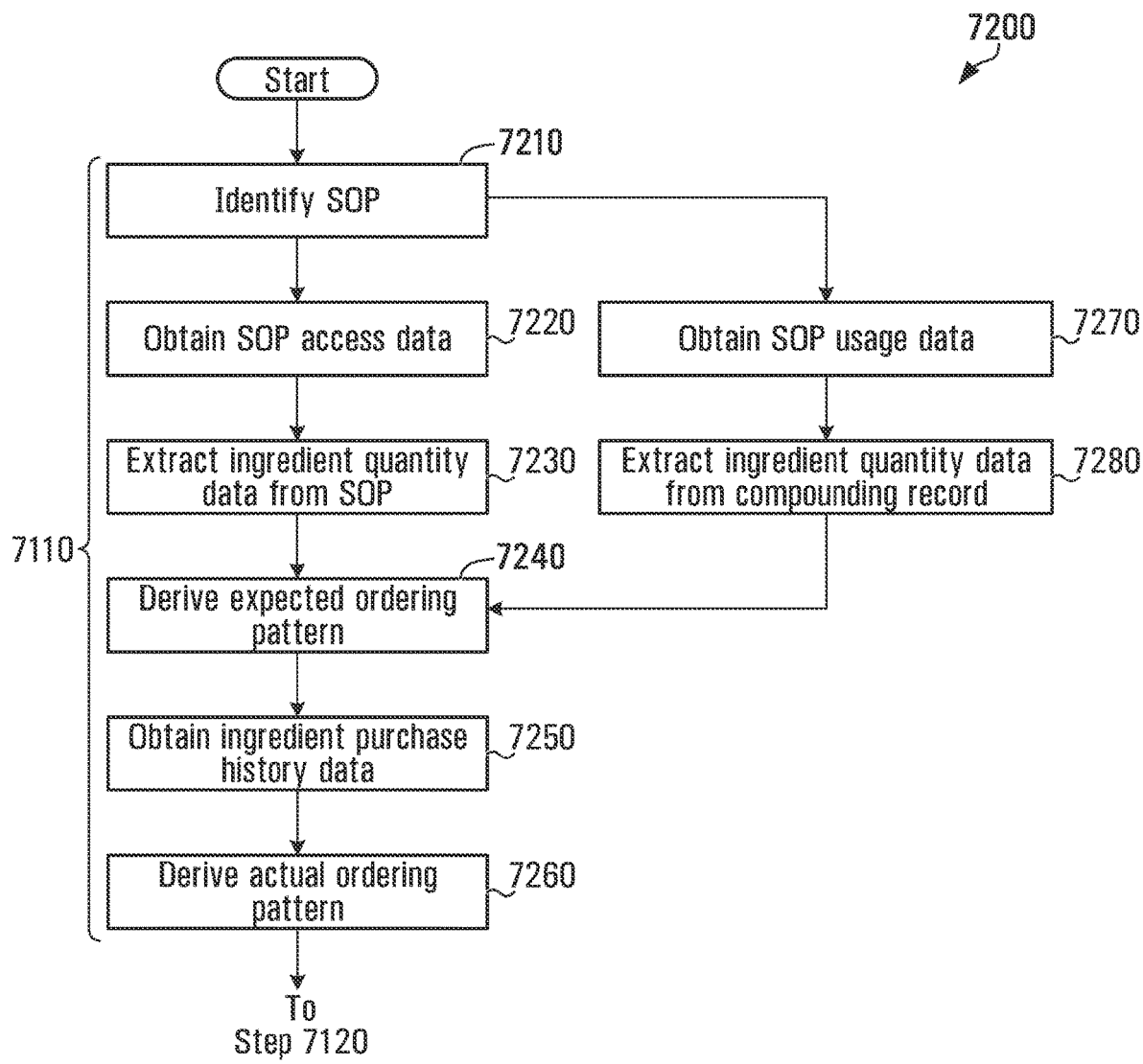

FIG. 33E shows the various sub-steps involved at step 7110 (e.g., process 7200) in accordance with one embodiment. At step 7210 the data analytics module first identifies at least one SOP within the SOP table 350 to compute the expected ordering pattern. At step 7220 the data analytics module 610 obtains access data for the at least one SOP identified at step 7210, that is the number of times the at least one SOP has been accessed/consulted by the account holder X. At step 7030, the data analytics module 610 then extracts ingredient quantity data from the at least one SOP identified at step 7210—in other words, for each one of the ingredients listed in the at least one SOP, the data analytics module identifies a quantity, or nominal quantity (in weight or volume) for each one of its ingredients. The ingredient quantity data extracted at step 7230 is therefore representative of the quantity of ingredients needed by the account holder X to complete/perform the SOP identified at step 7210 on the mixer 10. At step 7240, the data analytics module derives the expected ordering pattern at least in part based on the ingredient quantity data and the SOP access data. That is, for the at least one SOP identified at step 7210, the data analytics module 610 can estimate the quantity of ingredient(s) consumed per unit of time (e.g., day, week, month) according to the frequency of consultation of the SOP by the account holder X. It is assumed that each time the SOP is consulted by the account holder X the SOP is performed by the account holder X, which may or may not be accurate. At step 7250 the data analytics module 610 obtains ingredient purchase history data by consulting the actual history of orders placed by the account holder X, as obtained from the purchased ingredient quantity fields 332B, 332C, 332C, 332E in table 330. The data analytics module 610 can then derive the actual ordering pattern at step 7260 by estimating the quantity of ingredients ordered per unit of time (e.g., day, week, month) by the account holder X. The data analytics module then proceeds to step 7120 where the expected ordering pattern and actual ordering patterns are compared—in one example the comparison is performed over the same unit of time for a given mixer 10 however in other examples the comparison can also be done by using data aggregated for multiple mixers and/or multiple users of a given mixer within a pharmacy.

As a result of the assumption that each time the SOP is consulted by the account holder X the SOP is actually performed by the account holder X, the identification of an anomaly at step 7130 cannot accurately represent the ordering needs of the account holder X—this would for example be the case for the account holder X that consults multiple SOPs in an attempt to find a suitable SOP, but only effectively perform one of them. There are various manners in which such limitation can be mitigated. For example, every time a SOP is accessed by an account holder via a GUI the GUI can prompt the user to confirm that the SOP being consulted is/will be used by the account holder—in this manner the input received by the account holder via the GUI can be used to filter out some of the SOP access data and effectively convert SOP access data into corresponding SOP usage data. In this manner the SOP access data obtained at step 7220 more accurately reflects the ordering needs of the account holder X.

Alternatively, instead of relying on SOP access data at step 7220 the data analytics module 610 can also rely on SOP usage data at step 7270. The SOP usage data can be obtained in several ways—for example, the SOP usage data can be obtained directly from SOP count data from the SOP usage table 370. In this case, every time a SOP has been performed/completed on the mixer 10, the mixer 10 can automatically output a signal that is communicated to the database 16 via the network 14 which will then implement a +1 count increment in the SOP count field 372B of the SOP usage table 370 associated with the SOP that has been performed/completed on the mixer 10. Alternatively, every time a SOP has been performed/completed on the mixer 10 the account holder can be prompted via a GUI to confirm that the SOP has been performed/completed on the mixer 10, in which case the SOP count field 372B of the SOP usage table 370 is updated as described above.

In another example, the SOP usage data can be derived from a Compounding Record, as further defined below, that is generated by the mixer 10 upon completion of a SOP. Ingredient quantity data can be then be extracted from the compounding record at step 7280—while the ingredient quantity data extracted from the compounding record will be identical to the ingredient quantity data extracted from the SOP in most cases, in the instances where the SOP includes nominal quantities (e.g., several actual quantities can effectively be used in the SOP as long as they are multiple of the nominal quantities), the ingredient quantity data extracted from the compounding record can be more accurate than the one extracted from the SOP. The expected ordering pattern is then derived at step 7240 however this time based upon actual SOP usage data, rather than SOP access data.

Figure 33F:
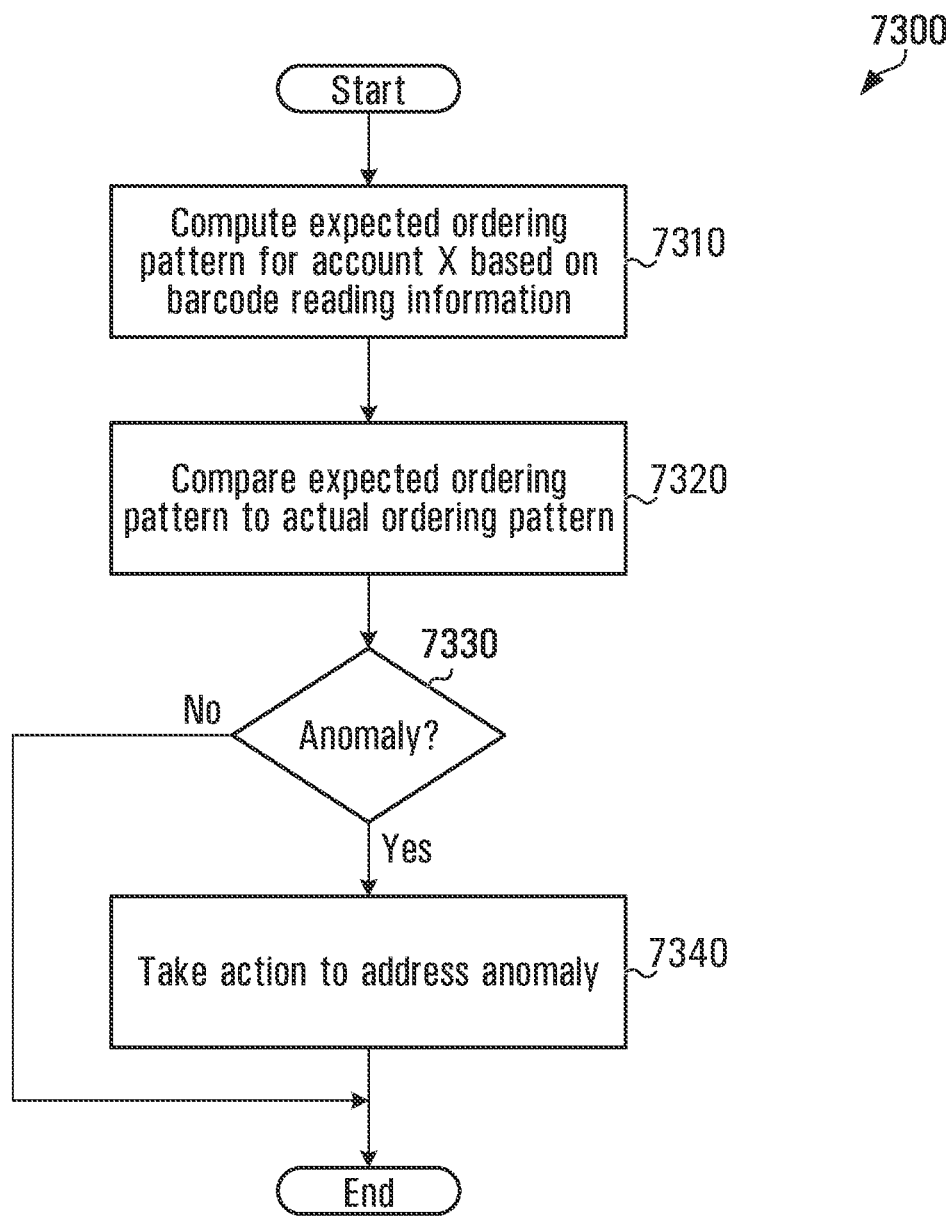

FIG. 33F shows a process 7300 in which the consumption information is still derived at least in part according to expected and actual ordering patterns for an account holder X, with the expected ordering patterns for the account holder X computed based upon bar code reading information at step 7310. Process 7400 can start following a specific action by the account holder X—for example when the account holder scans the bar code or QR code as he is preparing for compounding using an SOP. In other examples, the bar code reading information can also include information pertaining to a bar code count, as further described below, and a quantity of ingredient—this would be the case for example when the container 1004 is a single-use container and therefore when the entire quantity of the ingredient within the container 1004 is to be used each time the bar code or QR code 1003 is read by the data entry device 1000.

Figure 33G:
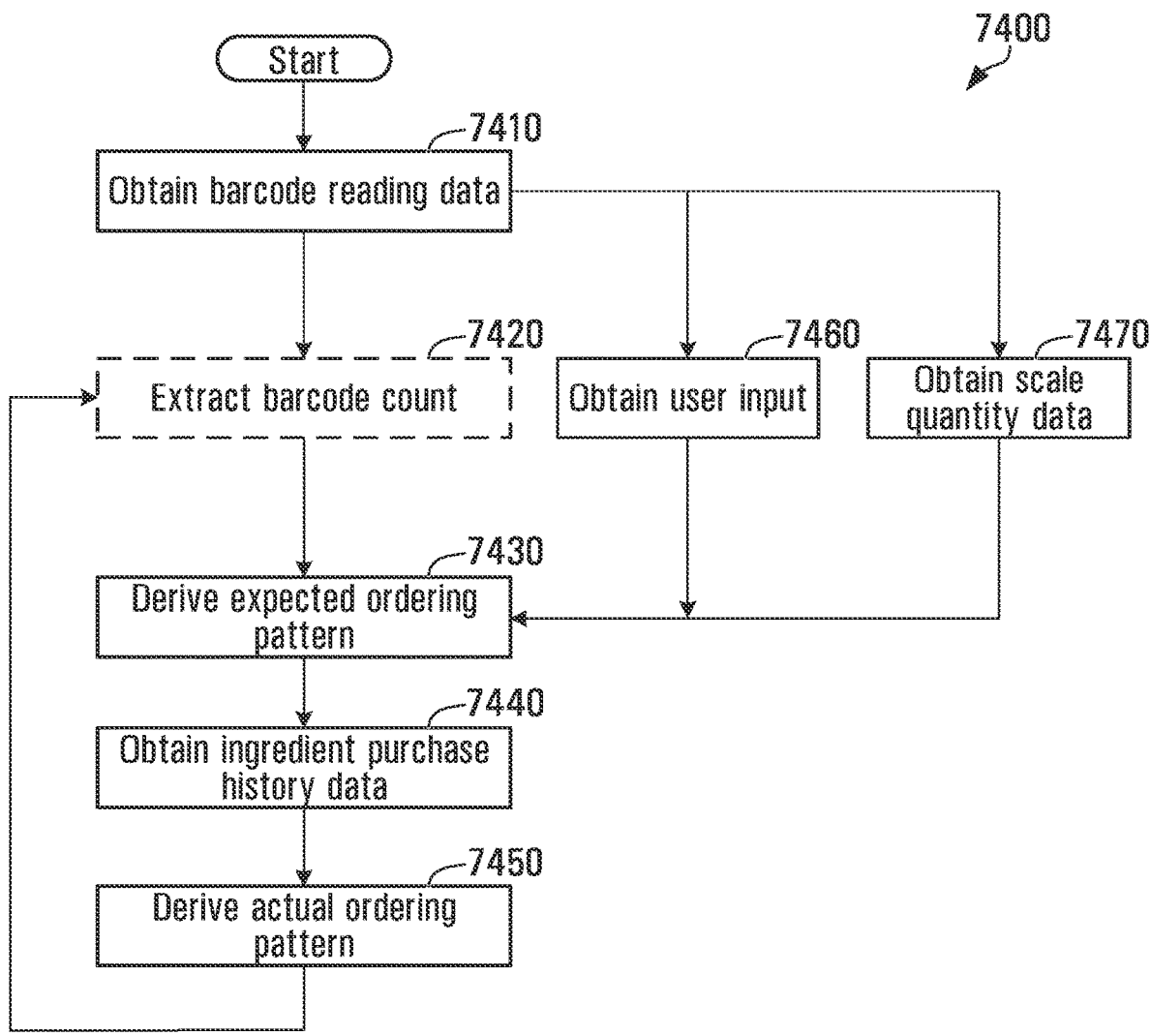

FIG. 33G shows the various sub-steps (e.g., process 7400) involved at step 7310. At step 7410, the data analytics module 610 obtains bar code reading data. At step 7420, the data analytics module 610 may extract a bar code count (e.g., a number of times that a given bar code has been read by the data entry device 1000 on the container 1004—this could be useful for example where multiple containers 1000 with each the same quantity of the same batch of the same ingredient are received by the account holder and the containers all share the same bar code) from the bar code reading data and then derive the expected ordering pattern at step 7430 at least based upon the bar code count. In some cases, the expected ordering pattern can be derived only based upon the bar code count—this will be the case where the bar code is associated with a specific ingredient quantity in the database 1002 in which case the data analytics module 610 can estimate the quantity of ingredient(s) consumed per unit of time (e.g., day, week, month) using the bar code count extracted at step 7420. In other examples, specifically the ones where the bar code is not associated with a specific ingredient quantity in the database 1002, additional quantity data will need to be obtained to derive the expected ordering pattern at step 7430. For example, the account holder X can be prompted at step 7460 to input a quantity for the ingredient for which the bar code reading data was obtained at step 7410, or alternatively a scale quantity data can be obtained by the data analytics module 610 at step 7470. FIG. 22 shows a scale 1350 that is used to weigh the contents of a container 1360 and transfer the weight readouts via network or manually to user device 12. The user device 12 can in turn communicate over network and possibly through mixer control application to transmit the weight data to mixer or store ingredients data and their respective weights on the database for further generation of records, if applicable. In these two alternatives, while the bar code reading data obtained at step 7410 is necessary in that it enables the data analytics module 610 to properly identify an ingredient, step 7420 is optional since the bar code count is not associated with any ingredient quantity. Much like the embodiments above, the expected ordering patterns derived at step 7430 correspond to the quantity of ingredient per unit of time (e.g., day, week, month) by the account holder X. The data analytics module 610 can then obtain ingredient purchase history data at step 7440 by consulting the actual history of orders placed by the account holder X, as obtained from the purchased ingredient quantity fields 332B, 332C, 332C, 332E in table 330. and derive an actual ordering pattern for the account holder X at step 7450.

Figure 33H:
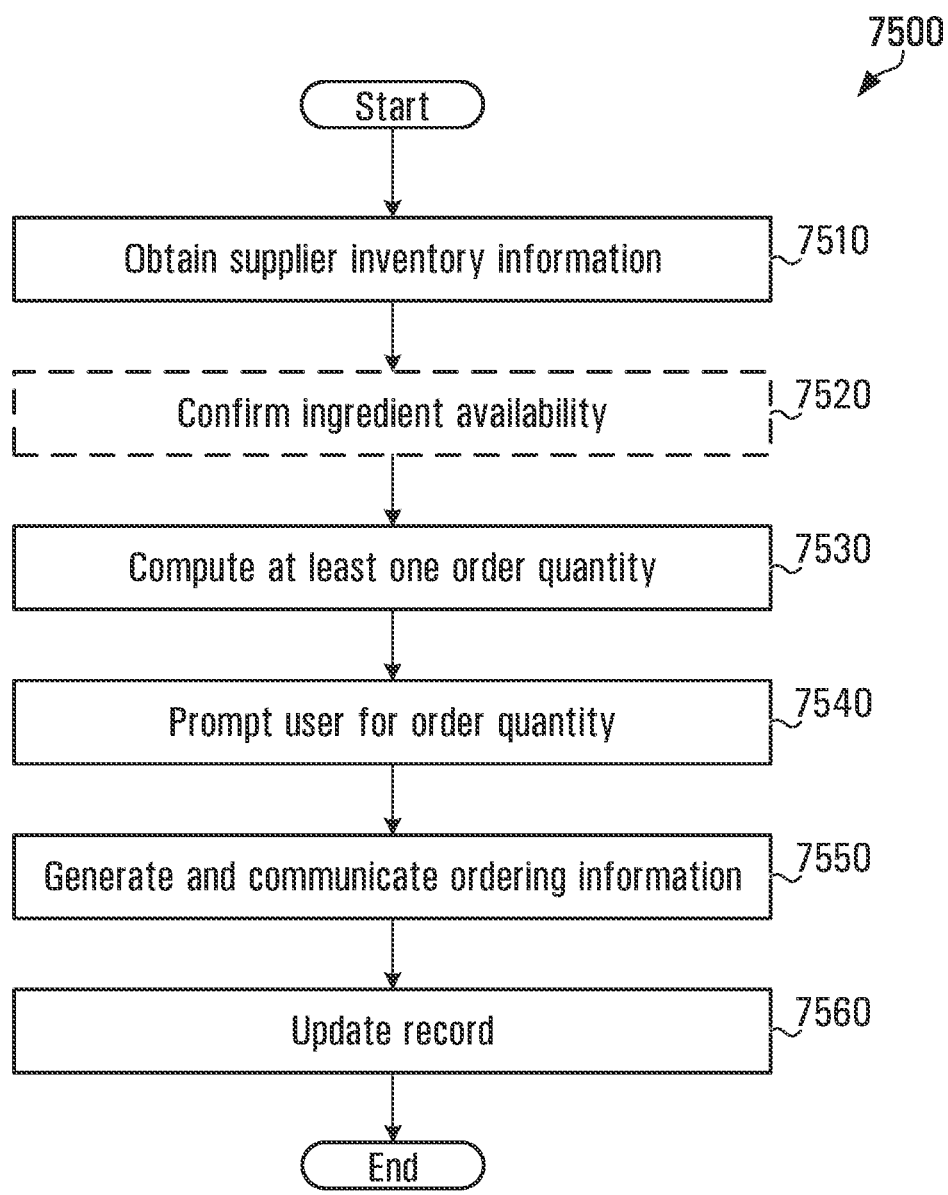

Once the actual ordering patterns is identified, in one embodiment one action is to place new orders for new batches of ingredients. FIG. 33H shows process 7500 for completing a new order for ingredients. In a first step 7510 the data analytics module 610 obtains supplier inventory information. The supplier inventory information can include available ingredients, expiry date, batch volume, etc. In one example, the data analytics module 610 can query suppliers' ingredient databases to obtain information regarding ingredients that need to be ordered. Based on the results of queries on suppliers' database, the availability of to-be-ordered ingredients can be confirmed at step 7520 by comparing the ingredients ordering patterns derived through any of the methods disclosed against the ingredients available quantities derived from suppliers' information database. In case the primary supplier does not have enough inventory on specific ingredient(s) to fulfill an order, the data analytics module 610 can switch to alternative suppliers. In any event, the data analytics module 610 upon confirming the availability of to-be-ordered ingredients, can compute at least one order quantity at step 7530 based on records of consumption. For example, the order quantity could be based on the latest order placed with respect to specific ingredient. In another example, the data analytics module 610 could compare, the previous orders with periodic surplus or deficits in the inventory and derive a more realistic order quantity that better reflects the need. In another example, the order quantity could only be a fix coefficient of the minimum inventory quantity. The order quantity can then be prompted to the user by data analytics module 610 for confirmation at step 7540. The suggested order quantity can further be edited or accepted by the user through the user device 12. Lastly, the order will be finalized, generated and communicated with the supplier at step 7550. Placing new order for ingredients will potentially change the inventory levels of ingredients and therefore, in one example, the data analytics module 610 can update inventory records based on the ordered quantity of ingredients. In another example, the user, through user device 12, can communicate with first database 18 or second database 19 to update the inventory levels. In another example, the data analytics module 610 can update the ingredients inventory database by adding the ordered amount of ingredients as a pending amount. Actual addition to the existing inventory level, will be final upon delivery of the ordered ingredient. While in the embodiments above the data analytics module 610 was generally identifying whether an action was needed at step 7030 (in terms of recommending an order for at least one ingredient to be placed, or placing the order directly) based on data stored on or otherwise accessible via the first database 18, in other embodiments the data analytics module 610 can also rely on data stored on or otherwise accessible via the second database 19, a further described below. The second database 19 can be used for storing information, including inventory information, related to a pharmacy where the mixer 10 is used.

Inventory Management

Figure 34:
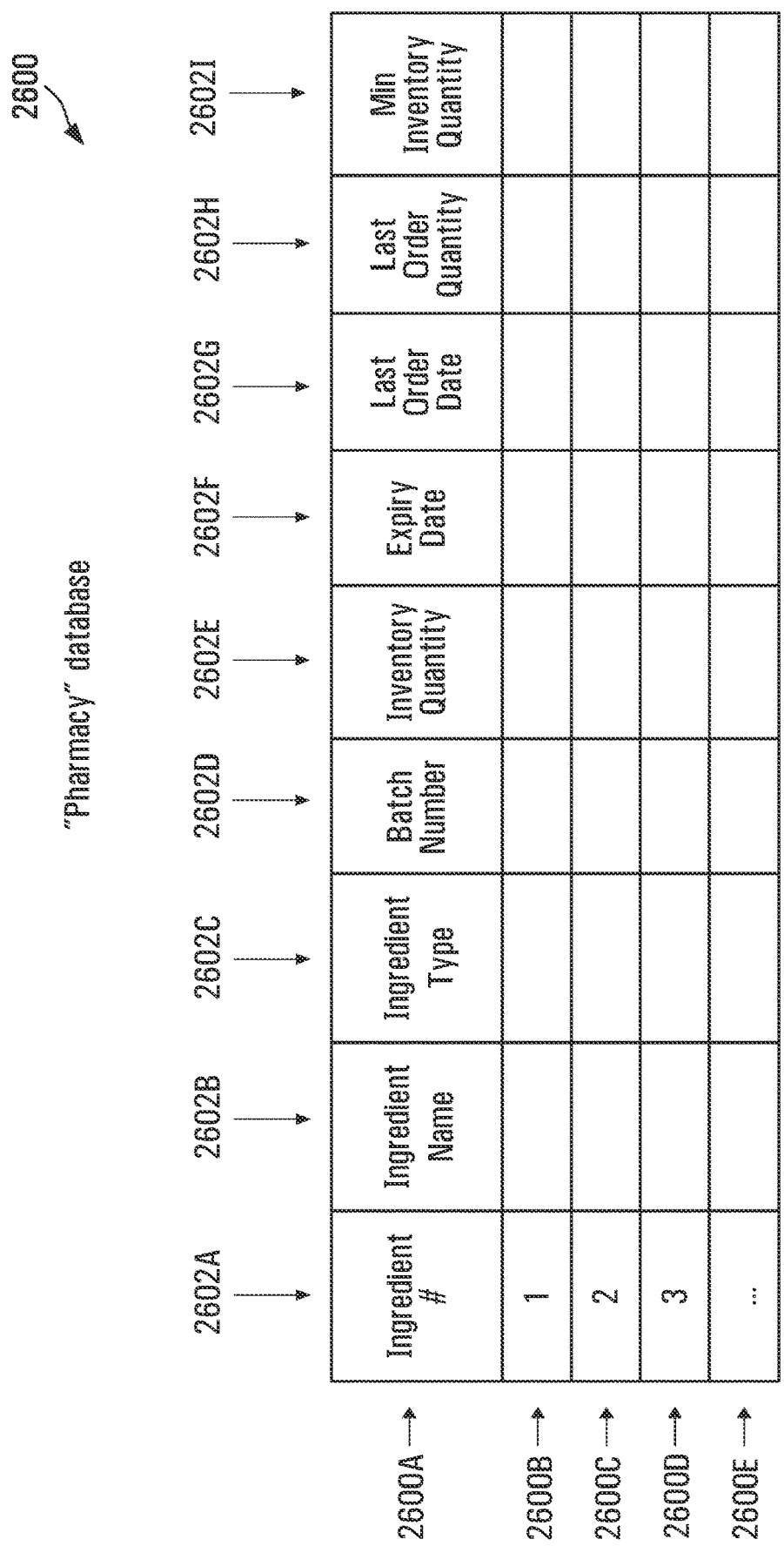
FIG. 34 is a table for storing pharmacy inventory information.

FIG. 34 shows possible contents of the second database 19, e.g., the ingredient inventory table 340 or ingredient table 2600. Each of the records 2600A . . . 2600E in the ingredient inventory table 340 is associated with a respective ingredient in the pharmacy inventory and includes a plurality of entries in a plurality of fields. The fields can include an ingredient #field 2602A, an ingredient name field 2602B, an ingredient type field 2602C, a batch number field 2602D, an inventory quantity field 2602E, a BUD field 2602F, a last order date field 2602G, a last order quantity field 2602H and a minimum inventory quantity field 2602I.

The ingredient #field 2602A is associated with an ingredient and stores a unique identifier of the given ingredient. Unique identifiers can include: CAS number, EC Number, MDL Number, Beilstein Registry Number, PubChem SID, PubChem CID or any other identifier known to a person of skill in the art.

The ingredient name field 2602B stores a name of the given ingredient, such as a chemical name (e.g., as developed by the International Union of Pure and Applied Chemistry IUPAC), an International Nomenclature of Cosmetic Ingredient (INCI) name, a tradename and/or any other proprietary name.

The ingredient type field 2602C can specify whether the given ingredient is an active pharmaceutical ingredient (API), an excipient, a surfactant, etc.

The batch number field 2602D stores a specific batch number for the given ingredient. for a given ingredient name, multiple ingredient #entries can be present in the field 2602A each corresponding to a distinct batch number in the batch number field 2602D.

The inventory quantity field 2602E stores a quantity (in mass or volume) that is available in the inventory of the pharmacy for a given batch of a given ingredient.

The expiry date field 2602F stores an expiration date for a given batch of a given ingredient. Within the context of the present disclosure, the term "expiry date" is used in association with ingredients, while the term "beyond-use date" (BUD) is used in association with a compounded composition. The BUD is determined from the date the compounded composition is compounded.

The last order date field 2602G stores a date when a given batch of a given ingredient was last ordered.

The last order quantity field 2602H stores a quantity of a last order of a given batch of a given ingredient.

The minimum inventory quantity field 2602I stores a threshold quantity for a given ingredient.

Figure 35:
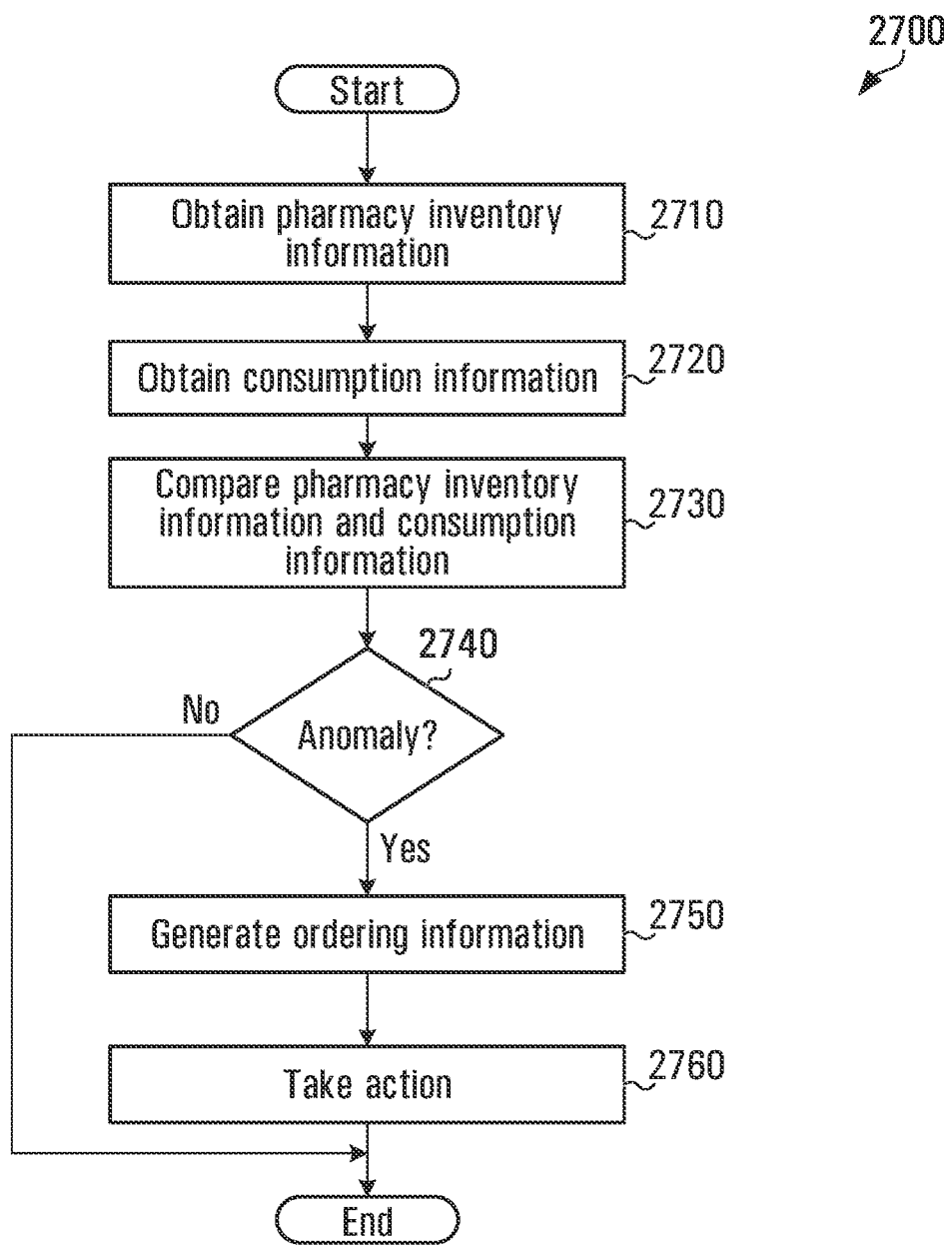
FIGS. 35, 36A and 36B are flowcharts of an inventory management processes.

In some embodiments, the data analytics module 610 is configured to monitor the data at least in the credential tables 310 and the sales table 330 of the first database 18, as well as the ingredient inventory table 340 of the second database 19, as further described below, and to carry out a process 2700 illustrated by FIG. 35, performed for account holder X.

Specifically, at step 2710 the data analytics module 610 obtains pharmacy inventory information with a supplier, for example the supplier that manages the database 19. The pharmacy inventory information can include any subset of the data that is stored in the ingredient inventory table 340, such as ingredients that are in the inventory of the supplier, an identifier for each one of the ingredients as per the ingredient name field 2602B, a batch number (or a plurality of batch numbers, where applicable) for each one of the ingredients as per the batch number field 2602B, a quantity for each one of the ingredients as per the inventory quantity field 2602E, a minimum inventory quantity as per the minimum inventory quantity filed 2602L, etc.

In a second step 2720, the data analytics module 610 obtains consumption information for at least one ingredient and for an account holder X, as further described below. The account holder X can be a pharmacy, or a specific employee of the pharmacy, having the inventory that is associated with the pharmacy inventory information above. This can be done in several ways, for example the consumption information can be obtained via data stored in the credential tables 310 and the sales table 330 of the first server 16 for an account holder X. The data analytics module 610 then compares the consumption information to the pharmacy inventory information at step 2730. This comparison can also be done in several ways and involve several steps, as further described below. For example, the comparison can first include a cross-reference between a specific ingredient associated with the data stored in the credential tables 310 and the sales table 330 and the identifiers stored in the ingredient name field 2602B—in other words the data analytics module 610 associates the consumption information for an ingredient with the pharmacy inventory information for the same ingredient. In one example, the consumption information can be an expected consumption for the specific ingredient based on past orders by the account holder X (this can be expressed as a quantity of ingredient used per unit of time, etc.). At step 2740 the data analytics module 610 whether there is an anomaly, for example based on a discrepancy between the expected consumption for the account holder X and the inventory quantity for the specific ingredient. If the data analytics module 610 concludes at step 2740 that no action is needed, the process 2700 ends. If the data analytics module 610 concludes at step 2740 that an action is needed, the data analytics module 610 then generates ordering information at step 2750. The ordering information can include an identifier for the specific ingredient, a quantity for the ingredient, the quantity being generated at step 2750 being enough to address the discrepancy between the expected consumption for the account holder X and the inventory quantity for the specific ingredient. At step 2760 the data analytics module 610 then takes an action. Such action can involve creating some sort of notification or message for the account holder X to advise him at least of some of the content of the ordering information generated at step 2750. It also can involve the generation of an offer or an order based at least in part on the ordering information generated at step 2760.

Figure 36A:
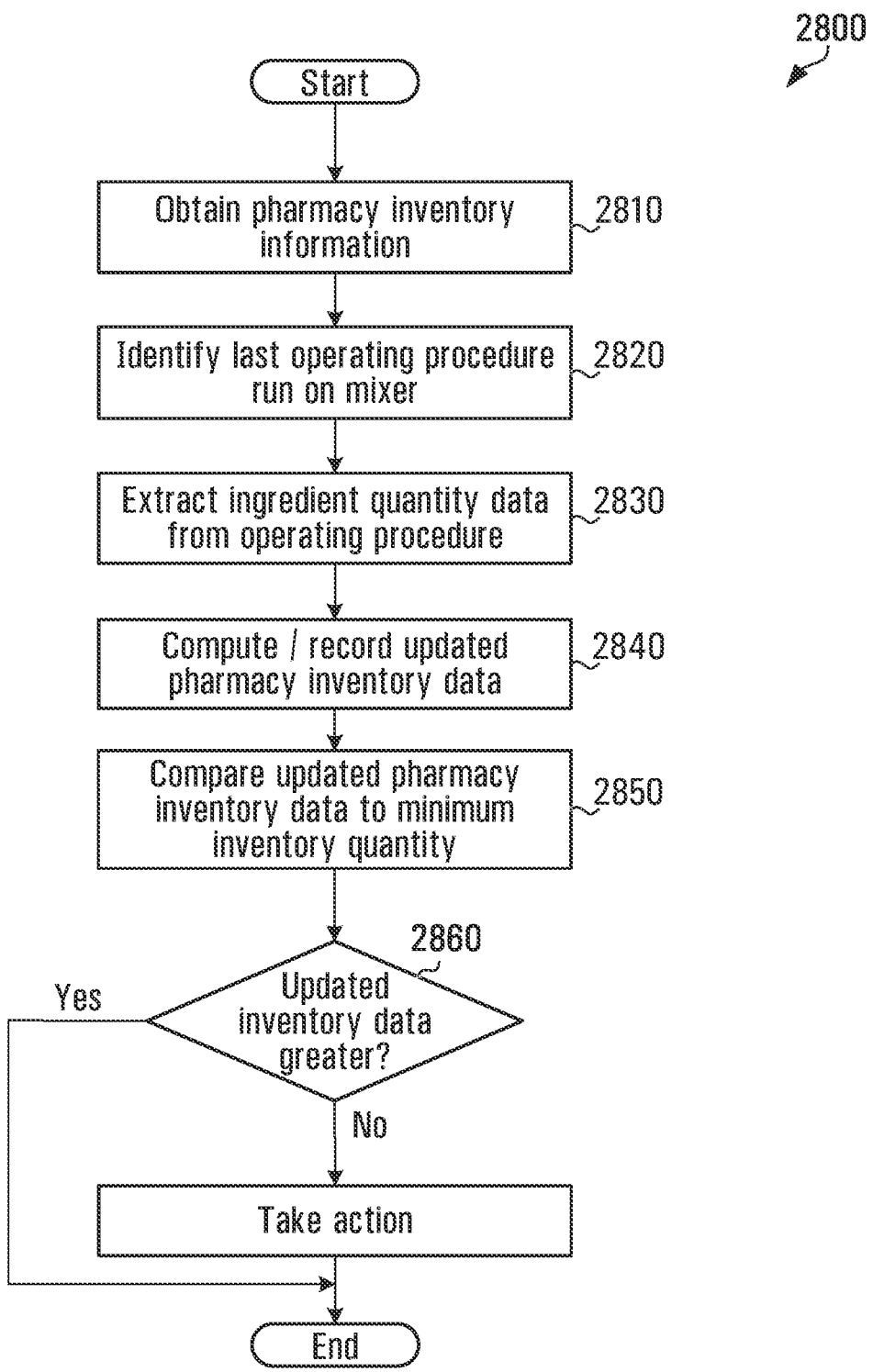

The information in the ingredient table 2600 can also have value in terms of data analytics and marketing. Specifically, the data analytics module 610 can also be configured to monitor the data in the ingredient tale 2600 and to carry out a process 2800 illustrated by FIG. 36A.

Specifically, at step 2810, the data analytics module 610 obtains ingredient inventory information specific to a pharmacy, that is the pharmacy where the mixer 10 is used, by consulting the ingredient table 2600. As part of this step, data relating at least to the ingredient #field 2602A, the ingredient name field 2602B, the batch number field 2602D and the inventory quantity field 2602 E can be obtained by the data analytics module 610.

At step 2820, the data analytics module 610 identifies the last SOP that has been run on the mixer 10. This can be achieved in several ways depending on whether the data analytics 610 gathers this information at the level of the mixer 10 or at the level of the first database 18. In one example, the data analytics module 610 accesses a log of the mixer 10 (also known as compounding record which will be described later in this disclosure) and identifies the last SOP entry in the log. Alternatively, the data analytics module 610 accesses the compounding records of the mixer 10, as further described below, identifies the last compounding record generated by the mixer 10 and identifies the SOP associated with the last compounding record. In another example, the data analytics module 610 accesses the SOP table in the first database 18 and identifies, for a mixer associated with a given account #, the last SOP that has been run on the mixer 10. The SOP can be identified in several ways, such as by the SOP #as found in the SOP #field 352A of the SOP table 350.

At step 2830, the data analytics module 610 extracts ingredient quantity data from the SOP identified at step 2820. For example, using the SOP #identified at step 2820, the data analytics module 610 reads the record associated with the SOP #in the SOP file field 352D and identifies within such record the quantities needed for each one of the ingredients being used in the SOP. In the instances where the SOP is associated with a nominal weight/volume, the data analytics module 610 further reads the compounding record to identify the actual weight/volume of the ingredient(s) that was used when the SOP was performed. Other data associated with the ingredient beyond the ingredient quantity can also be extracted by the data analytics module 610 at step 2830, such as an ingredient name/identifier, an ingredient batch number, etc.

At step 2840, the data analytics module 610 computes updated inventory data using the ingredient inventory data acquired at step 2810 and the ingredient quantity data extracted at step 2830. Because the ingredient inventory data obtained at step 2810 relates to the entire ingredient inventory of the pharmacy, and therefore to a plurality of ingredients, the data analytics module 610 first cross-references the ingredient table 2600 (specifically, the ingredient name field 2602B of the ingredient table 2600) for ingredient names/identifiers extracted at step 2830—in other words, the data analytics module 610 filters out from the ingredient inventory data all the ingredients that were not used in the last SOP performed on the mixer 10. For the ingredient remaining, or for each one of the remaining ingredients where multiple ingredients are concerned, the data analytics module 610 then subtracts from the data in the inventory quantity field 2602E the corresponding ingredient quantity data extracted at step 2830. This new quantity value constitutes the updated ingredient inventory data for the ingredient and is then recorded by the data analytics module 610 in the inventory quantity field 2602E. For example, assuming that the ingredient table 2600 indicates a quantity of 260 g of acetaminophen in the inventory quantity field 2602E and that, using the last SOP performed on the mixer 10, 58 g of acetaminophen was used, then at step 2840 the data analytics module 610 computes an updated ingredient inventory data for acetaminophen of 260−58=202 g and then records this value in the inventory quantity field 2602E for the relevant acetaminophen entry in lieu of 260 g.

Various batches of a specific ingredient can be present in the inventory in different quantities. In these cases, the data analytics module 610 also accesses batch data at steps 2810 and 2830. Specifically, the data analytics module 610 reads both the ingredient name field 2602B and the batch number field 2602D at step 2810. At step 2830, the data analytics module 610 extracts both ingredient quantity data from the SOP/compounding record identified at step 2820 as well as ingredient batch data. The ingredient quantity data extracted at step 2730 is therefore linked to a specific batch of the ingredient. At step 2840, the data analytics module 610 then cross-references the ingredient table 2600 (specifically, both the ingredient name field 2602B and the batch number field 2602D of the ingredient table 2600) for both the ingredient names/identifiers and the ingredient batches extracted at step 2830—in other words, the data analytics module 610 filters out from the ingredient inventory data all the ingredients and the ingredient batches that were not used in the last SOP performed on the mixer 10. For each batch of ingredient, the data analytics module 610 then subtracts from the data in the inventory quantity field 2602E the corresponding ingredient quantity data extracted at step 2830. This new quantity value constitutes the updated ingredient inventory data for the ingredient and batch of ingredient and is then recorded by the data analytics module 610 in the inventory quantity field 2602E for that batch.

At step 2850, the updated ingredient inventory data computed at step 2840 is compared by the data analytics module 610 to a minimum ingredient inventory quantity stored in the minimum inventory quantity field 2602I of the ingredient table 2600. The minimum ingredient inventory quantity is generally specific to an ingredient, irrespective of the number of batches that can be associated with the ingredient in the ingredient table 2600, however the minimum ingredient inventory quantity can also be batch-specific. The minimum ingredient inventory quantity is generally representative of a minimum quantity of the ingredient that is required in the pharmacy inventory to ensure continuing compounding operations (e.g., to ensure that the pharmacy will be capable of compounding its customers' formulations without interruption due to a shortage of an ingredient). The minimum ingredient inventory quantity is reliant upon a number of factors, such as the pharmacy and its location, the number of customers, the needs of the customers, the supply chain and the general availability of the ingredient, the number of batches for an ingredient that are in the inventory, the expiry date of an ingredient batch, etc. and therefore the minimum ingredient inventory quantity can be set in the minimum inventory quantity field 2602L by the user or other personnel according to their knowledge of operations. In another example, the minimum ingredient inventory quantity field 2602L could be set using a predictive AI-based algorithm that learns from previous consumption patterns.

Figure 36B:
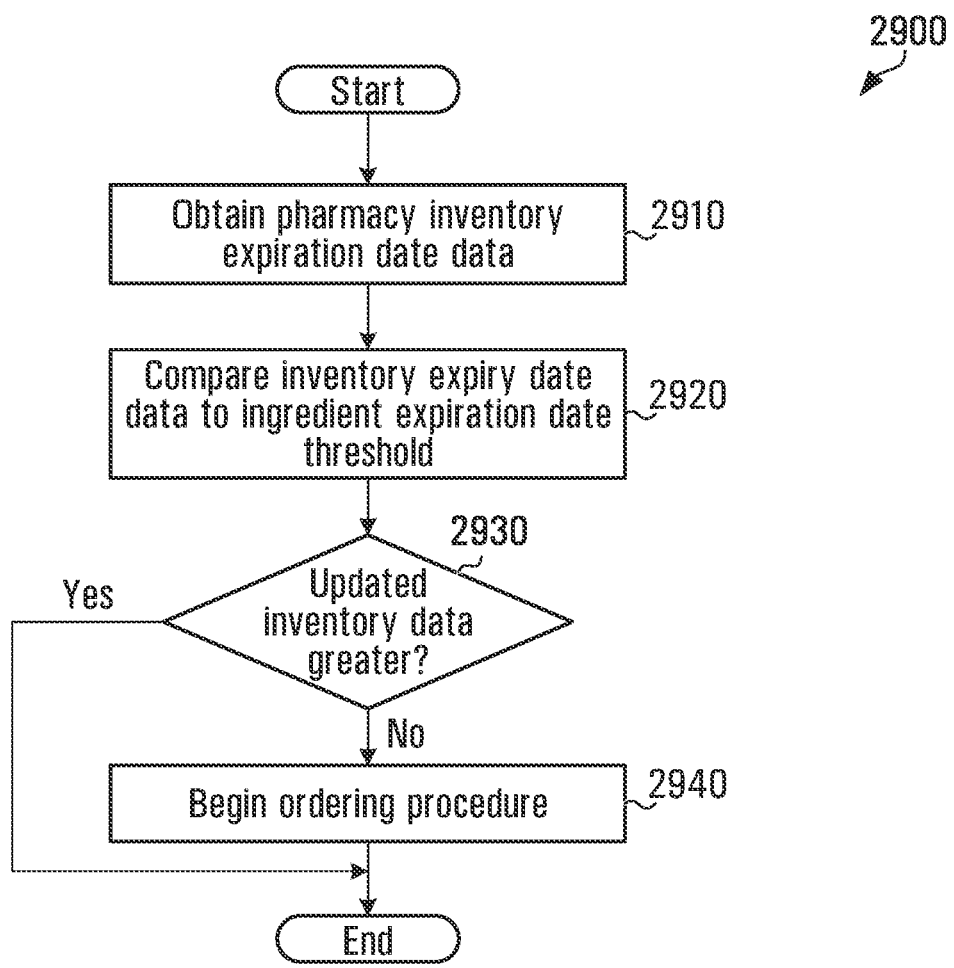

When the data analytics module 610 concludes that the updated ingredient inventory data computed at step 2840 is greater than the minimum ingredient inventory quantity, the process 2800 comes to an end. If, however, the data analytics module 610 concludes at step 2850 that the updated ingredient inventory data computed at step 2740 is equal to or is less than the minimum ingredient inventory quantity, then the data analytics module 610 begins the ordering process further described in connection with FIGS. 36A and 36B.

In some cases, even though the updated ingredient inventory data is greater than the minimum ingredient inventory quantity, it can still be needed to order a new batch of ingredient when the relevant date nears the expiry of the ingredient in the inventory. Such process for expiry verification is shown in the flowchart of process 2900. At step 2910 the data analytics module 610 can obtain inventory expiry data by consulting the expiry field 2602F in the ingredient table 2600.

At step 2920, the inventory expiry data obtained at step 2910 is compared to an ingredient expiry threshold, the ingredient quantity threshold being specific to a batch of an ingredient. In other words, various batches of an ingredient can have distinct ingredient expiry thresholds even though they all relate to the same ingredient. The ingredient expiry threshold is generally representative of the consumption life of the compounded product and therefore, at step 2930, the user can decide through a logic function to begin a new ordering process at step 2940.

Mixer Control—Sensor Information

Figure 37:
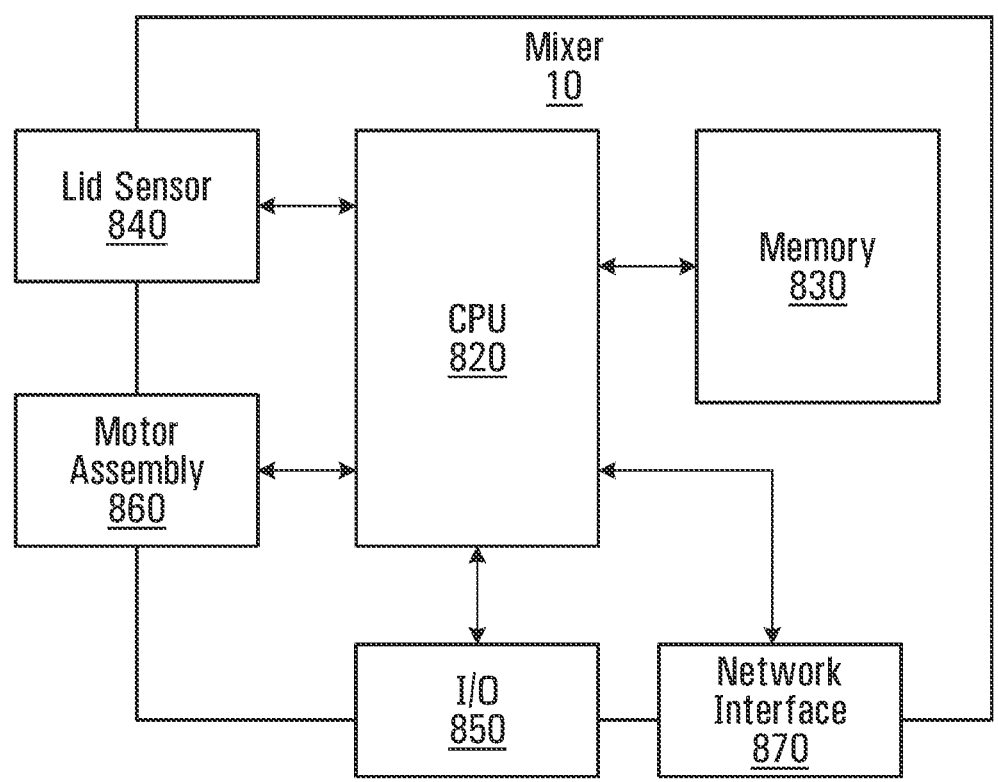
FIG. 37 is a block diagram showing components internal to a mixer.

FIG. 37 shows various components of the mixer 10 wherein the mixer 10 is network-enabled. Shown is a control and processing unit (CPU) 820, a memory 830, a lid sensor 840 (to detect whether the mixer 10 is closed or open) and a motor assembly 860. Also shown are an input/output interface (I/O) 850 (such as a screen display with key/button input) and a network interface 870. The CPU 820 executes computer-readable instructions stored in the memory 830 of the mixer 10 to process received signals from the lid sensor and to produce signals to control the motor assembly 860, for example. As an example, if the lid sensor 840 determines that the mixer 10 is open, the CPU 820 can prevent the motor assembly 840 from applying rotation and revolution. As another example, if the lid sensor 840 determines that the mixer 10 is closed, the CPU 820 can enable the motor assembly 840 to apply rotation and revolution.

The network interface 870 enables the CPU 820 to communicate with an external device or system, with the user device 12 (see FIG. 40), the first server 16, and/or the second server 17. The mixer 10 is connectable to such external device/system over a wired (e.g., a cable) or wireless link. The communication link between the network interface 870 and the user device 12 and/or the first server 16 and/or the second server 17 can be direct (e.g., Bluetooth pairing, USB, . . . ) or it can be indirect (e.g., over the data network 14 or a LAN, by way of an Ethernet cable or wireless access point, for example).

Figure 38:
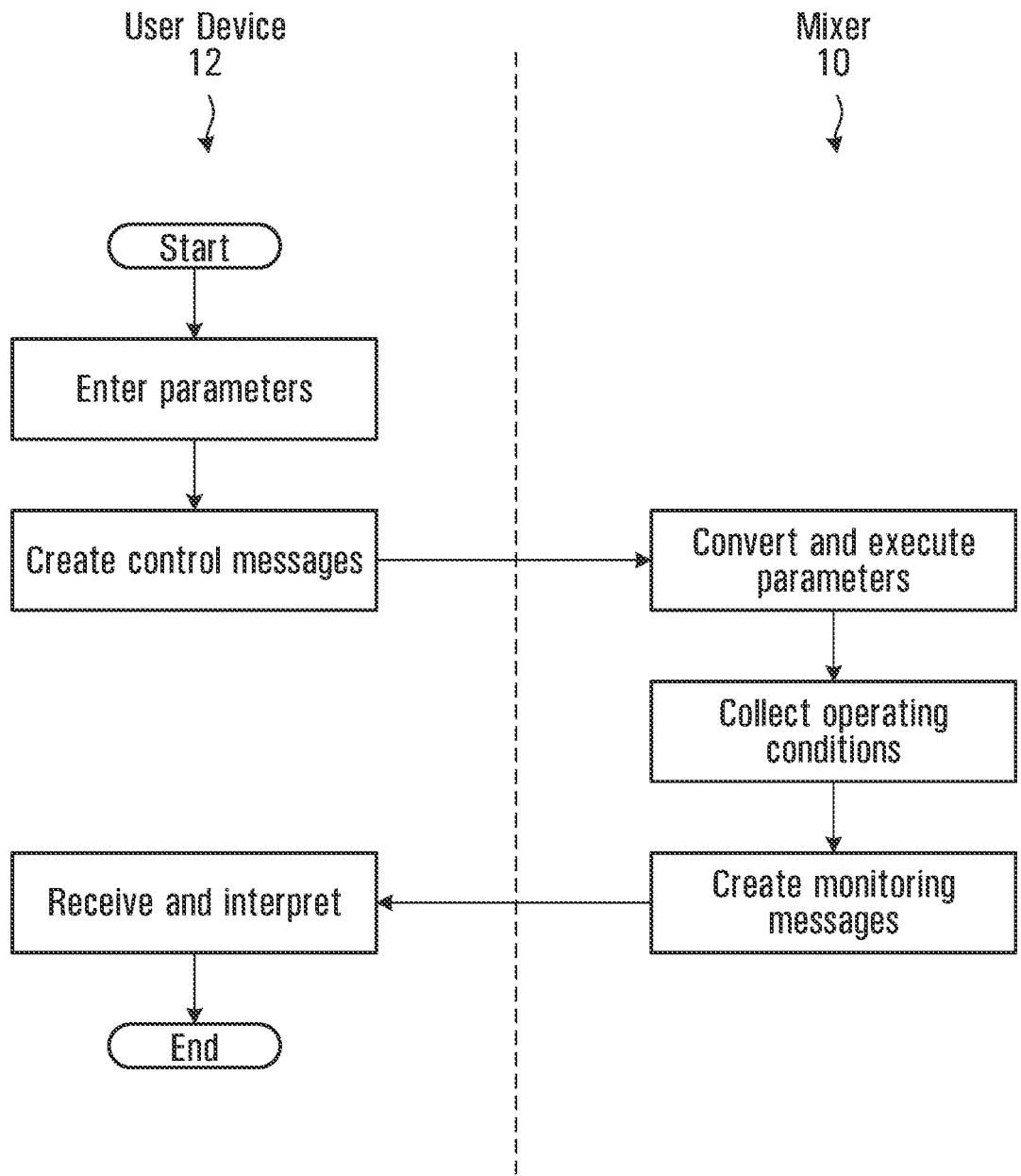
FIG. 38 is a flow diagram showing interaction between a user device and a mixer.

Referring as well to FIG. 38, control messages travel from the user device 12 over the direct or indirect communication link and are received at the network interface 870 and processed by the CPU 820. These control messages can contain operating parameters as described above. Specifically, the mixer CPU 820 receives the control messages via the network interface 870, extracts the operating parameters contained therein, and acts on them, resulting in control of the motor assembly 860 to operate the mixer 10 in accordance with the operating parameters contained in the control messages.

In the opposite direction of communication, the CPU 820 is configured to collect information about usage of the mixer 10 (e.g., from the lid sensor 840 and also from internal sensors such as a clock, RPM sensor, . . . ), encapsulate this information into monitoring messages, and send the monitoring messages to the user device 12 via the network interface 870.

Figure 39:
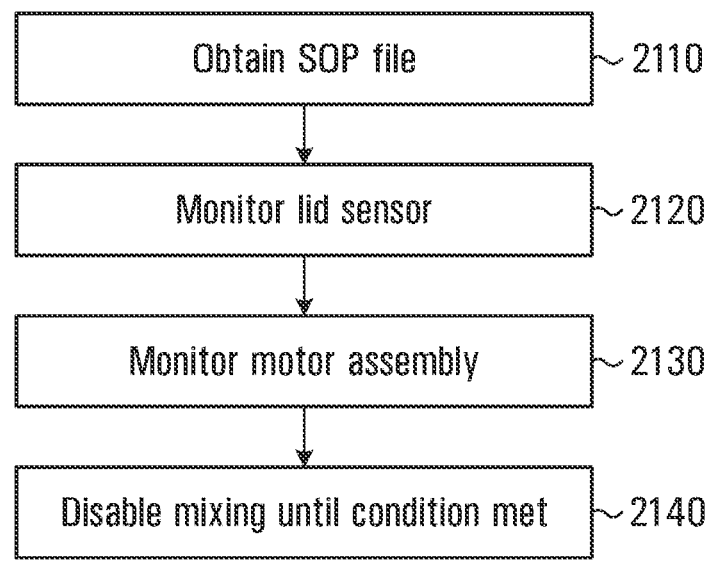
FIG. 39 is a flowchart showing steps in a process that can be carried out by a planetary mixer.

The CPU 820 can execute the method of FIG. 39, whereby at step 2110, the CPU obtains a computer-readable SOP file associated specifying a procedure for compounding a pharmaceutical formulation using the mixer 10. The CPU 810 can obtain the SOP file by consulting a memory of the mixer 10, and/or can obtain the SOP file from the user device 12 or the first server 16. In this example, the SOP file specifies at least: a suggested first mixing step, a suggested second mixing step, and a step intermediate the suggested first and second mixing steps requiring the container to be removed from the planetary mixer. Then, at step 2120, the CPU 820 monitors the lid sensor 840 of the mixer 10 to determine whether the mixer 10 is open or closed. At step 2130, the CPU 820 monitors the motor assembly 860 of the mixer 10 to determine that an actual first mixing step corresponding to the suggested first mixing step has been completed. Finally, at step 2140, the CPU 820 disables further mixing by the motor assembly until the monitoring (at step 2130) determines that the mixer has been opened after completion of the actual first mixing step.

Figure 40:
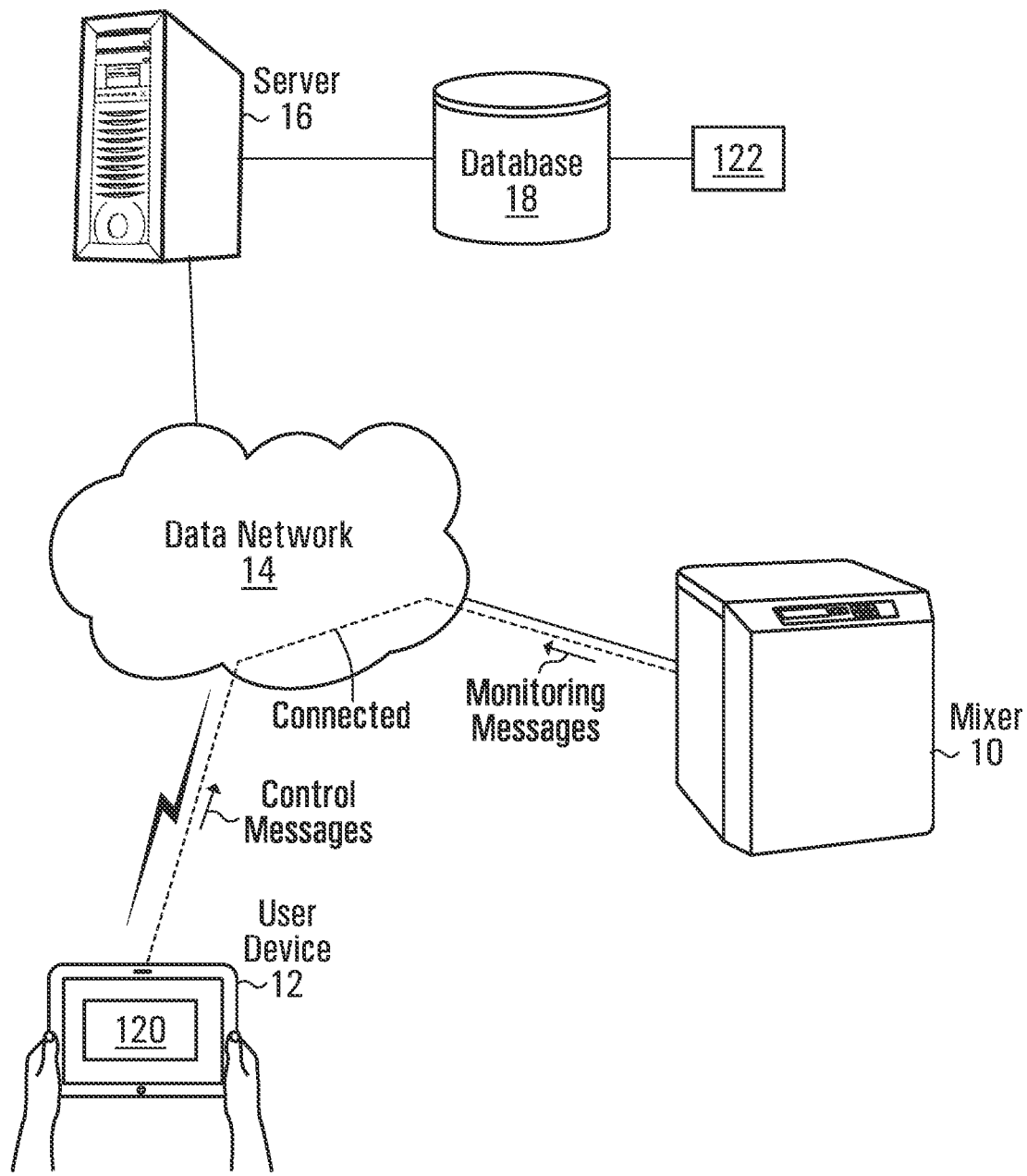
FIG. 40 illustrates the mixer system of FIG. 1 in which the mixer is connected to the data network.

Continuing to refer to FIG. 40, the user device 12 executes a mixer control application 120 to formulate and send control messages (containing operating parameters) to the mixer 10. In other words, the mixer control application 120 can encode the operating parameters into the control messages. The mixer control application 120 can be one of the processes that is executed by the user device 12 as a result of the execution of computer-readable instructions stored in the memory of the user device 12. The mixer control application 120 can allow a user to enter operating parameters which are then converted into control messages and transmitted to the mixer 10. For example, the user enters operating parameters such as "30 seconds at 2000 rpm" via the GUI implemented by the user device 12. The mixer control application 120 obtains operating parameters from a memory of the user device 12 or from an external device or system, such as the first server 16, over the data network 14. The mixer control application 120 converts these operating parameters into control messages in accordance with a protocol understandable by the mixer 10.

Also, the mixer control application 120 receives and processes monitoring messages from the mixer 10. The collected monitoring messages can be used by the mixer control application 120 for various purposes, such as to signal the need for preventative maintenance. Specifically, the mixer control application 120 can be configured to upload collected usage information to the first server 16. The first server 16 can then provide "preventative maintenance" detection functionality, as well as data analytics. In an example, the data analytics module 610 at the first server 16 can be used to track precise usage and performance issues for an individual machine or over an entire fleet of mixers. This allows precise detection of anomalous ingredient supply conditions. In another example, the data analytics module 610 at the server monitors how many hours the mixer has been used and comparing against a table 122 supplied by the manufacturer. This table 122 can be stored in the first database 18 or in the memory 220 of the first server 16 and can indicate a suggested or number of hours of use after which maintenance should be performed on the mixer 10. In this case, the output of the data analytics module 610 can be an indication as to whether mixer maintenance is recommended.

Mixing Container with Adapter

Figure 41:
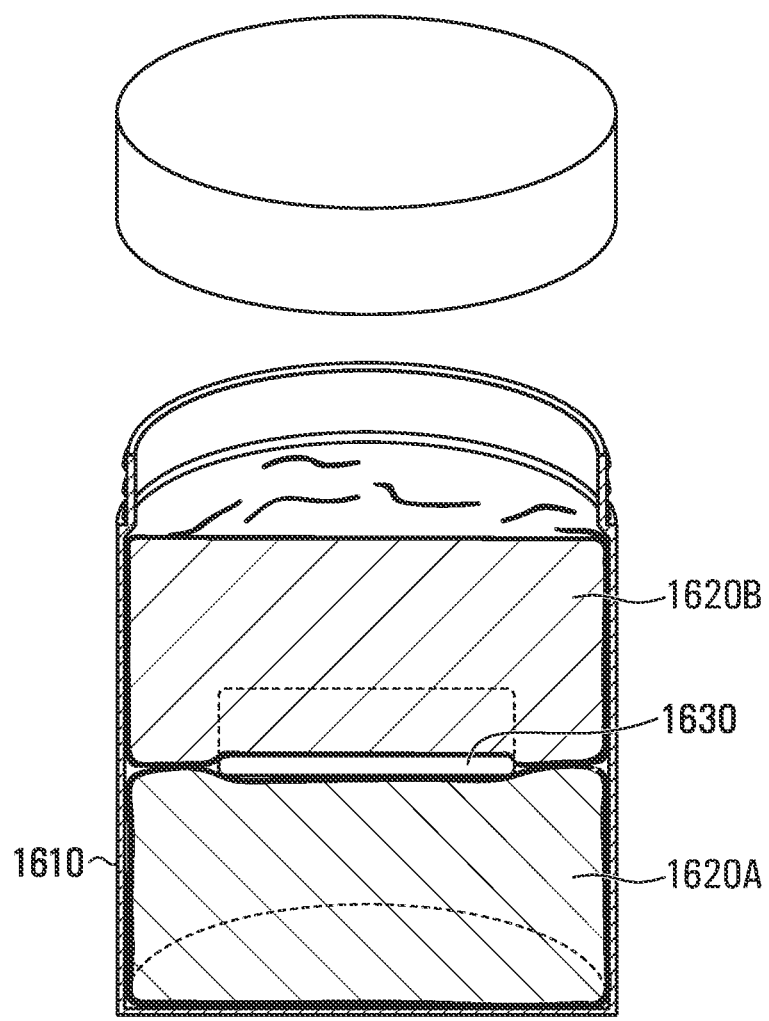
FIG. 41 shows a container to be mixed fitted with an adapter.

Referring to FIG. 41, the mixing container 1610 (e.g., the container placed into the mixer 10) can be used with a universal adapter 1620, which allows the contents of a subject container 1630 placed directly inside the mixing container. Typically, the mixing container 1610 can be a jar. The subject container 1630 can be a dispensing container such as a Topi-click™ (Doselogix, LLC). In some cases, the subject container 1630 can have a length dimension that exceeds the diameter or the height of the mixing container 1610 when the latter is a cylinder, such that it only fits when placed in diagonally.

Another example of the "mixer functionality" is an adapter in the mixing process that is configured to hold the final dispensing container from which the prepared formulation is to be dispensed. Alternatively, once mixed in a mixing container, the mixed formulation can be transferred from the mixing container to a dispensing container. If the mixer functionality is selected to be "adapter mixing", an implicit assumption is that the intended use is mixing a cream/gel/topical compound in a dispensing container. This can lead to additional granularity (which can be referred to as a sub-functionality) when selecting the "adapter mixing" functionality. For example, as shown in table 3:

TABLE 3

| Mixer functionality: | Mixer sub-functionality |
| --- | --- |
| Adapter mixing | Pump adapter |
| Adapter mixing | 15 ml-50 ml Unguator jar adapter |
| Adapter mixing | 100 ml Unguator jar adapter; |
| Adapter mixing | 100 ml Samix jar adapter |
| Adapter mixing | Universal adapter |

The universal adapter 1620 fits inside the mixing container 1610 (e.g., a jar) and can be configured at least partly to espouse the shape of the outside of the subject container 1630, such as of the exterior side and/or bottom walls of the subject container 1630. As shown in FIG. 41, the universal adapter 1620 can have two (or more) parts, a first part 1620A that lies at the bottom of the mixing container 1610 and a second part 1620B that is added once the subject container 1630 has been placed onto the first part 1620A.

The first part 1620A and the second part 1620B can be made of the same material or of different materials. An example of a material that can be used for the first part 1620A and/or the second part 1620B can be a compressible foam. Certain desirable characteristics of the compressible foam include being able to espouse a contour of the subject container 1630 at rest while being sufficiently resistant to surface deformation at high rotation and revolution speeds. For example, the material can be designed or selected to be compressible at rest and to undergo no more than 1%, 3%, 5% or 10% surface deformation at 800 RPM rotation and 2000 RPM revolution. An example of a commercially available compressible foam that can be suitable can include a polyurethane foam, a viscoelastic polymer foam, LDPE or EVA foam with a shore 00 hardness that ranges from about 20 to about 60. The compressible material can be a single use throw away item that is not re-usable. Alternatively, it can be sculptured to the external shape of the container in which the loaded ingredients are mixed in a way to still induce compression of the material as the adapter is placed in the mixing container 1610 with the container 1630 therein, such as to keep the container 1630 in place during the mixing operation.

A further example of a material that can be used for the first part 1620A and/or the second part 1620B can be a controllable-hardness material. One desirable characteristics of the controllable-hardness material includes the ability to be hardened prior to being subjected to high acceleration. In other cases, the material is chosen or designed to as to have an increased hardness by virtue of being subjected to acceleration; an example of such a material is Polyborodimethylsiloxane, a non-Newtonian fluid known commercially as D30 and described in U.S. Pat. No. 7,794,827. In some cases, application of an electrical current (e.g., charging) causes the material to acquire an increased hardness while charged. This allows the material to be molded while discharged and then to harden while charged, subsequent to which it is then subjected to planetary motion by the mixer 10. An example of a controllable-hardness material that can be suitable can be based on the findings of Orolva et al., as described in the paper "Variation in Mechanical Properties Due to The Effect of Electric Potential", published as Dina Orlova et al 2017 *IOP Conf. Ser.: Mater. Sci. Eng.* 225 012218, hereby incorporated by reference herein.

In some embodiments, rather than being made of two parts, the universal adapter 1620 is made of a single part that has an opening for the subject container 1630.

The universal adapter 1620 is made of a malleable material (e.g., putty), some of which can be compressed and moved out of the way to make room for the subject container and this removed material can be placed on top of the subject container 1630 to cocoon the subject container within the larger, mixing container 1610. In this case too, the universal adapter 1620 need not be made of two parts.

Due to its flexible, compressible and/or configurable nature, the universal adapter 1620 can be shaped to occupy a desired space within the mixing container 1610. The sum of the volume of the universal adapter 1620 and the subject container 1630 can occupy at least a certain threshold percentage of the total internal volume of the mixing container 1610 when empty. This threshold percentage can be 75% (e.g., more than 85%, more than 90%, more than 95%, more than 99%) of the total internal volume of the mixing container 1610.

The use of a universal adapter 1620 allows the efficient mixing of different subject containers 1630 that have varying dimensions, without having to purchase an array of specialized adapters. This allows a compounding user to be efficiently handle different dosages and/or different manufacturers of subject containers, for example.

Figure 42:
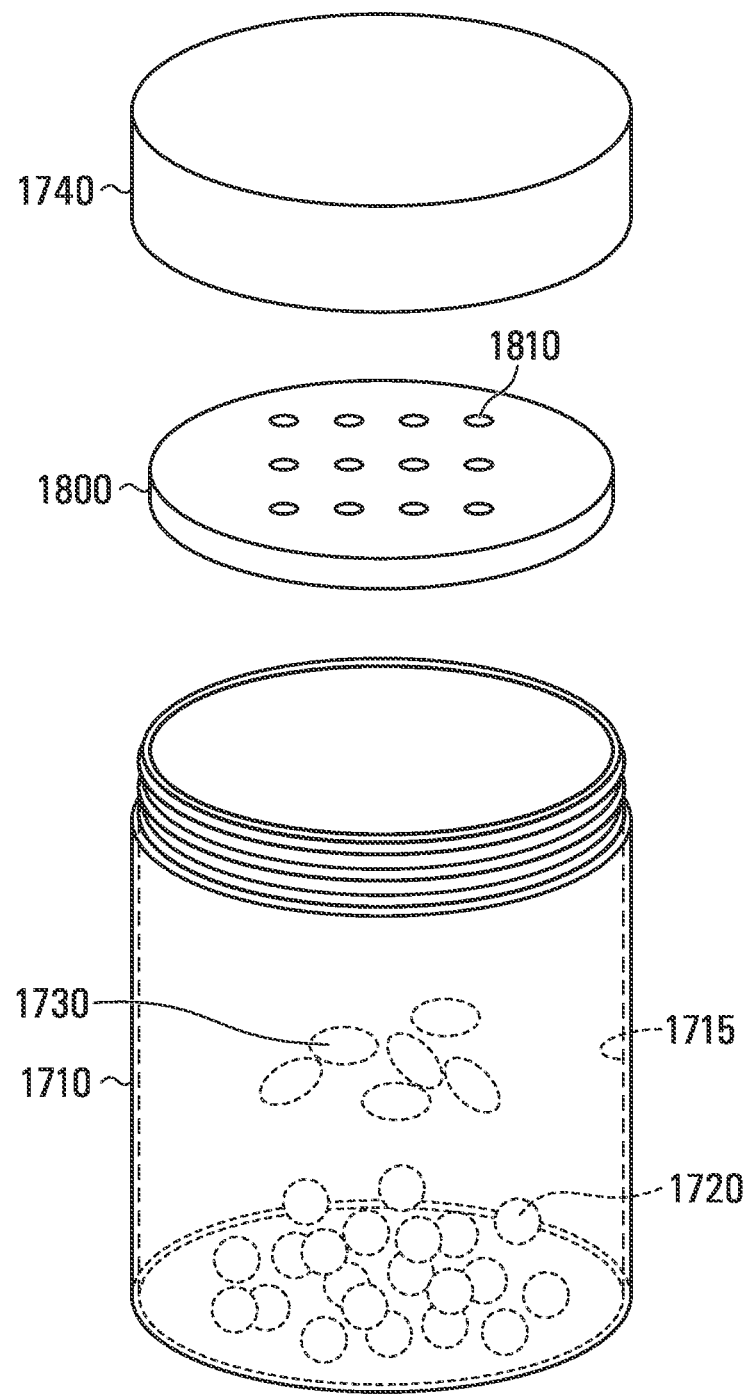
FIGS. 42, 43A and 43B show a container to which is fitted with a filter head having a plurality of apertures.

As previously described, planetary mixing can be used for particle size reduction, also referred to as milling or micronizing. FIG. 42 shows a mixing container 1710, a liner 1715 (made with a material having suitable impact resistance, for example made with stainless steel) and milling beads 1720 (e.g., made of zirconium) can be placed into the mixing container 1710 together with the substance 1730 to be micronized. A cover 1740 can be placed onto the mixing container 1710, and the mixing container 1710 undergoes mixing by a planetary mixer, such as the mixer 10. Thereafter, the mixing container 1710 is removed from the planetary mixer, and the cover 1740 of the mixing container 1710 can be removed and replaced with a specialized filter cap 1800.

As shown in FIG. 42, the filter cap 1800 is perforated, with holes 1810 that are smaller in dimension than the milling beads 1720. For example, if the beads 1720 are circular with a given diameter, the largest dimension of any of the holes 1810 is smaller than the diameter. The filter cap 1800 serves to separate residual micronized powder (substance 1730 after particle size reduction) from the milling beads 1720, allowing the powder to escape the mixing container 1710 and the beads 1720 to remain. This reduces the loss of the substance (e.g., pharmaceutical ingredient) that was milled, resulting in less waste and, ultimately, greater savings for the compounding user.

Figure 43A:
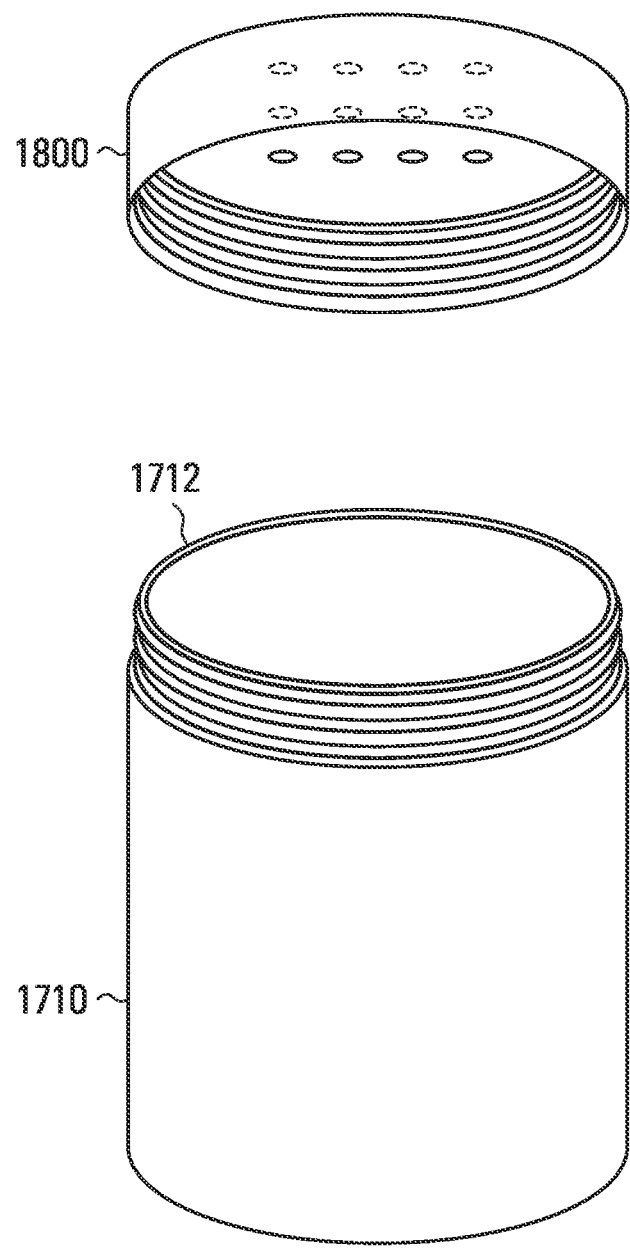
Figure 43B:
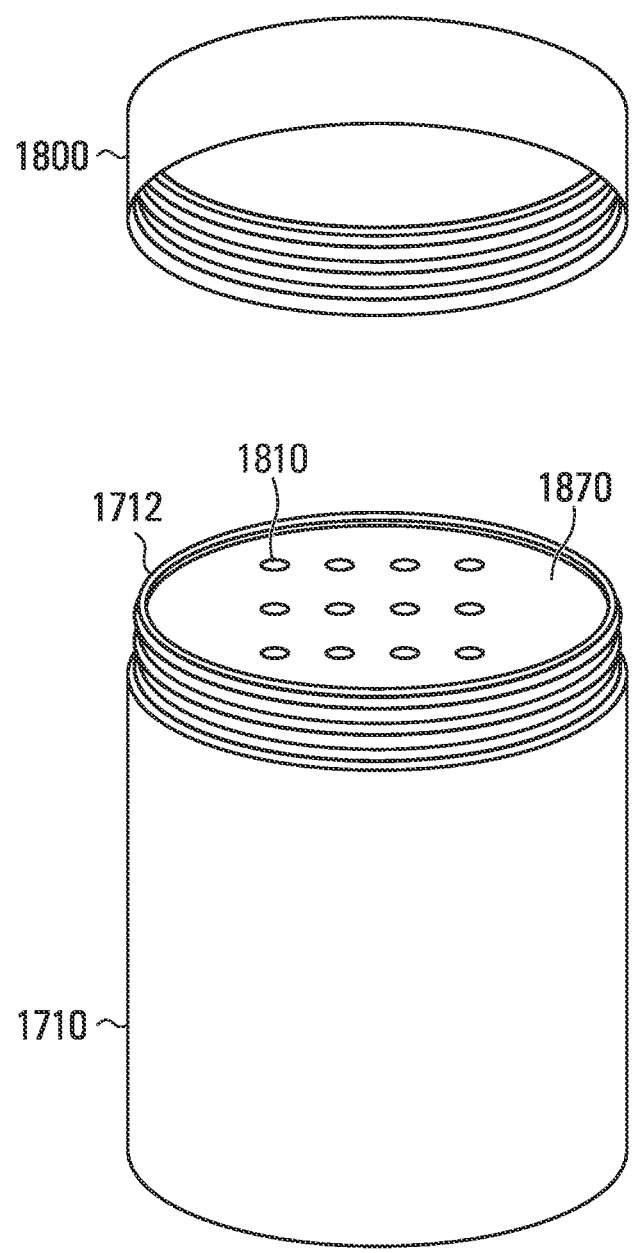

FIG. 43A shows that the filter cap 1800 is a replacement of the cover 1740 and can be screwed onto the mouth 1712 of the mixing container 1710 in lieu of the usual, exterior cover 1740. The mouth 1712 and the cover 1740 have complementary threads, as do the mouth 1712 and the filter cap 1800. FIG. 43B shows the filter cap as part of a two-piece cap with an exterior cap 1860 such that when the exterior cap 1860 is removed, the filter cap 1870 remains held in place underneath and secured to the mouth 1712 of the container 1710. For example, the filter cap 1870 can be press-fitted onto the mouth 1712 of the mixing container 1710. To remove the filter cap 1870, a tool can be used to reach behind the perforations 1810 and detach the filter cap 1870 from the mouth 1712 of the mixing container 1710.

Other Embodiments

A number of embodiments of the invention have been described. Nevertheless, it will be understood that various modifications may be made without departing from the spirit and scope of the invention. For example, the database 1210 is illustrated as having rows corresponding to formulas, where the row corresponding to a formula has an entry for the associated operating parameters. Although it is feasible to have a single set of operating parameters for a given formula, it is possible for the operating parameters to vary as a function of the total weight of the eventual formulation. The formula database 1210 is illustrated as having rows corresponding to different formula and weight combinations, where the row corresponding to a formula and weight combination has an entry for the associated operating parameters. Further options for a given formula (or formula and weight combination) could be obtained, for example, based on other factors such as the absolute weight of an ingredient in the formula, altitude above sea level, temperature, mixer make/model, and so on. In fact, there could be a curve that captures the variance in operating parameters (e.g., rotation RPM, revolution RPM and mixing time over one or more intervals) as a function of each factor, so that depending on the value of the factor, the optimal operating parameters are obtained. The formula database 1210 can be updated as new formulas are developed and tested with the mixer 10. The formula database 1210 can be stored in the memory of the first server 16, in the memory of the user device 12 or in the memory of the mixer 10

Figure 44A:
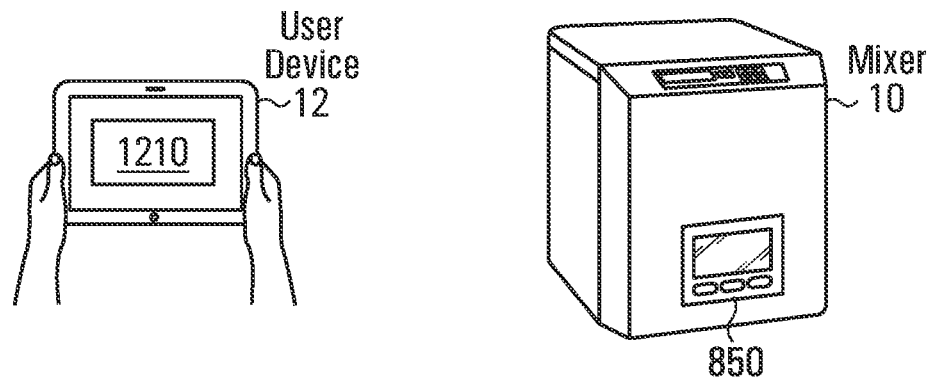
FIGS. 44A to 44C illustrate a user device and a mixer in various degrees of interconnectedness.

FIG. 44A shows the mixer 10 as a stand-alone device (e.g., it does not require networking functionality) and the formula database 1210 resides in the memory of the user device 12. The user enters a desired formula on the user device 12. One way is for the user device 12 to list the actual ingredients corresponding to the desired formula and their relative proportions. Another way is for the user device 12 to provide a menu of formulas from which the user can select the desired formula. Another way is for the user to submit a pre-determined code (or "preset") that is recognized by the user device 12; this preset can be a code selectable by the user from a menu or scannable by a scanner connected to or integrated with the user device 12. The user device 12 can include a table in memory that maps presets to formulas. In some embodiments, the user can also enter other parameters, such as the make/model of the mixer and, e.g., the elevation above sea level where mixing is taking place. The user device 12 accesses the formula database 1210 and obtains the associated operating parameters, displaying them on the screen of the user device 12. Thereafter the user manually enters the obtained operating parameters via the user interface 850 of the mixer 10.

Figure 44B:
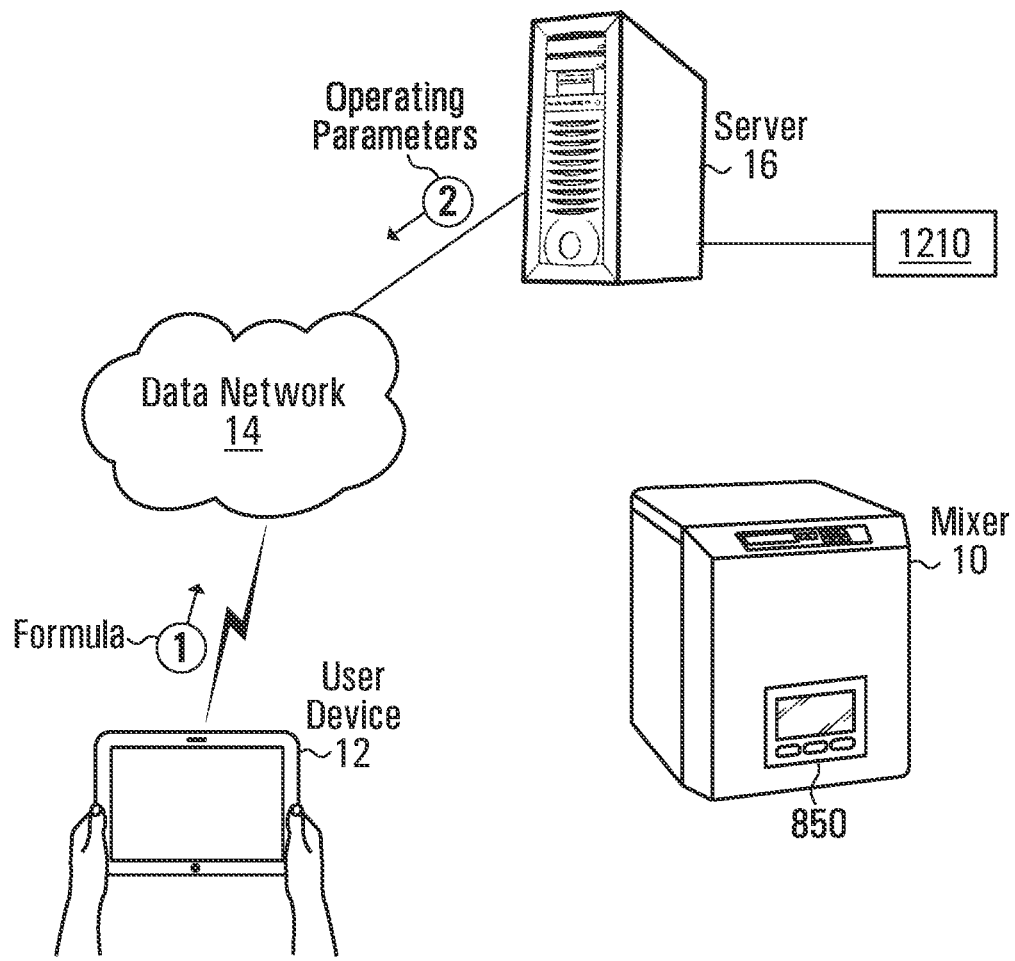

FIG. 44B shows the mixer 10 as a stand-alone device; however; the formula database 1210 resides on the first server 16. The user enters a desired formula on the user device 12 in one of the above ways, and the user device 12 contacts the first server 16 over the data network 14 and accesses the formula database 1210. The first server 16 returns the associated operating parameters. The user device 12 displays the operating parameters on the screen of the user device 12, and the user can then manually enter the obtained operating parameters via the user interface 850 of the mixer 10.

Figure 44C:
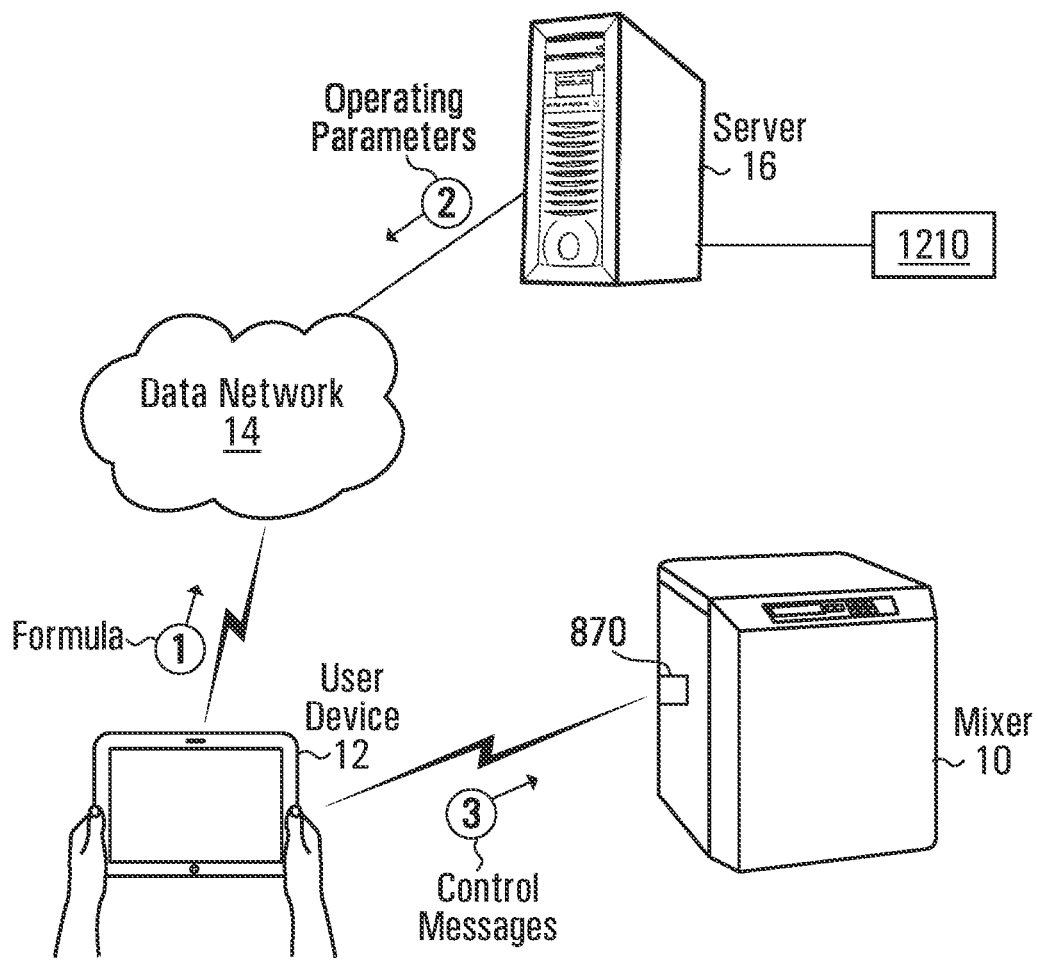

FIG. 44C shows the network functionality of the mixer 10 enabled, and the formula database 1210 resides on the first server 16. The user enters the formula on the user device 12 in one of the above ways (including, for example, by selecting a preset), and the user device 12 contacts the first server 16 over the data network 14 and accesses the formula database 1210. The first server 16 returns the associated operating parameters. (Alternatively, the formula database 1210 could reside in the memory of the user device 12, in which case the first server 16 need not be contacted.) The user device 12 then encapsulates the operating parameters into one or more control messages that is/are sent to the mixer 10 and received at the network interface 870. Optionally, the operating parameters are also displayed on screen of the user device 12.

In some instances, the user provides a code (e.g., a scannable code) to the user device 12. The code encodes the operating parameters. The code can be part of a "formula sheet" for the desired formula. If the user desires to make the desired formula, a formula sheet can be obtained, and this formula sheet can include a code that is scanned by a scanner. The formula sheet can be printed or digital. The code can include a plurality of fields, and collectively defines the operating parameters that can have been optimized for the mixer 10. For example, a scannable code can read:

004520001000, or equivalently 0045-2000-1000, which could be interpreted to mean 45 seconds at 2000 rpm rotation and 1000 rpm revolution, for example. Other constructions of the code, including more complex ones, are possible. For example, 00302000005000050040100000150, or equivalently
0030-2000-0050-0005-0040-1000-0150, could be interpreted to mean (0030=30) seconds at (2000=2000) rpm rotation and (0050=0.5)×2000 rpm revolution, followed by a pause of (0005=5) seconds, and then mixing resumes for (0045=45) seconds at (1000=1000) rpm rotation and (0150=1.5)×1000 rpm revolution. In this case, the $3^{rd}$ and $6^{th}$ fields represent a ratio of rotation rpm to revolution rpm.

Using this approach, the user device 12 reads the scannable code from the (printed or digital) formula sheet to directly obtain the operating parameters, which are then sent as control messages to the mixer 10. The mixer 10 acts as the user device and is equipped with a scanner and is configured to directly decode the operating parameters from a scannable code.

The code can be encrypted when produced and provided on a formula sheet (either printed or digital) so that it can only be decrypted by a suitable user device or mixer. For example, if the code specifies operating parameters that have been optimized for a make/model of mixer, a public/private key system infrastructure can be used to encrypt the operating parameters with a public key associated with the appropriate make/model of mixer. Meanwhile, the private key is secretly held by the mixer of the appropriate make and model. Only the appropriate make and model of mixer will be able to correctly decrypt the code and obtain the operating parameters that were initially associated by the creator of the formula sheet. Other makes or models of mixers, even if they are configured to directly read operating parameters from a code on a formula sheet, will be unable to decrypt the correct operating parameters without the correct private key, which is held secret by the mixer (or mixers) of the appropriate make and model. The code can furthermore be affixed to a mixing container, such that simply scanning the code will immediately provide the user device 12 and/or the mixer 10 with the correct operating parameters. Thus, the user device 12 and/or the mixer 10 simply needs to be fitted with the capability to interpret a limited number of fields of the code (and possibly a decryption capability); in this case there can be no need to store or access a formula database such as the formula database 1210. Since the number of fields of the code is much less than the number of possible formulas, this can be an effective way to directly convey to the user device 12 and/or the mixer 10, in an error-free way, instructions on how to operate, and without the user device 12 having to store or access a large table that maps formulas to operating parameters.

Those skilled in the art will appreciate that the reference to tables throughout the disclosure is merely a conceptualization, as other organizational formats or data structures can be suitable and can thus be employed instead of tables.

Also, those skilled in the art will appreciate that further modifications can be made without departing from the scope of the invention, which is defined by the claims appended hereto. Accordingly, other embodiments are within the scope of the following claims.

What is claimed is:

1. A non-transitory medium storing computer-readable instructions which when read and executed by at least one processor of a computing device, implement:
 a. a Graphical User Interface (GUI) functional block configured for implementing a computerized GUI that provides a user of the computing device with an opportunity to specify a compounding formula for a composition,
 b. an ingredient validation functional block configured for:
  i. receiving a code generated by a code-reader when reading machine-readable data applied on a container holding a first ingredient, wherein the code conveys one or more characteristics of the first ingredient,
  ii. consulting a database arrangement at least in part on the basis of the compounding formula to derive a formulation ingredient to be used in preparing the composition,
  iii. determining at least in part on the basis of the code if the first ingredient matches the formulation ingredient, and
 c. a planetary mixer control functional block configured for:
  i. consulting the database arrangement at least partly on a basis of the specified compounding formula to determine mixing parameters for a planetary mixer, the mixing parameters being associated with the specified compounding formula,
  ii. causing a motor assembly of the planetary mixer to apply superimposed rotation and revolution movements to a container in accordance with the mixing parameters determined from the consulting, and
  iii. one of preventing operation of the motor assembly or displaying an error message on the GUI if the determining step fails to match the first ingredient to the formulation ingredient.

2. A non-transitory medium as defined in claim 1, wherein the ingredient validation functional block is configured for:
 a. receiving a plurality of codes sequentially input by the code reader as the code reader sequentially reads machine-readable data on a plurality of containers holding respective ingredients, wherein each code conveys one or more characteristics of the respective ingredient,
 b. consulting the database arrangement at least in part on the basis of the compounding formula to derive a plurality of formulation ingredients to be used in preparing the composition, and
 c. determining at least in part on the basis of the codes if the ingredients held in the plurality of containers match the formulation ingredients.

3. A non-transitory medium as defined in claim 2, wherein the planetary mixer control functional block is configured to prevent operation of the motor assembly when the determining step fails to match all the codes to the formulation ingredients.

4. A non-transitory medium as defined in claim 1, wherein the error message indicates that the ingredient held in the container is incorrect for the specified compounding formula.

5. A non-transitory medium as defined in claim 1, wherein the code is a first code and the container is a first container holding the first ingredient, the ingredient validation functional block is configured to:
 receive a second code input by the code reader reading machine-readable data from a second container holding a second ingredient,
 determine at least in part on the basis of the second code if the second ingredient matches the formulation ingredient, and the planetary mixer control functional block being further configured to enable operation of the motor assembly when the determining determines that the second ingredient matches the formulation ingredient.

6. A non-transitory medium as defined in claim 5, wherein the GUI functional block is responsive to input by the user to place the ingredient validation functional block in an operational state to:
   a. receive a second code from the code reader reading machine-readable data from a second container holding a second ingredient, and
   b. determine at least in part from the second code if the second ingredient matches the formulation ingredient.

7. A non-transitory medium as defined in claim 1, wherein the machine-readable data is optically read data.

8. A non-transitory medium as defined in claim 7, wherein the optically read data is a bar-code or a QR code.

9. A non-transitory medium as defined in claim 1, wherein the machine-readable data is an RFID data.

10. A non-transitory medium as defined in claim 1, wherein the composition includes a pharmaceutical or a skin-care composition.

11. A non-transitory medium storing computer-readable instructions which when read and executed by at least one processor of a computing device, implements:
   a. a Graphical User Interface (GUI) functional block configured for implementing a computerized GUI that provides a user of the computing device with an opportunity to specify a compounding formula for a composition,
   b. an ingredient validation functional block configured for:
      i. receiving a code input by a code reader reading machine-readable data on a container holding a first ingredient, wherein the code is associated with the first ingredient,
      ii. processing the code to determine if the first ingredient is a valid ingredient for the specified compounding formula, and
   c. a planetary mixer control functional block configured for:
      i. consulting a database arrangement at least partly on a basis of the specified compounding formula in order to determine mixing parameters for a planetary mixer, the mixing parameters being associated with the specified compounding formula, and
      ii. causing a motor assembly of the planetary mixer to apply superimposed rotation and revolution movements to a container in accordance with the mixing parameters determined from the consulting, and
   d. the planetary mixer control functional block being further configured to one of prevent operation of the motor assembly or display an error message on the GUI when the ingredient validation functional block determines that the first ingredient is not valid for the specified compounding formula.

12. A non-transitory medium as defined in claim 11, wherein the ingredient validation functional block determines that the first ingredient is not valid when the first ingredient is a wrong ingredient for the specified compounding formula.

13. A non-transitory medium as defined in claim 11, wherein the ingredient validation functional block determines that the first ingredient is not valid when the first ingredient has a use-by date that has passed.

14. A non-transitory medium as defined in claim 13, wherein the ingredient validation functional block is configured to consult the database arrangement to derive at least in part from the code the use-by date of the first ingredient.

15. A non-transitory medium as defined in claim 14, wherein the ingredient validation functional block is configured to consult the database arrangement to derive at least in part from the code a concentration of an active agent in the first ingredient.

16. A non-transitory medium as defined in claim 11, wherein the ingredient validation functional block determines that the first ingredient is not valid when the first ingredient has a wrong concentration of an active agent.

17. A non-transitory medium as defined in claim 11, wherein the machine-readable data is an optically read data.

18. A non-transitory medium as defined in claim 17, wherein the optically read data is a bar-code or a QR code.

19. A non-transitory medium as defined in claim 11, wherein the machine-readable data is an RFID data.

20. A non-transitory medium as defined in claim 11, wherein the ingredient validation functional block is configured for:
   a. receiving a plurality of codes sequentially input by the code reader as the code reader sequentially reads machine-readable data on a plurality of containers holding respective ingredients, wherein the plurality of codes are associated with respective ones of the ingredients,
   b. consulting the database arrangement at least in part on the basis of the specified compounding formula to derive a plurality of formulation ingredients to be used in preparing the composition, and
   c. determining at least in part on the basis of the plurality of codes if the respective ingredients match the plurality of formulation ingredients.

21. A non-transitory medium as defined in claim 11, wherein the composition includes a pharmaceutical or a skin-care composition.

22. A non-transitory medium storing computer-readable instructions, which when read and executed by at least one processor of a computing device, implement a method, including:
   a. implementing a computerized Graphical User Interface (GUI) that provides a user of the computing device with an opportunity to specify a compounding formula for a composition to be prepared by subjecting a plurality of ingredients to a mixing cycle in a planetary mixer, wherein the mixing cycle includes a plurality of mixing steps, where each mixing step includes applying superimposed rotation and revolution movements to a container including two or more of the ingredients therein,
   b. consulting a database arrangement at least partly on a basis of the specified compounding formula to derive mixing parameters for each step of the mixing cycle associated with the specified compounding formula,
   c. receiving a first code generated by a code-reader reading machine-readable data on a first container holding a first ingredient, wherein the first code is associated with the first ingredient,
   d. processing the first code for determining if the first ingredient is a valid ingredient for a first mixing step of the specified compounding formula,
   e. if step (d) determines that the first ingredient is a valid ingredient enabling the planetary mixer to perform the first mixing step of the plurality of mixing steps according to the determined mixing parameters for the first mixing step, f. receiving a second code input by the code reader in response to reading machine-readable data on a second container holding a second ingredient, wherein the second code is associated with the second ingredient, g. processing the second code to determine if the second ingredient is a valid ingredient for a second mixing step of the specified compounding formula, h. if step (g) determines that the second ingredient is a valid ingredient enabling the planetary mixer to perform a second mixing step of the plurality of mixing steps, including subjecting the first ingredient, the second ingredient and possibly additional ingredients to superimposed revolution and rotation movements according to the mixing parameters determined for the second mixing step.

23. A non-transitory medium as defined in claim 22, comprising determining that either one of the first ingredient and the second ingredient is not valid when the first ingredient or the second ingredient is a wrong ingredient for the respective mixing step of the specified compounding formula.

24. A non-transitory medium as defined in claim 22, comprising determining that either one of the first ingredient and the second ingredient is not valid when either one of the first ingredient and the second ingredient has a use by date that has passed.

25. A non-transitory medium as defined in claim 22, comprising determining that either one of the first ingredient and the second ingredient is not valid when either one of the first ingredient and the second ingredient has a wrong concentration of active agent.

26. A non-transitory medium as defined in claim 22, wherein the machine-readable data is an optically read data.

27. A non-transitory medium as defined in claim 26, wherein the optically read data is a bar-code or a QR code.

28. A computer-implemented method for compounding using a planetary mixer, comprising:

a. specifying on a computerized Graphical User Interface (GUI) a compounded product to be prepared by mixing a plurality of ingredients in the planetary mixer, b. generating a first prompt on the GUI directing a user to scan a first container holding a first ingredient with a code-reader to read machine-readable data on the first container, to generate a first code associated with the first ingredient, c. consulting a database at least in part on a basis of the first code and the specified compounded product to determine if the first ingredient is a valid ingredient for the specified compounded product, d. obtaining machine instructions for the planetary mixer for performing a first mixing step of a plurality of mixing steps for preparing the compounded product and applying the machine instructions to the planetary mixer to cause the planetary mixer to perform the first mixing step which includes subjecting a container in which is placed the first ingredient and an additional ingredient to a superimposed rotation and revolution movements, e. generating a second prompt on the GUI directing the user to scan a second container holding a second ingredient with the code-reader to read machine-readable data on the second container, to generate a second code associated with the second ingredient, f. consulting the database to determine if the second ingredient is a valid ingredient for the specified compounded product, g. obtaining machine instructions for the planetary mixer for performing a second mixing step of the plurality of mixing steps for preparing the compounded product and applying the machine instructions to the planetary mixer to cause the planetary mixer to perform the second mixing step which includes subjecting the container in which are placed the first ingredient, the second ingredient and the additional ingredient to a superimposed rotation and revolution movements, and h. one of disabling performance of the first mixing step or the second mixing step, or displaying an error message on the GUI if the method determines that the first or second ingredients, respectively, is not valid.

29. A computer implemented method as defined in claim 28, including monitoring a lid sensor of the planetary mixer to determine whether the lid of the planetary mixer is open or closed.

30. A computer implemented method as defined in claim 29, disabling execution of the second mixing step until the lid sensor indicates that the lid has been operated after completion of the first mixing step.

* * * * *